United States Patent
Bartolome et al.

(10) Patent No.: US 12,241,077 B2
(45) Date of Patent: Mar. 4, 2025

(54) ADENO-ASSOCIATED VIRUS (AAV) SYSTEMS FOR TREATMENT OF GENETIC HEARING LOSS

(71) Applicant: Eli Lilly and Company, Indianapolis, IN (US)

(72) Inventors: Christopher Bartolome, Billerica, MA (US); Luis David Jaramillo, Cambridge, MA (US); Adrian M. Timmers, Burlington, MA (US); Steven Pennock, Leominster, MA (US); Mark Shearman, Alachua, FL (US)

(73) Assignee: Eli Lilly and Company, Indianapolis, IN (US)

( * ) Notice: Subject to any disclaimer, the term of this patent is extended or adjusted under 35 U.S.C. 154(b) by 491 days.

(21) Appl. No.: 17/038,482

(22) Filed: Sep. 30, 2020

(65) Prior Publication Data

US 2021/0095313 A1    Apr. 1, 2021

Related U.S. Application Data

(60) Provisional application No. 62/907,834, filed on Sep. 30, 2019.

(51) Int. Cl.

| | |
|---|---|
| C12N 15/85 | (2006.01) |
| C07H 21/04 | (2006.01) |
| C12N 15/66 | (2006.01) |
| C12N 15/86 | (2006.01) |
| C12N 15/864 | (2006.01) |

(52) U.S. Cl.
CPC .............. *C12N 15/86* (2013.01); *C07H 21/04* (2013.01); *C12N 15/66* (2013.01); *C12N 15/8645* (2013.01); *C12N 2510/00* (2013.01); *C12N 2710/10041* (2013.01)

(58) Field of Classification Search
CPC ........ C12N 15/79; C12N 15/85; C12N 15/86; C12N 15/8645; C12N 2710/10041; C12N 2750/14143; C12N 2510/00; C12N 2800/22; C07H 21/04
See application file for complete search history.

(56) References Cited

U.S. PATENT DOCUMENTS

2005/0281786 A1    12/2005 Poulsen et al.

FOREIGN PATENT DOCUMENTS

| CN | 101522899 A | 9/2009 |
|---|---|---|
| CN | 108135991 A | 6/2018 |
| CN | 108350467 A | 7/2018 |
| CN | 109055499 A | 12/2018 |
| CN | 109310745 A | 2/2019 |
| WO | WO 2007/132169 A1 * | 11/2007 |
| WO | 2015/130840 A2 | 9/2015 |
| WO | 2017/136764 A1 | 8/2017 |
| WO | 2017/191274 A2 | 11/2017 |
| WO | 2022/056444 A1 | 3/2022 |

OTHER PUBLICATIONS

Wang, B., 2012 (Geneseq Accession No. AZX45003, computer printout, pp. 1-2).*
Iizuka et al., 2015 (Human Molecular Genetics, vol. 24, No. 13, p. 3651-3661).*
Ill et al., 2005 (Gene Therapy, 12: 795-802).*
GenBank Accession No. AY275646, *Homo sapiens* gap junction protein beta 2 gene, complete cds. 2 pages, Oct. 1, 2004.
Maeda et al., In vitro and in vivo suppression of GJB2 expression by RNA interference. Hum Mol Genet. Jun. 15, 2005;14(12):1641-50.
International Search Report and Written Opinion for Application No. PCT/US2020/053561, dated Feb. 19, 2021, 11 pages.
Crispino et al., BAAV mediated GJB2 gene transfer restores gap junction coupling in cochlear organotypic cultures from deaf Cx26Sox10Cre mice. PLoS One. 2011;6(8):e23279, 11 pages.
GenBank Accession No. MH311557, *Homo sapiens* isolate HLP20 gap junction beta 2 protein gene, complete cds. 1 page, Feb. 13, 2019.
GenBank Accession No. NM_001004099, Rattus norvegicus gap junction protein, beta 2 (Gjb2), mRNA. 3 pages, Aug. 2, 2019.
Gyorgy et al., Gene Transfer with AAV9-PHP.B Rescues Hearing in a Mouse Model of Usher Syndrome 3A and Transduces Hair Cells in a Non-human Primate. Mol Ther Methods Clin Dev. Nov. 20, 2018;13:1-13.
Jackson et al., Better Targeting, Better Efficiency for Wide-Scale Neuronal Transduction with the Synapsin Promoter and AAV-PHP. B. Front Mol Neurosci. Nov. 4, 2016;9:116, 11 pages.
Kemperman et al., Hearing loss and connexin 26. J R Soc Med. Apr. 2002;95(4):171-7.
Lefebvre et al., Connexins, hearing and deafness: clinical aspects of mutations in the connexin 26 gene. Brain Res Brain Res Rev. Apr. 2000;32(1):159-62.
Smith et al., GJB2-Related Autosomal Recessive Nonsyndromic Hearing Loss. GeneReviews. University of Washington, Seattle, MP Adam (Ed.). 31 pages, Jul. 20, 2023.
Thomas et al., Scalable recombinant adeno-associated virus production using recombinant herpes simplex virus type 1 coinfection of suspension-adapted mammalian cells. Hum Gene Ther. Aug. 2009;20(8):861-70.

(Continued)

*Primary Examiner* — Shin Lin Chen
(74) *Attorney, Agent, or Firm* — Sterne, Kessler, Goldstein & Fox P.L.L.C.

(57) ABSTRACT

Described herein are codon optimized nucleic acid sequences encoding gap junction protein beta 2 (GJB2), and associated genetic elements, for use in recombinant adeno-associated virus (rAAV)-based gene therapy. The rAAV vectors through which GJB2 is packaged can be used for targeted delivery to patients suffering from genetic hearing loss, including patients with autosomal mutations, recessive or dominant, in the GJB2 gene.

18 Claims, 39 Drawing Sheets

Specification includes a Sequence Listing.

(56) References Cited

OTHER PUBLICATIONS

Takada et al., Connexin 26 null mice exhibit spiral ganglion degeneration that can be blocked by BDNF gene therapy. Hear Res. Mar. 2014;309:124-35.

* cited by examiner

FIG. 2
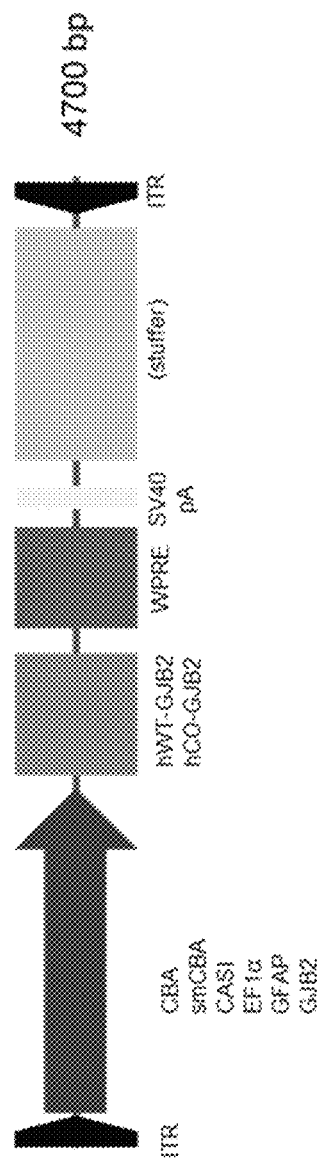
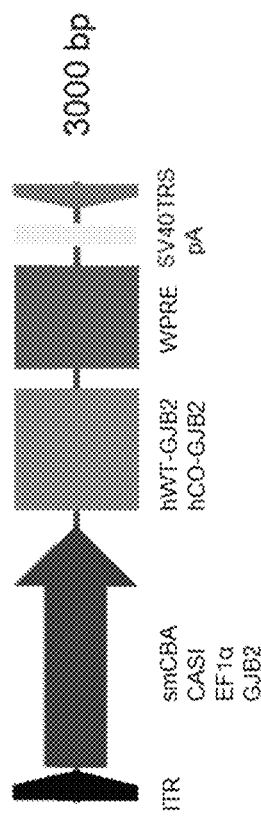

FIG. 3

```
ctcagatctgaattcggtaccagtattaatagtaacaattacgggtcattagtcatagcccatatatggagttccgcgttacataactacgtaaatgcccgcctggctgaccgcc
caacgaccccgcccattgacgtcaataatgacgtatgttcccatagtaacgccaataggactttccattgacgtcaatgggtggagtatttacggtaaactgcccacttggcagtaca
tcaagtgtatcatatgccaagtacgccccctattgacgtcaatgacggtaaatggcccgcctggcattatgcccagtacatgaccttatgggactttcctacttggcagtacatctacgtatt
agtcatcgctattaccatggtcgaggtgagccccacgttctgcttcactctccccatctcccccccctccccacccccaattttgtatttatttattttattaatttgtgcagcgatgggcgg
ggggggggggggcggggcgcgggcgcggggcgaggggcggggcggggcgaggcgggagaggtgcggcggcagccaatcagagcggcgcgctccgaaa
gtttcctttatgcagcgaggcggcggcggcggcggcccctataaaaagcgaagcgcgcggcgggcgggagtccttctgatcagagcttggttggttaagacgcttggttctttttgtggctgc
gccgccgcctgagggctcgagaggcgcgctcaacaaggtgcgggagagcgggtgtgtgtgcgtgtgtgcgtgggggagccctgggccggg
cgtgagcgctcgaggctgtgcggggaccgcgcagtgtgtggcggtcccgaaagctgggcccgcggttcacaagctccccgccccccgccccggggttgcgagcacggccc
gtgcgggtccctgagttgcagggcgggagggcgtgcgccgcccaaggcgcgcggagacccctgcctctcccggctcgcccgggggcagggcgggaagggggctcgggccctggc
ggagaggggctccgtacgggcgcggcagccccgccggagcgccgggagacggctcaactaaatgcctttatgtgtaatgccttttatgtggtaatgcgggcggcccgcagtcccggg
ctgtgcggagccgaaatcggaggccggcgggtccttgcgggcgctcggaggccgggggcggagcccgcagcatgccagcgaaggtgccttgccttgccggcatgcagggacggggtaattggcagggcaggcgggttcggttctggcttttggaccggggct
gccgcgcgcggccggtccttccctccctctccagcctcggctcctcagccctcaggctccttcctttccttctttcctaca
```

FIG. 4 gagtcaatgggaaaaacccattgggagccaagtcacactgactcaattagggagtcaatggggtgagtcaacaggaaagtcccattgga
gccaagtacaattgagtcccattgcccagtacataaggttttgcccagtacataaggacttcccagtacataaggtcaatggttttgcccagtacaaagt
caatgggtttgcccagtacataaggtcaatggggtgaatcaacaggaaagtcccattggagccaagtacactgagtcaatggacttcccagtacaaggt
caataggggtgagtcaatggttttccattattggcacataaaggtcaatagggtgactagtgggaagagcatgcttgaggctgagtgcccctcagtggcagagaca
catggcccacagtccctgagaagtggggagagggtggcaattgaactggtgcctagagaaggtgggcttgggtaaactgatgtgtgtactgctccaccttc
cccagggtggggagaaccatatataagtcagtagtctctgtgaacattcaagcttctgccctctcctgagcttggtaagtcactgactgtctatgcctggaaaggtgggca
ggaggtgggcagtgcaggaaaagtggcactgtgaaccctgaaccctgcagcctgacaattgactaaccttctcttcctctcctgacag

FIG. 5 ggagttccgcgttacataacttacgtaaatgccgcctgctgaccgcgccaacgaccccgcccattgacgtcaaatgaccgtatgttccatagtaacgccaatagggactttcc
attgacgtcaatgggtggagtatttacggtaaactgcccacttggcagtacatcaagtgtatcatatgccaagtacgccccctattgacgtcaatgacggtaaatggcccgcctatta
tgcccagtacatgaccttatgggactttcctacttggcagtacatctacgtattagtcatcgctattaccatggtcgaggtgagccccacgttctgcttcactctccccatctcccccctccc
cacccccaattttgtatttatttattttaattatttgcagcggccgcaatagagagccctaaaaaacaggtaagtaccgtcctaaacaggtaagtaccgcctatagactgg
gcgggaggtcgcggcgctcagagcggctccaatagagagcctcagccccgtccccgcctttatgcggccccctaaaaacaggtaagtaccgcctatagactgg
gtgcctccgcgtgctgccttgccccgcctcgccccgccgcgtccacgtgcactgccagcgaagggcgcagcagcgagcgtcctgatcctccgccgacgtcaggacctcgccgacgtcaggacgtcgctca
gcgcctccgcgggcgcccctctcacggccagatcagcagaaggacattttaggacgggactggtgactcaggcactgtttctttccagagagcgaggaacaggcccgctgctca
taagactcggcctttagaaacccccagtatcagcagaaggacattttaggacgggactggtgactcaggcactgtttctttccagagagcgaggaaaagtagtcc
cttctcggcgattctcggaggatcgcgtgggcgtcgagatcgagaacgccgatgatgcctctactaaccatgttcatgtttctttttttctacaggtcctgggtgacgaacag

FIG. 6 cctcagatcgaattcgtacctagttattaatagtaatcaattacgggtcattagttcatagtccatatatgagttcgcgttacataactttacggtaaatgcccgcctgctgaccg
cccaacgaccccgccattgacgtcaataatgacgtatgttcccatagtaacgccaataggactttccattgacgtcaataggactatttacggtaaactgcccacttggcagta
catcaagtgtatcatatgccaagtacgccccctattgacgtcaatgacggtaaatggcccgcctggcattatgcccagtacatgaccttacgggactttcctacttggcagtacatctacgt
attagtcatcgctattaccatggtcgaggtgagccccacgttctgcttcactctccccatctcccccctccccccccaatttgattattattttaattatttgtgcagcgatggggc
gggggggggggcgcgcgccaggcggggcggggcgaggggcggggcggggcgaggcgtgccgcgccaatcagagcggcgctccga
aagttccttttatggcgagcggcccccgctctgactactcccgccgttactccacagttgacggtgagcggggacggcccttctcctcggcgtaatagcgcttaatgacgcttcttttctgtgg
ctcgcgccgcccgcgtctctgactctgtaaccatgtcatgtcaagcttcatgccttttcctacagctctctggtaatgctgttatgctgttaatgctgtcaagcgttaatcgcca

FIG. 7

GTCTGCAAGCAGAGACCTTGGCAGCATTGGCTGGCGCCCCCCAGGGCCTCTCCTCTTCATGCCCAGTGAATGACTCACCTTGG
CACAGACAAATGTTCGGGTGGGCACAGTGCCTGCTTCCCGCCGCACCCAGCCCCTCAAATGCCCTTCCGAGAAGCC
CATTGAGTAGGGCCTTGCATTGCACCCAGCCTGACACTCTTGGCATAAAGCAGCACAGCCCCTAGGGCT
GCCCTTGCTGTGCGCCACCGGGTGGAGAACAAGGCTCTATTCAGCCTGTGCCCAGGAAGGGGATCAGGGATG
CCCAGGCATGCAGGTCTGCAGGAGGGCTGTCTGTCCCAGGAAGTCCAAGGACACAAATGGGTGA
GGGGACTGGGCAGGTTCTGACCCTGTGGACCAGAGGGCGTAGATGGACCTGAAGTCTGAAGTCTTCCAGGAGGTTCTTCCATCT
CCAGGTCTGATGTGTGGGAACTCGAGGAGCCAGTCCTCAAAACCATCCCAAGCTTCCAAACCCAGAGGGCTGTCAAGGTCTTCCATCT
GGAATAAAGACGAGCCAGAGGAAGGGTGACCTGACACGGCTAACGGCTTTGTGGAGCTGTCAAGCCTAAGCCTAAGTCCTGGAGAGAGG
CACAGGAGCCAGAGGAAGGGTGACCTGACACGGCTAACGGCTTTGTGGAGCTGTCAAGCCTAAGTCCTGATAAGCAAGAGAGTGC
CGGCCCCCTCTTGCCCTATCAGGAGGACCCTCCACTGCCACATAGAGCAGAGAGGTGGCCCTTAGACAAGGGCTGTGTCCAATC
CCAAGAGTCTGCTGGGAATGAGCCGACTTACAGCTGAGTAGGAAATGAGGTGGCCCTTGGGTTATGAGACAAGGTTCATTCTTCGCCAAAT
CCAAGAGTCTGCTGGGAATGAGCCGACTTACAGCTGAGTAGGAAATGAGGTGGCCCTTGGGTTATGAGACAAGGTTCATTCTTCGCCAAAT
TCCAGCACCTTGCAGCCCTTCCTTCCTTTTTTTTTTTTTTGTGAGACAAGGTGAAATCAAAAGTTGGAAGCAGTTGAAAGCAGTCAGGAGT
TCATCTGGTACAGCCCTTCCTTCCTTTTTTTTTTTTTTGTGAGACAAGGTGAAATCAAAAGTTGGAAGCAGTTGAAAGCAGTCAGGAGT
GGGCAAACACAGCCACCCACTCAGCCTGCAACCTAGGGCCTCAACCTCTGCAACCTCTGCAACCTCAAAGTGCTGGATT
ACAAGCATGAGCCACCACCACTTCCTAGAGAGGGTCCTGCCCAGGAAGCTCTGCCTCTGTGGCACAGTGACTTGCTCGGCTGAAGTGCTGGATT
CCCTTTCTTGACCATGCCTCAGCAGGAGTTGGCGTGGCCCCAACCCCACCCCACCCTCGCAATCCCTGCAATCCCCCTCGCAATCCCAACCAA
TACCCTTCCCCCATAGCTGGGCGGGCCCAACCCCACCCTCGCAATCCCTGCATCCCTGCAATCCCCCTCGCAATCCCCAACCAA
GCTCTCCCCATAGCTGGGCTGGGCCCAACCCCACCCTCGCAATCCCCCTCGCAATCCCCCCGCAATCCCCCTCGCAATCCCCAACCAA
TCGCCCAGTCTAGCCCACTCCTTCATAAAGCCCTTCATAAAGAGGAGCAGAGAGCCAGAGCAT

FIG. 8

CTCATAAATGCCAAGTCCTCTCGCACTATGCGGAGTACA
GAGGACAACGACCACAGCCATCCCTGAACCCCGCCCAC
GGCACAGCGCCGGAGCCGGGGTCTGGGGCGCCGCTTC
CTGGGGGGTCCGACTCTCAGCGCCGCCCCGCGTTCACCC
GGGCCGCCAAGGGTGGGGAGGCGGTGGGGCACTTGGGG
TAACCGGGGGAGACTCAGGGCGTGGGGCACTTGGG
GAACTCATGGGGCTCAAAGGAACTAGGAGATCGGG
ACCTCGAAGGGACTTGGGGGGTTCGGGGCTTTCGG
GGGCGGTCGGGGTTCGCCGGACCGGAAGCTCTGA
GGACCCAGAGGCCGGGCGCTCCGCCCGGGCC
GCCCCCTCGTAACTTTCCAGTCTCGAGGGAAGAGG
CGGGGTGTGGGGTGCGGTTAAAAGGCGCACGGGCGG
GAGACAGGTGTTGCGGCCCGCAGGCCCGGCGTC
CTCTCCCGACTCGGAGCCCTCGGCGCCGGCCCGGCTC
AGGACCCGCTAGGAGCGCCAGGAGCCCCAGCGCAGA
GACCCCAACGCCGAACGCCAGGTGAGCCCGCCCGCGC
GCTTCCTCCCGACGCAGGAACCTGGCGCGGAGGACCGC
CTGCCCGGCCAGGAGCGCCCGGCCGCGTGGGTCTGG
GAGACCCAGAGCGGTTGCCCGGCCGCGTGGGTCTGG
GGAACCGGGGCTGGACGCCAACACGTCCTTGGGCC
GGGGGGCGGGGCCGCCTTCTGAGCGGCGTTCT
GCGGCCGAGTCCGGAGTCGGAATGGGGCCGGG
GAAGTGGACGCGATGCGCCCGGGGTGCGAGTGG
GGCCGGGCGCGGGGAGGGGAAAGGGGGGGC
GAGCCGCCAGCGACGGAGGTTTGTGTGCCGATGTCC
CTTCGGGTACTCTAGCGCAGCCGCCTGGTACTTGAC
CCACTGCCACCAAACGTTTAAATTCACCGAAAGCTTAG
CT

FIG. 9

5'-3': for single stranded (ss) and self-complimentary (sc) AAV genomes
ttggccactccctctgcgctcgctcgctcactgaggcggccactgaggccgaccaaaggtgcgccgacgccggctttgcc
cgggcggccggcctcagtgagcgagcgagcgcgcagagagagggagtggccaactccatcactaggggtc 3'-5': for single stranded (ss) AAV genomes only
gaacccctagtgatgatggagttggccactccctctgcgctcgctcgctcactgaggccgcccggcaaagcccgg
gcgtcgggcgacctttggtcgcccggcctcagtgagcgagcgagcgcgcagagaggagggagtggccaa 3'-5': for self-complimentary (sc) AAV genomes only
ccactccctctgcgctcgctcgctcactgaggccgcccgggcgaccaaaggtcgcccgacgcccgggctttgcccgg
gcggcctcagtgagcgagcgagcgcgcag

FIG. 10

ATGGATTGGGGCACGCTGCAGACGATCCTGGGGTGTGAACAAACACTCCACCAG
CATTGGAAAGATCTGGCTCACCGTCCCTCTTCATTTTCGCATTATGATCCTCGTGTGGC
TGCAAAGGAGGTGTGGGGAGATGAGCAGGCCGACTTTGTCTGCAACACCCTGCAGC
CAGGCTGCAAGAACGTGTGCTACGATCACTACTTCCCCATCTCCCACATCCGGCTATGG
GCCCTGCAGCTGATCTTCGTGTCCACGCCAGGCTCCTAGTGGCCATGCACGTGGCCT
ACCGGAGACATGAGAAGAAGAGGAAGTTCATCAAGGGGGAGATAAAGAGTGAATTT
AAGGACATCGAGGAGATCAAAACCCAGAAGGTCCGCATCGAAGGCTCCCTGTGGTG
GACCTACACAAGCAGCATCTTCTTCCGGTCTTCCATGCAGCGTGGTGAACGCCTGGCC
TCTATGTCATGTACGACGGCTTCTCCATGCAGCTGCTTTGTGTCCCGGCCACGGAGAAGACTGTCTTCACA
TTGTCCCAACACTGTGGACTGCAGTGTCTCTGGAATTTGCATCCTGCTGAATGTCACTGAATGTGTTA
GTGTTCATGATTGCAGTGTCTCTGGAATTTGCATCCTGCTGAATGTCACTGAATGTGTTA
TTTGCTAATTAGATATTGTTCTGGGAAGTCAAAAAGCCAGTT

FIG. 11

ATGGACTGGGGCACCCTGCAGACTATCCTGGGGGGCCGTCAATAAGCATTCAACTAGCATCGGAAAGATTTGGCTGACTGTC
CTGTTTATCTTCGGATCATGATCCTGGTGGTGGCCAGCAAGTGGGGACGAGCCGATTCGTGTGCAAC
ACACTGCAGCCAGGCTGCAAGAACGTGCTACGACCACTATTTCCCATCTCTCACATCAGGCTGTGGGCCCTGCAGCTG
ATCTTCGTGAGACACCCGCTGCTGGTGCAATGCAGTGGCCGTATCGGAGAACACGAGAAGAAGCGCAAGTTTATCAAG
GGCGAGATCAAGAGCGAGTTCAAGGATATCGAGGAGATCAAGACACAAGTCAAGAAGGCTCCTGTGGTGGAC
CTACACAAGCTCCATCTTCTTCGGTGATCTTCGAGGCGCCGCCTTTATACGTGTTCTATGTGATTGATGTACGACGCCTTTCTAT
GCAGGCGGCTGGTGTTATGATCGCCGTGTCTGCAACGCCGCCCTGTCTGCATCCTGGCATCCTGAACGTGAACCGAGCTG
GTTCACCTGGTGTTATGATCGCCGGTCGTGAACGTGAACCGAGCTGGACCGAGCTGTGCTACCGAGACAGT
TGTAGTGGAAAGAGCAAAAAACCCGTG

FIG. 12

ATGGACTGGGAACATTGCAACTATTTGGGAGGAGTCAACAAGCATTCAACTAGCATTCGGAAGATCTGGCTGACCGTGC
TGTTCATCTTTCGCATCATGATTCGTGGTGGCCGCTAAGGAAGTCTGGGCGATGAACAGGCCGACTTCGTGTGTAACAC
GCTGCAGCCCGGTTGCAAAACGTCTACGATCACTACTTCCCCATCTCACACATTAGACTGTGGGCGCTCAGCTGATT
TTCGTGTCCACCCGGCACTTCTTGTGCGATGCACGGCTACGGCGGCACGAGAGAAGGAAGTCATTAAGGG
CGAAATCAAGTCCGAGTTCAAGGACATCGAAGACCAGAAGTCCGCATTGAGGGCTCCTCTGGTGGACCTA
CACCTCGTCGTCCATCTCTCCGGGTCATATTCGAGGCCCTTTATGTACGTGTTTACGACGGTTCAGCATGC
AAAGACTCGTCAAGTGCAACGCTTGCCCCAATACGTGGATTGCTTGTCCCGCCGACGAGAAAACTGTGT
TCACTGTGTTCATGATCGCCGTGCTGTCCGGCATCTGAACGAGCTGCTGACGAGCTGTATCTCCTGATCCGGTACTG
TAGCGGAAAGTCGAAGAAGCCTGTG

ATGGGATTGGGGGACGCTCCAGAGTACTTGGCGGGGTAAACAAACATTCCACCTCAATTGGCAAATCTGGCTCACAGTCC
TCTTCATCTTCAGAATAATGATACTCGTGGTTGCCGTTGAAGAAGTTTGGGGTGACGAGCAAGCCGATTTCGTCTGTAACACC
CTCCAACCAGTTGCAAAATGTCTTCCTATTAGCCATATAGACTCTGGCCCTGCAACTATCTTC
GTTTCCACTCCTGCTCTCGTCGTTAGCTATCACGTTGCCTATGCGAAAAACGAAATTCATTAAGGAGAGAT
TAAGAGTGAATTCAAGGATATTGAAGAGATTAAAACGCAAAAGTTAGGACTACTGTGGTGGACTATACCAGTAG
CATCTTTTTAGGGTCATTTTCGAAGCTGCTTTCATGTATGTTTCTATGTAATGTACGACGGTTTCTCCATGCAACGCTTGGTT
AAATGTAACGCCTGGCCATGCCCTAATACGGTTGATTGCTTGTCTCCCGCCCTACTGAAAAGACAGTGTTTACCGTTTCAT
GATCGCCGGTAAGTGGAATTGTATCCTTCTTGAACGTGACCGAGTTGCTATCCTTATTCGTTACTGTTCAGGAAAAAGTAA
AAACCAGTA

FIG. 13

FIG. 14 tacccatacgatgttccagattacgct

FIG. 15 aatcaacctctggattacaaaattgtgaaagattgactgtatcttaactatgtgctccctttacgctatgtgatacgctgctttaatgcctatgtcccgtatggctttcat
ttctcctccttgataaaatcctggttgctgtctcttatgagpagttgtggcccgttgcaggttgggtgcgtgttcaggraacgtgccgtgttgccactgttgcgcaacccccactgttgcggcattgccaac
cacctgtcagctccttcgggacttgcgtttcccctccattgccacgcggaactcatcgcgcgtctgccctgtgtggactgaaggggctgctgttgggactgacattccg
tggtgtttgtcgggaaatcatcgctccttccttgcctgcctgtgtgccactgggatccgtgccgacctccttgcaccgtgccccctccaatccagcgaccttcctcccgc
ggcctgctcgcggcctctcgggcctcttgcctttgcctttgccgatccctttggccgcctcccgc

FIG. 16 taagatacattgatgagtttggacaaaccaaactagaatgcagtgaaaaaatgcttattgtgaaattgtgaaattgtgaatgctattgcttattgtaaccattataagctgcaataaacaagt

FIG. 17 ctgtgccttctagttgccagccatctgttgtttgccctccgtgcctccttgaccctgaaggtgccactcccactgtccttcctaataaaatgaggaaattgcatcgcattgtctgagta
ggtgtcattctattctggggggtggggtggggcaggacagcaaggggaggattggaagacaatagcaggcatgctgggga

FIG. 18A

ATGGACTGGGGCACGCTGCAGACTATCCTGGGGGTGTCAACAAGCATTCAAC
TAGCATCGGAAAGATCTGGCTGACCGTCCTGTTCATCTTTCGCATCATGATCCTC
GTGGTGGCCGCTAAGGAAGTGTGGGGCGACGAGCAGGCCGATTTCGTGTGTA
ACACCCTGCAGCCAGGTTGCAAAAACGTCTGCTACGATCACTACTTTCCCATCTC
CCACATTAGACTGTGGGCCCTGCAGCTGATCTTCGTGTCCACCCCTGCGCTGCTA
GTGGCCATGCACGTGGCCTATCGGCGACACGAGAAGAAACGGAAGTTCATTAA
GGGCGAGATCAAGAGCGAGTTCAAGGATATCGAAGAGATCAAGACCCAGAAG
GTCCGCATTGAGGGCTCCCTGTGGTGGACCTACACCAGTCCATCTCTTTCGG
GTCATCTTCGAGGCCGCTTTATGTACGTGTTCTATGTGATGTACGACGGTTTCTC
CATGCAACGGCTGGTGAAGTGCAACGCCTGGCCTTGCCCTAATACTGTGGATTG
CTTCGTGTCCGCCCACCGAGAGAACAGTGTTCACCGTGTTCATGATGCCGT
GTCTGGCATCTGCATCCTGTGAACGTGACCGAGCTGTGTGCTATCTCCTGATCCGG
TACTGTAGTGGAAAGTCAAAAAACCAGTGTAA

FIG. 18B

MDWGTLQTILGGVNKHSTSIGKIWLTVLFIFRIMILVVAAKEVWGDEQADFVCNT
LQPGCKNVCYDHYFPISHIRLWALQLIFVSTPALLVAMHVAYRRHEKKRKFIKGEIK
SEFKDIEEIKTQKVRIEGSLWWTYTSSIFFRVIFEAAFMYVFYVMYDGFSMQRLVK
CNAWPCPNTVDCFVSRPTEKTVFTVFMIAVSGICILLNVTELCYLLIRYCSGKSKKP
V

FIG. 19A

| Serotype/Variant | Postnatal Mouse Cochlea (Akil and Holt data) | | | | | Young Adult Guinea Pig Cochlea (Yehoash data) | | | | | |
|---|---|---|---|---|---|---|---|---|---|---|---|
| | IHC (%) | OHC (%) | SC (%) | base | apex | SGN? | IHC (%) | OHC (%) | SC (%) | base | apex | SGN? |
| AAV2-deltaHsMax-CB-hGFP | 0 | 0 | 0 | none | none | none | 0 | 0 | 0 | none | none | n.d. |
| AAV2-MeB-CB-hGFP | 50 | 50 | 100 | str | str | none | 55 | 0 | 0 | str | mod | n.d. |
| AAV2-qYF-CB-hGFP | 50 | 10 | 70 | str | str | none | 50 | 10 | 70 | str | mod | n.d. |
| AAV2-P2V3-CB-hGFP | 75 | 85 | 95 | str | str | none | tbd* | tbd* | tbd* | tbd | tbd | tbd |
| AAV2-CB-hGFP | 2 | 0 | 5 | weak | weak | none | | | | | | |
| AAV2-tYF-CB-hGFP | 80 | 85 | 90 | str | str | none | 35 | 0 | 0 | mod | mod | n.d. |
| AAVrh10-CB-hGFP | 3 | 1 | 2 | weak | weak | mod | | | | | | |
| AAV2-7m8-CB-hGFP | 75 | 40 | 40 | str | str | str | | | | | | |
| Anc80L-CB-hGFP | 90 | 30 | 0 | str | mod | mod | 70 | 5 | 0 | mod | mod | n.d. |
| AAV2-MeA-CB-hGFP | 10 | 15 | 30 | str | weak | weak | | | | | | |
| AAV2-P2V2-CB-hGFP | 20 | 70 | 60 | mod | weak | mod | tbd* | tbd* | tbd* | tbd | tbd | tbd |
| AAV2-MeBtYFTV-CB-hGFP | 5 | 5 | 95 | mod | str | str | | | | | | |
| AAV2-P2V6-CB-hGFP | 20 | 40 | 90 | mod | mod | mod | | | | | | |
| AAV2-P3PR3-CB-hGFP | 5 | 5 | 75 | str | weak | weak | | | | | | |
| AAV2-DGEDF-CB-hGFP | 50 | 20 | 60 | mod | weak | mod | | | | | | |
| AAV2-MeBdYF-CB-hGFP | 60 | 15 | 90 | mod | weak | mod | | | | | | |

% = percent GFP-positive cells (assessed over multiple sections)
IHC = inner hair cells (single row); OHC = outer hair cells (triple row)
SC = support cells (includes pillar cells, border cells, phalangeal cells, outer limiting cells, and a portion of the external supporting cells)
base/apex/SGN = strength of transduction observed in cochlear base, apex, or underlying spiral ganglion neurons (none, weak, moderate[mod], str[ong])
tbd = to be determined (tbd* = data to be obtained from both Scala Tympani and Scala Media injections); n.d. = not determined
note purple values indicate further data is expected (mean values to be adjusted accordingly)

ADENO-ASSOCIATED VIRUS (AAV) SYSTEMS FOR TREATMENT OF GENETIC HEARING LOSS

CROSS-REFERENCE TO RELATED APPLICATIONS

This application claims benefit under 35 U.S.C. § 119(e) of U.S. Provisional Application No. 62/907,834 filed Sep. 30, 2019, the content of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Sep. 28, 2020, is named 119561-01902_SL and is 31,079 bytes in size.

FIELD OF THE INVENTION

The present invention relates to the field of gene therapy, including AAV vectors for expressing an isolated polynucleotides in a subject or cell. The disclosure also relates to nucleic acid constructs, promoters, vectors, and host cells including the polynucleotides as well as methods of delivering exogenous DNA sequences to a target cell, tissue, organ or organism, and methods for use in the treatment or prevention of genetic hearing loss.

BACKGROUND OF THE INVENTION

Gene therapy aims to improve clinical outcomes for patients suffering from either genetic mutations or acquired diseases caused by an aberration in the gene expression profile. Gene therapy includes the treatment or prevention of medical conditions resulting from defective genes or abnormal regulation or expression, e.g. underexpression or overexpression, that can result in a disorder, disease, malignancy, etc. For example, a disease or disorder caused by a defective gene might be treated, prevented or ameliorated by delivery of a corrective genetic material to a patient, or might be treated, prevented or ameliorated by altering or silencing a defective gene, e.g., with a corrective genetic material to a patient resulting in the therapeutic expression of the genetic material within the patient.

The basis of gene therapy is to supply a transcription cassette with an active gene product (sometimes referred to as a transgene or a therapeutic nucleic acid), e.g., that can result in a positive gain-of-function effect, a negative loss-of-function effect, or another outcome. Such outcomes can be attributed to expression of a therapeutic protein such as an antibody, a functional enzyme, or a fusion protein. Gene therapy can also be used to treat a disease or malignancy caused by other factors. Human monogenic disorders can be treated by the delivery and expression of a normal gene to the target cells. Delivery and expression of a corrective gene in the patient's target cells can be carried out via numerous methods, including the use of engineered viruses and viral gene delivery vectors.

Adeno-associated viruses (AAV) belong to the Parvoviridae family and more specifically constitute the dependoparvovirus genus. Vectors derived from AAV (i.e., recombinant AAV (rAVV) or AAV vectors) are attractive for delivering genetic material because (i) they are able to infect (transduce) a wide variety of non-dividing and dividing cell types including myocytes and neurons; (ii) they are devoid of the virus structural genes, thereby diminishing the host cell responses to virus infection, e.g., interferon-mediated responses; (iii) wild-type viruses are considered non-pathologic in humans; (iv) in contrast to wild type AAV, which are capable of integrating into the host cell genome, replication-deficient AAV vectors lack the rep gene and generally persist as episomes, thus limiting the risk of insertional mutagenesis or genotoxicity; and (v) in comparison to other vector systems, AAV vectors are generally considered to be relatively poor immunogens and therefore do not trigger a significant immune response (see ii), thus gaining persistence of the vector DNA and potentially, long-term expression of the therapeutic transgenes.

Nonsyndromic hearing loss and deafness (DFNB1; also known as Connexin 26 deafness) is autosomal recessive and is characterized by congenital non-progressive mild-to-profound sensorineural hearing impairment. The GJB2 gene encodes connexin-26 which is expressed in cochlear support cells, forming gap junctions that control potassium homeostasis which is critical for the survival and function of hair cells and normal hearing. Mutations in GJB2 impair gap junctions and cochlear homeostasis leading to hair cell dysfunction and hearing loss.

Hearing loss is the most common inherited sensory disorder. In developed countries such as the United States, genetic mutations are responsible for the vast majority of hearing loss in young children, which is estimated to affect 1 out of 500 children before speech develops (Shearer et al., "Hereditary Hearing Loss and Deafness Overview", 2017). Because congenital hearing loss is one of the most prevalent chronic conditions in children, neonatal screening is routinely performed. This is typically followed by genetic testing in those cases where a deficit has been detected.

Genetic testing can be used to diagnose DFNB1 by identifying biallelic pathogenic variants in GJB2 which encompass sequence variants and variants in upstream cis-regulatory elements that alter expression of the gap junction beta-2 protein (Connexin 26). When the GJB2 pathogenic variants causing DFNB1 are detected in an affected family member, carrier testing for at-risk relatives, prenatal testing for pregnancies at increased risk, and preimplantation genetic diagnosis are possible. Smith & Jones. Nonsyndromic Hearing Loss and Deafness, DFNB1. 1998. In: Adam, et al. Eds. GeneReviews. University of Washington, Seattle; Kemperman et al. Journal of the Royal Society of Medicine 2002 95: 171-177. Because the cochlea is surgically accessible and local application into a relatively immune-protected environment is possible, gene therapy using viral vectors is an attractive approach for treating hearing loss.

However, there remains a need for effective therapies to treat sensorineural hearing loss.

SUMMARY OF THE INVENTION

The technology described herein relates to methods and compositions for treatment or prevention of hearing loss by expression of gap junction protein beta 2 (GJB2) from a recombinant adeno-associated virus (rAAV) vector, where the rAAV vector comprises a GJB2 nucleic acid sequence that has been codon optimized. In some embodiments, the rAAV vector comprises a GJB2 nucleic acid sequence that has been codon optimized and combined a promoter that has been tested for optimal GJB2 expression. Thus, the disclosure relates to a rAAV vector through which GJB2 can be packaged for targeted delivery to patients suffering from genetic hearing loss, including patients with autosomal mutations, recessive or dominant, in the GJB2 gene. Mutations in GJB2 impair gap junctions and cochlear homeostasis, leading to hair cell dysfunction and hearing loss. A goal of GJB2 gene therapy as described herein is to restore functional gap junctions and preserve hair cells to improve hearing.

According to one aspect, the disclosure provides an isolated polynucleotide comprising a nucleic acid sequence encoding GJB2. According to some embodiments, the nucleic acid sequence is a non-naturally occurring sequence. According to some embodiments, the nucleic acid sequence encodes mammalian GJB2. According to some embodiments, the nucleic acid sequence encodes human, mouse, or rat GJB2. According to some embodiments, the nucleic acid sequence comprises SEQ ID NO: 10. According to some embodiments, the nucleic acid sequence is codon optimized for mammalian expression. According to some embodiments, the nucleic acid sequence comprises SEQ ID NO: 11, SEQ ID NO: 12 or SEQ ID NO: 13.

According to some embodiments, the nucleic acid sequence comprises a sequence at least 85% identical to SEQ ID NO: 11, a sequence at least 85% identical to SEQ ID NO: 12, a sequence at least 85% identical to SEQ ID NO: 13 or a sequence at least 85% identical to SEQ ID NO: 18. According to some embodiments, the nucleic acid sequence is codon optimized for expression in human, rat, or mouse cells. According to some embodiments, the nucleic acid sequence is a cDNA sequence. According to some embodiments, the nucleic acid sequence further comprises an operably linked hemagglutinin (HA) C-terminal tag. According to some embodiments, the nucleic acid sequence is operably linked to a promoter. According to some embodiments, the promoter is an ubiquitously-active CBA, small CBA (smCBA), EF1a, CASI promoter, a cochlear-support cell promoter, GJB2 expression-specific GFAP promoter, small GJB2 promoter, medium GJB2 promoter, large GJB2 promoter, or a sequential combination of 2-3 individual GJB2 expression-specific promoters. According to some embodiments, the promoter is optimized to drive high GJB2 expression. According to some embodiments, the nucleic acid sequence further comprises an operably linked 3'UTR regulatory region comprising a Woodchuck Hepatitis Virus Posttranscriptional Regulatory Element (WPRE). According to some embodiments, the nucleic acid sequence further comprises an operably linked polyadenylation signal. According to some embodiments, the polyadenylation signal is an SV40 polyadenylation signal. According to some embodiments, the polyadenylation signal is a human growth hormone (hGH) polyadenylation signal. According to some embodiments, the polynucleotide of any of the aspects and embodiments herein further comprises a 27-nucleotide hemagglutinin C-terminal tag; operably linked to one of the following promoter elements optimized to drive high GJB2 expression: (a) an ubiquitously-active CBA, small CBA (smCBA), EF1a, or CASI promoter; (b) a cochlear-support cell or GJB2 expression-specific 1.68 kb GFAP, small/medium/large GJB2 promoters, or a sequential combination of 2-3 individual GJB2 expression-specific promoters; operably linked to a 3'-UTR regulatory region comprising the Woodchuck Hepatitis Virus Posttranscriptional Regulatory Element (WPRE) followed by either a SV40 or human growth hormone (hGH) polyadenylation signal.

According to another aspect, the disclosure provides a host cell comprising the polynucleotide of any of the aspects or embodiments herein. According to some embodiments, the host cell is a mammalian cell. According to some embodiments, the host cell is a HEK-293 (293), Vero, RD, BHK-21, HT-1080, A549, Cos-7, ARPE-19, and MRC-5. According to some embodiments, the host cell is a BHK cell.

According to another aspect, the disclosure provides a recombinant herpes simplex virus (rHSV) comprising the polynucleotide of any one of the aspects or embodiments herein.

According to another aspect, the disclosure provides a transgene expression cassette comprising a polynucleotide of any one of the aspects and embodiments herein; and minimal regulatory elements.

According to another aspect, the disclosure provides a nucleic acid vector comprising the expression cassette of any of the aspects or embodiments herein. According to some embodiments, the vector is an adeno-associated viral (AAV) vector.

According to another aspect, the disclosure provides a host cell comprising the transgene expression cassette of any of the aspects or embodiments herein.

According to another aspect, the disclosure provides a kit comprising the expression vector of any of the aspects or embodiments herein and instructions for use.

An expression vector comprising the polynucleotide of any of the aspects or embodiments herein. According to some embodiments, the vector is an adeno-associated vital (AAV) vector. According to some embodiments, the serotype of the capsid sequence and the serotype of the ITRs of said AAV vector are independently selected from the group consisting of AAV1, AAV2, AAV3, AAV4, AAV5, AAV6, AAV7, AAV8, AAV9, AAV10, AAV11, and AAV12.

According to another aspect, the disclosure provides a recombinant adeno-associated (rAAV) expression vector comprising the polynucleotide of any of the aspects or embodiments herein, and an AAV genomic cassette. According to some embodiments, the AAV genomic cassette is flanked by two sequence-modulated inverted terminal repeats, preferably about 143-bases in length. According to some embodiments, the AAV genomic cassette is flanked by a self-complimentary AAV (scAAV) genomic cassette consisting of two inverted identical repeats, preferably no longer than 2.4 kb, separated by an about 113-bases scAAV-enabling ITR (ITRΔtrs) and flanked on either end by about 143-bases sequence-modulated ITRs. According to some embodiments, the expression vector further comprises a protein capsid variant optimally suited for cochlear delivery.

According to another aspect, the disclosure provides a recombinant adeno-associated (rAAV) expression vector comprising the polynucleotide of any of the aspects or embodiments herein, optionally a codon/sequence-optimized human GJB2 cDNA with or without a hemagglutinin C-terminal tag, preferably about 27-nucleotide in length, optionally about a 0.68 kilobase (kb) in size; operably linked to one of the following promoter elements optimized to drive high GJB2 expression: (a) an ubiquitously-active CBA, preferably about 1.7 kb in size, small CBA (smCBA), preferably about 0.96 kb in size, EF1a, preferably about 0.81 kb in size, or CASI promoter, preferably about 1.06 kb in size; (b) a cochlear-support cell or GJB2 expression-specific GFAP promoter, preferably about 1.68 kb in size, small GJB2 promoter, preferably about 0.13 kb in size, medium GJB2 promoter, preferably about 0.54 kb in size, large GJB2 promoter, preferably about 1.0 kb in size, or a sequential combination of 2-3 individual GJB2 expression-specific promoters; operably linked to a 0.9 kb 3'-UTR regulatory region comprising the Woodchuck Hepatitis Virus Posttranscriptional Regulatory Element (WPRE) followed by either a SV40 or human growth hormone (hGH) polyadenylation signal, further comprising either two about 143-base sequence-modulated inverted terminal repeats (ITRs) flanking the AAV genomic cassette or a self-complimentary AAV (scAAV) genomic cassette consisting of two inverted identical repeats, preferably no longer than 2.4 kb, separated by an about 113-base scAAV-enabling ITR (ITRΔtrs) and flanked on either end by about 143-base sequence-modulated ITRs; and a protein capsid variant suitable for targeted cochlear delivery. According to some embodiments, the polyadenylation signal is a SV40 or human growth hormone (hGH) polyadenylation signal. According to some embodiments, the promoter is optimized to drive high GJB2 expression. According to some embodiments, the rAAV is a serotype selected from the group consisting of AAV1, AAV2, AAV3, AAV4, AAV5, AAV6, AAV7, AAV8, AAV9, rh-AAV10, AAV10, AAV11, and AAV12. According to some embodiments, the rAAV is serotype AAV1. According to some embodiments, the rAAV is serotype AAV2. According to some embodiments, the rAAV is serotype AAV3. According to some embodiments, the rAAV is serotype AAV4. According to some embodiments, the rAAV is serotype AAV5. According to some embodiments, the rAAV is serotype AAV6. According to some embodiments, the rAAV is serotype AAV7. According to some embodiments, the rAAV is serotype AAV8. According to some embodiments, the rAAV is serotype AAV9. According to some embodiments, the rAAV is serotype rh-AAV10. According to some embodiments, the rAAV is serotype AAV10. According to some embodiments, the rAAV is serotype AAV11. According to some embodiments, the rAAV is serotype AAV12. According to some embodiments, the rAAV is comprised within an AAV virion.

According to another aspect, the disclosure provides a recombinant herpes simplex virus (rHSV) comprising the expression vector of any of any of the aspects or embodiments herein.

According to another aspect, the disclosure provides a polynucleotide comprising in the following order CBA-GJB2(X)-HA-WPRE-pA, where X comprises a nucleic acid sequence at least 85% identical to SEQ ID NO: 18. According to another aspect, the disclosure provides a polynucleotide comprising in the following order CBA-GJB2(X)-HA-WPRE-pA, where X comprises a nucleic acid sequence at least 90% identical to SEQ ID NO: 18. According to another aspect, the disclosure provides a polynucleotide comprising in the following order CBA-GJB2(X)-HA-WPRE-pA, where X comprises a nucleic acid sequence at least 95% identical to SEQ ID NO: 18. According to another aspect, the disclosure provides a polynucleotide comprising in the following order CBA-GJB2(X)-HA-WPRE-pA, where X comprises a nucleic acid sequence consisting of SEQ ID NO: 18.

According to another aspect, the disclosure provides a host cell comprising the expression vector of any of any of the aspects or embodiments herein. According to some embodiments, the host cell is a mammalian cell. According to some embodiments, the host cell is a HEK-293 (293), Vero, RD, BHK-21, HT-1080, A549, Cos-7, ARPE-19, and MRC-5. According to some embodiments, the host cell is a BHK cell.

According to another aspect, the disclosure provides a transgene expression cassette comprising the polynucleotide of any one of the aspects or embodiments herein; and minimal regulatory elements. According to another aspect, the disclosure provide nucleic acid vector comprising the expression cassette of any of the aspects and embodiments herein. According to some embodiments, the vector is an adeno-associated viral (AAV) vector.

According to another aspect, the disclosure provides a kit comprising the expression vector of any of the aspects and embodiments herein and instructions for use.

According to another aspect, the disclosure provides a composition comprising the polynucleotide of any of the aspects and embodiments herein.

According to another aspect, the disclosure provides a composition comprising the host cell of any of the aspects and embodiments herein.

According to another aspect, the disclosure provides a composition comprising the recombinant herpes simplex virus (rHSV) of any of the aspects and embodiments herein.

According to another aspect, the disclosure provides a composition comprising the transgene expression cassette of any of the aspects and embodiments herein.

According to another aspect, the disclosure provides a composition comprising the expression vector of any of the aspects and embodiments herein. According to some embodiments, the composition is a pharmaceutical composition.

According to another aspect, the disclosure provides a method of treating genetic hearing loss comprising administering the polynucleotide of any one of any of the aspects and embodiments herein to a subject in need thereof.

According to another aspect, the disclosure provides a method of preventing genetic hearing loss comprising administering the polynucleotide of any one of any of the aspects and embodiments herein to a subject in need thereof.

According to another aspect, the disclosure provides a method of treating or preventing genetic hearing loss comprising administering the transgene expression cassette of any of the aspects and embodiments herein to a subject in need thereof.

According to another aspect, the disclosure provides a method of treating or preventing genetic hearing loss comprising administering the expression vector of any of the aspects and embodiments herein to a subject in need thereof.

According to another aspect, the disclosure provides a method of treating or preventing genetic hearing loss comprising administering the recombinant adeno-associated (rAAV) expression vector of any of the aspects and embodiments herein to a subject in need thereof.

According to another aspect, the disclosure provides a method of treating or preventing genetic hearing loss comprising administering a recombinant adeno-associated (rAAV) viral particle comprising the polynucleotide of any of the aspects and embodiments herein to a subject in need thereof. According to some embodiments, the genetic hearing loss is DFNB1 hearing loss. According to some embodiments, the genetic hearing loss is caused by a mutation in GJB2. According to some embodiments, the genetic hearing loss is caused by an autosomal recessive GJB2 mutants (DFNB1). According to some embodiments, the genetic hearing loss is caused by an autosomal dominant GJB2 mutants (DFNA3A). According to some embodiments, the administration is to the cochlea. According to some embodiments, the administration is intravenous, intracerebroventricular, intracochlear, intrathecal, or a combination thereof.

According to some embodiments of the aspects and embodiments herein, the subject is a child. According to some embodiments, the subject is an infant.

According to another aspect, the disclosure provides a method for producing recombinant AAV viral particles comprising: co-infecting a suspension a cell with a first recombinant herpesvirus comprising a nucleic acid encoding an AAV rep and an AAV cap gene each operably linked to a promoter; and a second recombinant herpesvirus comprising a GJB2 gene, and a promoter operably linked to said gene; and allowing the cell to produce the recombinant AAV viral particles, thereby producing the recombinant AAV viral particles. According to some embodiments, the cell is HEK-293 (293), Vero, RD, BHK-21, HT-1080, A549, Cos-7, ARPE-19, and MRC-5. According to some embodiments, the cell is infected at a combined multiplicity of infection (MOI) of between 3 and 14. According to some embodiments, the cap gene is selected from an AAV with a serotype selected from the group consisting of AAV1, AAV2, AAV3, AAV4, AAV5, AAV6, AAV7, AAV8, AAV9, rh-AAV10, AAV11, and AAV12. According to some embodiments, the first herpesvirus and the second herpesvirus are viruses selected from the group consisting of: cytomegalovirus (CMV), herpes simplex (HSV) and varicella zoster (VZV) and epstein barr virus (EBV). According to some embodiments, the herpesvirus is replication defective. According to some embodiments, the co-infection is simultaneous.

BRIEF DESCRIPTION OF THE DRAWINGS

FIG. 2 shows a schematic of GJB2 vector (genome) construct single stranded (ss)AAV-GJB2 and self-complementary scAAV-GJB2.

FIG. 3 shows the nucleic acid sequence of the CBA promoter (SEQ ID NO. 1).

FIG. 4 shows the nucleic acid sequence of the EF1a promoter (SEQ ID NO. 2).

FIG. 5 shows the nucleic acid sequence of the CAST promoter (SEQ ID NO. 3).

FIG. 6 shows the nucleic acid sequence of the smCBA promoter (SEQ ID NO. 4).

FIG. 7 shows the nucleic acid sequence of the GFAP promoter (SEQ ID NO. 5).

FIG. 8 shows the nucleic acid sequence of the GJB2 (1000) promoter (SEQ ID NO. 6). GJB2(128) is underlined, GJB2(539) is bolded.

FIG. 9 shows the nucleic acid sequences of the following ITRs (AAV2) 5'-3': for single stranded (ss) and self-complimentary (sc) AAV genomes (SEQ ID NO. 7); 3'-5': for single stranded (ss) AAV genomes only (SEQ ID NO. 8); 3'-5': for self-complimentary (sc) AAV genomes only (SEQ ID NO. 9).

FIG. 10 shows the nucleic acid sequence of human wild-type GJB2 (hGJB2wt) (SEQ ID NO. 10).

FIG. 11 shows the nucleic acid sequence of human codon optimized GJB2 (hGJB2co3) (SEQ ID NO. 11).

FIG. 12 shows the nucleic acid sequence of human codon optimized GJB2 (hGJB2co6) (SEQ ID NO. 12).

FIG. 13 shows the nucleic acid sequence of human codon optimized GJB2 (hGJB2co9) (SEQ ID NO. 13).

FIG. 14 shows the nucleic acid sequence of a hemagglutinin (HA) tag (SEQ ID NO. 14).

FIG. 15 shows the nucleic acid sequence of a Woodchuck Hepatitis Virus Posttranscriptional Regulatory Element (WPRE) (SEQ ID NO. 15).

FIG. 16 shows the nucleic acid sequence of SV40 poly(A) (SEQ ID NO. 16).

FIG. 17 shows the nucleic acid sequence of a SV40/bGH terminator sequence (SEQ ID NO. 17).

FIG. 18A shows the nucleic acid sequence of the hybrid codon optimized construct (co369GJB2) (SEQ ID NO. 18). FIG. 18B shows the amino acid sequence of the hybrid codon optimized construct (co369GJB2) (SEQ ID NO. 19).

FIG. 19A shows a summary of GFP transduction in rodent cochlea.

FIG. 19C discloses SEQ ID NOS 20-32, respectively, in order of appearance.

FIG. 22 depicts schematics of the codon optimized constructs (AAV-CBA-GJB2(X)-HA-WPRE-pA.

FIG. 25 shows a sequence alignment of hGJB2co9 (SEQ ID NO: 34) compared to WT (hGJB2) (SEQ ID NO: 33).

FIG. 26 shows an alignment between the GJB2 WT (SEQ ID NO: 36), co3 (SEQ ID NO: 37), co6 (SEQ ID NO: 38) and co9 (SEQ ID NO: 39) sequences, the consensus sequence (SEQ ID NO: 35) that was determined from the alignment, and the co369 hybrid codon optimized sequence.

FIG. 29 discloses SEQ ID NOS 40-43, respectively, in order of appearance.

DETAILED DESCRIPTION OF THE INVENTION

Definitions

Figure 1A:
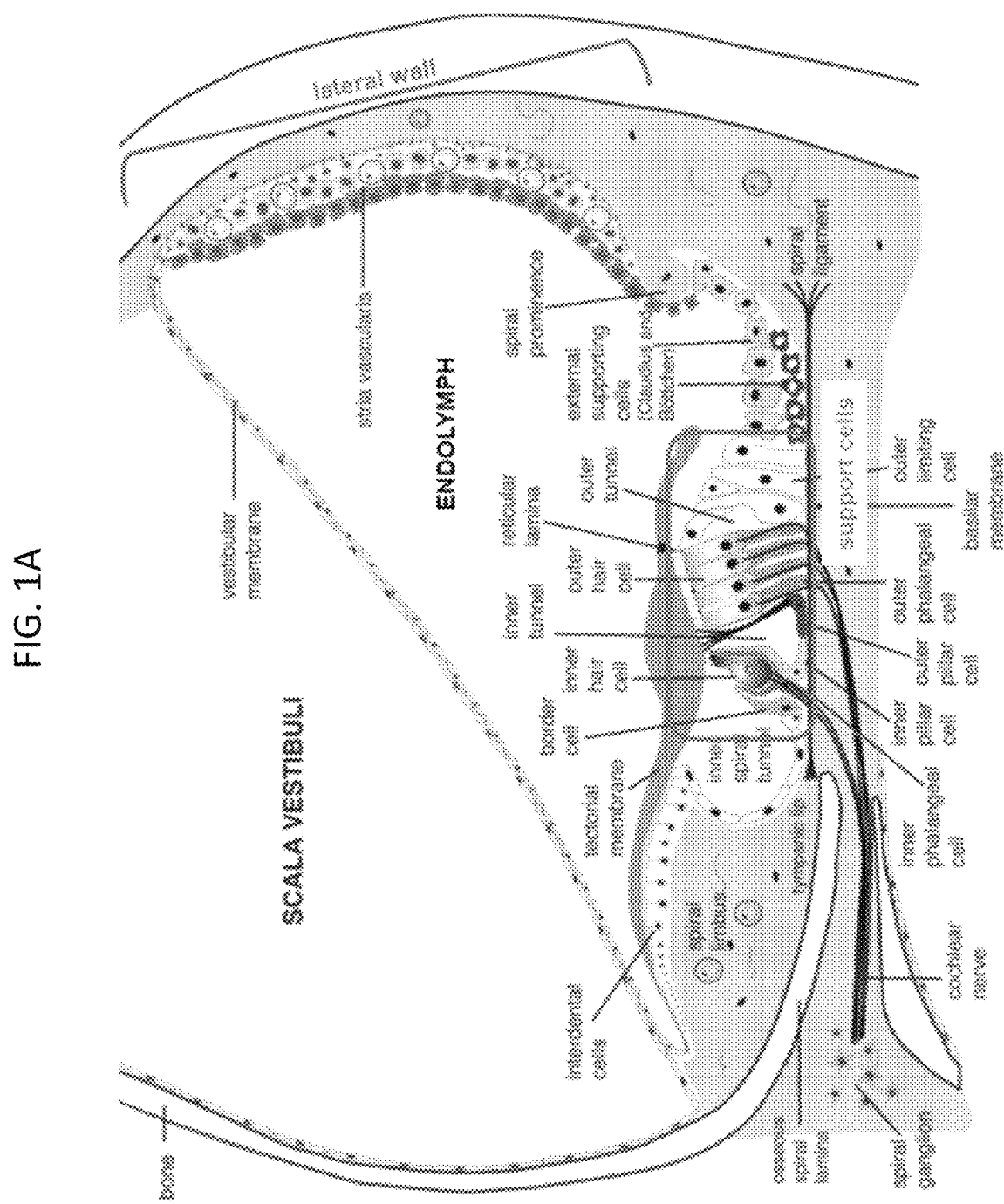
FIG. 1A is a schematic of cochlear anatomy and cell types.
Figure 1B:
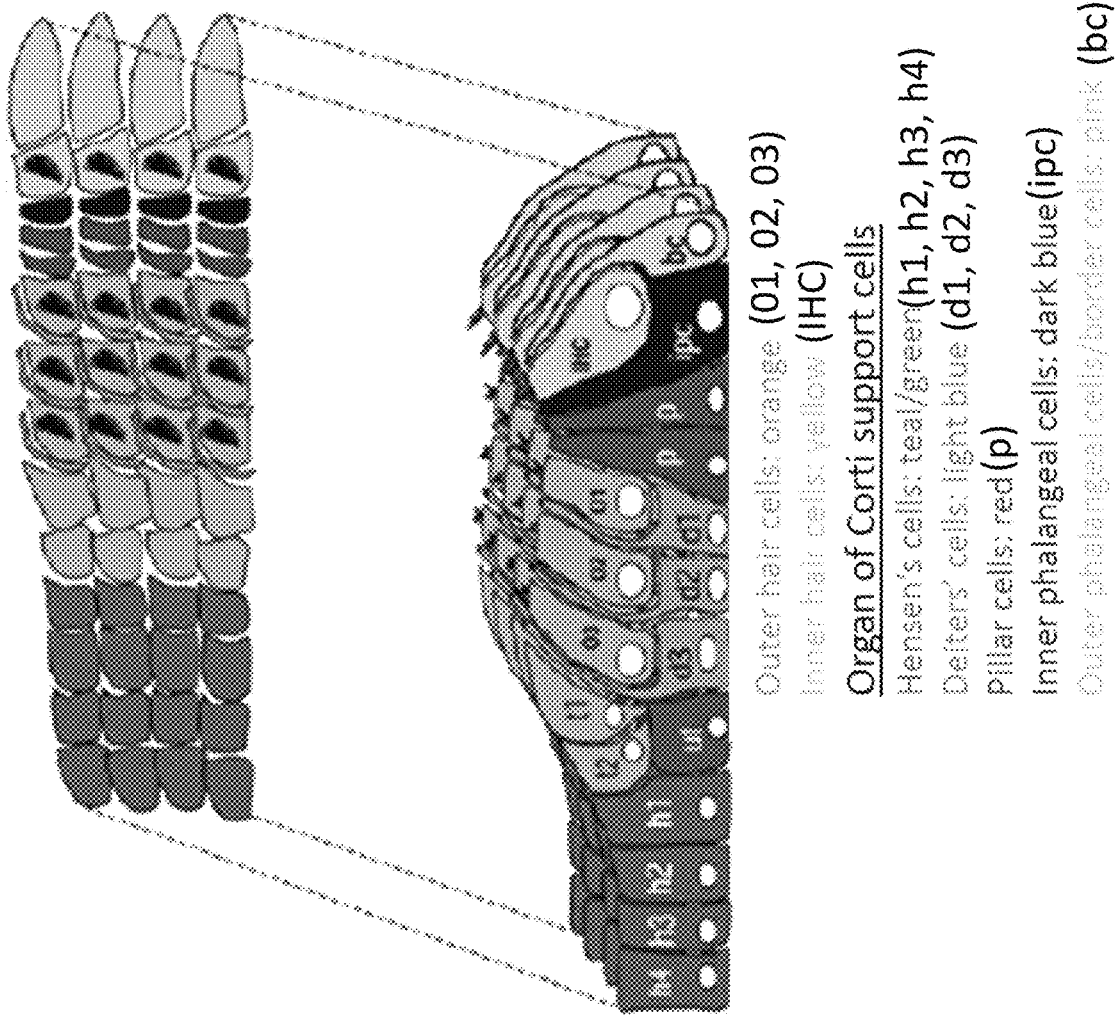
FIG. 1B shows a close up of the support cells. Shown are outer hair cells (01, 02, 03), inner hair cells (IHC), hensen's cells (h1, h2, h3, h4), deiters' cells (d1, d2, d3), pillar cells (p), inner phalangeal cells (IPC), outer phalangeal cells/border cells (bc).

Unless defined otherwise, all technical and scientific terms used herein have the meaning commonly understood by a person skilled in the art to which this invention belongs. The following references provide one of skill with a general definition of many of the terms used in this invention. Singleton et al. Dictionary of Microbiology and Molecular Biology (2$^{nd}$ Ed. 1994); The Cambridge Dictionary of Science and Technology (Walker ed., 1988); The Glossary of Genetics, 5th Ed., R. Rieger et al. (Eds.), Springer Verlag (1991); and Hale & Marham, The Harper Collins Dictionary of Biology (1991). As used herein, the following terms have the meanings ascribed to them below, unless specified otherwise.

As used herein, the terms "administer," "administering," "administration," and the like, are meant to refer to methods that are used to enable delivery of therapeutics or pharmaceutical compositions to the desired site of biological action.

As used herein, the term "AAV virion" is meant to refer broadly to a complete virus particle, such as for example a wild type AAV virion particle, which comprises single stranded genome DNA packaged into AAV capsid proteins. The single stranded nucleic acid molecule is either sense strand or antisense strand, as both strands are equally infectious. The term "rAAV viral particle" refers to a recombinant AAV virus particle, i.e., a particle that is infectious but replication defective. A rAAV viral particle comprises single stranded genome DNA packaged into AAV capsid proteins.

As used herein, the term "bioreactor" is meant to refer broadly to any apparatus that can be used for the purpose of culturing cells.

As used herein, the term "carrier" is meant to include any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutically active substances is well known in the art.

Supplementary active ingredients can also be incorporated into the compositions. The phrase "pharmaceutically-acceptable" refers to molecular entities and compositions that do not produce a toxic, an allergic, or similar untoward reaction when administered to a host.

As used herein, the terms "gene" or "coding sequence," is meant to refer broadly to a DNA region (the transcribed region) which encodes a protein. A coding sequence is transcribed (DNA) and translated (RNA) into a polypeptide when placed under the control of an appropriate regulatory region, such as a promoter. A gene may comprise several operably linked fragments, such as a promoter, a 5'-leader sequence, a coding sequence and a 3'-non-translated sequence, comprising a polyadenylation site. The phrase "expression of a gene" refers to the process wherein a gene is transcribed into an RNA and/or translated into an active protein.

The term "flanking" refers to a relative position of one nucleic acid sequence with respect to another nucleic acid sequence. Generally, in the sequence ABC, B is flanked by A and C. The same is true for the arrangement A×B×C. Thus, a flanking sequence precedes or follows a flanked sequence but need not be contiguous with, or immediately adjacent to the flanked sequence.

As used herein, the term "functional variant of a gene" includes a variant of the gene with minor variations such as, for example, silent mutations, single nucleotide polymorphisms, missense mutations, and other mutations or deletions that do not significantly alter gene function.

As used herein, the term "gene delivery" means a process by which foreign DNA is transferred to host cells for applications of gene therapy.

As used herein, the term "gene of interest (GOI)," as used herein refers broadly to a heterologous sequence introduced into an AAV expression vector, and typically refers to a nucleic acid sequence encoding a protein of therapeutic use in humans or animals.

As used herein, the term "hearing loss" is meant to refer to a diminished sensitivity to the sounds normally heard by a subject. The severity of a hearing loss is categorized according to the increase in volume above the usual level necessary before the listener can detect it. According to some embodiments, hearing loss may be characterized by increases in the threshold volume at which an individual perceives tones at different frequencies.

As used herein, the terms "herpesvirus" or "herpesviridae family, are meant to refer broadly to the general family of enveloped, double-stranded DNA viruses with relatively large genomes. The family replicates in the nucleus of a wide range of vertebrate and invertebrate hosts, in preferred embodiments, mammalian hosts, for example in humans, horses, cattle, mice, and pigs. Exemplary members of the herpesviridae family include cytomegalovirus (CMV), herpes simplex virus types 1 and 2 (HSV1 and HSV2) and varicella zoster (VZV) and Epstein Barr Virus (EBV).

As used herein, the term "heterologous," means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector is a heterologous nucleotide sequence with respect to the vector.

As used herein, the term "increase," "enhance," "raise" (and like terms) generally refers to the act of increasing, either directly or indirectly, a concentration, level, function, activity, or behavior relative to the natural, expected, or average, or relative to a control condition.

As used herein, the term "infection," is meant to refer broadly to delivery of heterologous DNA into a cell by a virus. The term "co-infection" as used herein means "simultaneous infection," "double infection," "multiple infection," or "serial infection" with two or more viruses. Infection of a producer cell with two (or more) viruses will be referred to as "co-infection." The term "transfection" refers to a process of delivering heterologous DNA to a cell by physical or chemical methods, such as plasmid DNA, which is transferred into the cell by means of electroporation, calcium phosphate precipitation, or other methods well known in the art.

As used herein, the term "inner ear cells" or "cells of the inner ear" refers to inner hair cells (IHCs) and outer hair cells (OHCs), spiral ganglion neurons, vestibular hair cells, vestibular ganglion neurons, supporting cells and cells in the stria vascularis. Supporting cells refer to cells in the ear that are not excitable, e.g., cells that are not hair cells or neurons.

As used herein, the term "inverted terminal repeat" or "ITR" sequence is meant to refer to relatively short sequences found at the termini of viral genomes which are in opposite orientation. An "AAV inverted terminal repeat (ITR)" sequence, a term well-understood in the art, is an approximately 145-nucleotide sequence that is present at both termini of the native single-stranded AAV genome. The outermost nucleotides of the ITR can be present in either of two alternative orientations, leading to heterogeneity between different AAV genomes and between the two ends of a single AAV genome.

A "wild-type ITR", "WT-ITR" or "ITR" refers to the sequence of a naturally occurring ITR sequence in an AAV or other *Dependovirus* that retains, e.g., Rep binding activity and Rep nicking ability. The nucleotide sequence of a WT-ITR from any AAV serotype may slightly vary from the canonical naturally occurring sequence due to degeneracy of the genetic code or drift, and therefore WT-ITR sequences encompassed for use herein include WT-ITR sequences as result of naturally occurring changes taking place during the production process (e.g., a replication error). According to some embodiments, the ITR is WT AAV2 ITR.

As used herein, the term "terminal repeat" or "TR" includes any viral terminal repeat or synthetic sequence that comprises at least one minimal required origin of replication and a region comprising a palindrome hairpin structure. A Rep-binding sequence ("RBS") (also referred to as RBE (Rep-binding element)) and a terminal resolution site ("TRS") together constitute a "minimal required origin of replication" and thus the TR comprises at least one RBS and at least one TRS. TRs that are the inverse complement of one another within a given stretch of polynucleotide sequence are typically each referred to as an "inverted terminal repeat" or "ITR". In the context of a virus, ITRs mediate replication, virus packaging, integration and provirus rescue.

The term "in vivo" refers to assays or processes that occur in or within an organism, such as a multicellular animal. In some of the aspects described herein, a method or use can be said to occur "in vivo" when a unicellular organism, such as a bacterium, is used. The term "ex vivo" refers to methods and uses that are performed using a living cell with an intact membrane that is outside of the body of a multicellular animal or plant, e.g., explants, cultured cells, including primary cells and cell lines, transformed cell lines, and extracted tissue or cells, including blood cells, among others. The term "in vitro" refers to assays and methods that do not require the presence of a cell with an intact membrane, such as cellular extracts, and can refer to the introducing of a programmable synthetic biological circuit in a non-cellular system, such as a medium not comprising cells or cellular systems, such as cellular extracts.

As used herein, the term "isolated" molecule (e.g., an isolated nucleic acid or protein or cell) means it has been identified and separated and/or recovered from a component of its natural environment.

As used herein, the term "middle-ear" is meant to refer to the space between the tympanic membrane and the inner ear.

As used herein, the term "minimal regulatory elements" is meant to refer to regulatory elements that are necessary for effective expression of a gene in a target cell and thus should be included in a transgene expression cassette. Such sequences could include, for example, promoter or enhancer sequences, a polylinker sequence facilitating the insertion of a DNA fragment within a plasmid vector, and sequences responsible for intron splicing and polyadenylation of mRNA transcripts.

As used herein, the term "minimize", "reduce", "decrease," and/or "inhibit" (and like terms) generally refers to the act of reducing, either directly or indirectly, a concentration, level, function, activity, or behavior relative to the natural, expected, or average, or relative to a control condition.

As used herein, the term "non-naturally occurring" is meant to refer broadly to a protein, nucleic acid, ribonucleic acid, or virus that does not occur in nature. For example, it may be a genetically modified variant, e.g., cDNA or codon-optimized nucleic acid.

As used herein, a "nucleic acid" or a "nucleic acid molecule" is meant to refer to a molecule composed of chains of monomeric nucleotides, such as, for example, DNA molecules (e.g., cDNA or genomic DNA). A nucleic acid may encode, for example, a promoter, the GJB2 gene or portion thereof, or regulatory elements. A nucleic acid molecule can be single-stranded or double-stranded. A "GJB2 nucleic acid" refers to a nucleic acid that comprises the GJB2 gene or a portion thereof, or a functional variant of the GJB2 gene or a portion thereof. A functional variant of a gene includes a variant of the gene with minor variations such as, for example, silent mutations, single nucleotide polymorphisms, missense mutations, and other mutations or deletions that do not significantly alter gene function.

The asymmetric ends of DNA and RNA strands are called the 5' (five prime) and 3' (three prime) ends, with the 5' end having a terminal phosphate group and the 3' end a terminal hydroxyl group. The five prime (5') end has the fifth carbon in the sugar-ring of the deoxyribose or ribose at its terminus. Nucleic acids are synthesized in vivo in the 5'- to 3'-direction, because the polymerase used to assemble new strands attaches each new nucleotide to the 3'-hydroxyl (—OH) group via a phosphodiester bond.

The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present disclosure.

A DNA sequence that "encodes" a particular GJB2 protein is a nucleic acid sequence that is transcribed into the particular RNA and/or protein. A DNA polynucleotide may encode an RNA (mRNA) that is translated into protein, or a DNA polynucleotide may encode an RNA that is not translated into protein (e.g., tRNA, rRNA, or a DNA-targeting RNA; also called "non-coding" RNA or "ncRNA").

As used herein, the terms "operatively linked" or "operably linked" or "coupled" can refer to a juxtaposition of genetic elements, wherein the elements are in a relationship permitting them to operate in an expected manner. For instance, a promoter can be operatively linked to a coding region if the promoter helps initiate transcription of the coding sequence. There may be intervening residues between the promoter and coding region so long as this functional relationship is maintained.

As used herein, a "percent (%) sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various ways that are within the skill in the art, for instance, using publicly available computer software programs, for example, those described in Current Protocols in Molecular Biology (Ausubel et al., eds., 1987), Supp. 30, section 7.7.18, Table 7.7.1, and including BLAST, BLAST-2, ALIGN or Megalign (DNASTAR) software. An example of an alignment program is ALIGN Plus (Scientific and Educational Software, Pennsylvania). Those skilled in the art can determine appropriate parameters for measuring alignment, including any algorithms needed to achieve maximal alignment over the full length of the sequences being compared. For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z, where W is the number of nucleotides scored as identical matches by the sequence alignment program in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

As used herein, the term "pharmaceutical composition" or "composition" is meant to refer to a composition or agent described herein (e.g. a recombinant adeno-associated (rAAV) expression vector), optionally mixed with at least one pharmaceutically acceptable chemical component, such as, though not limited to, carriers, stabilizers, diluents, dispersing agents, suspending agents, thickening agents, excipients and the like.

As used herein, the terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

As used herein, a "promoter" is meant to refer to a region of DNA that facilitates the transcription of a particular gene. As part of the process of transcription, the enzyme that synthesizes RNA, known as RNA polymerase, attaches to the DNA near a gene. Promoters contain specific DNA sequences and response elements that provide an initial binding site for RNA polymerase and for transcription factors that recruit RNA polymerase. According to some embodiments, the promoter is highly specific for support cell expression in the cochlea. According to some embodiments, the promoter is an endogenous GJB2 promoter. According to some embodiments, the promoter is selected from the group consisting of a CBA promoter, smCBA promoter, a CASI promoter, a GFAP promoter, and an elongation factor-1 alpha (EF1a) promoter. A "chicken beta-actin (CBA) promoter" refers to a polynucleotide sequence derived from a chicken beta-actin gene (e.g., *Gallus* beta actin, represented by GenBank Entrez Gene ID 396526). A "smCBA" promoter refers to the small version of the hybrid CMV-chicken beta-actin promoter. A "CASI" promoter refers to a promoter comprising a portion of the CMV enhancer, a portion of the chicken beta-actin promoter, and a portion of the UBC enhancer.

The term "enhancer" as used herein refers to a cis-acting regulatory sequence (e.g., 50-1,500 base pairs) that binds one or more proteins (e.g., activator proteins, or transcription factor) to increase transcriptional activation of a nucleic acid sequence. Enhancers can be positioned up to 1,000,000 base pars upstream of the gene start site or downstream of the gene start site that they regulate.

A promoter can be said to drive expression or drive transcription of the nucleic acid sequence that it regulates. The phrases "operably linked," "operatively positioned," "operatively linked," "under control," and "under transcriptional control" indicate that a promoter is in a correct functional location and/or orientation in relation to a nucleic acid sequence it regulates to control transcriptional initiation and/or expression of that sequence. An "inverted promoter," as used herein, refers to a promoter in which the nucleic acid sequence is in the reverse orientation, such that what was the coding strand is now the non-coding strand, and vice versa. Inverted promoter sequences can be used in various embodiments to regulate the state of a switch. In addition, in various embodiments, a promoter can be used in conjunction with an enhancer.

A promoter can be one naturally associated with a gene or sequence, as can be obtained by isolating the 5' non-coding sequences located upstream of the coding segment and/or exon of a given gene or sequence. Such a promoter can be referred to as "endogenous." Similarly, in some embodiments, an enhancer can be one naturally associated with a nucleic acid sequence, located either downstream or upstream of that sequence.

In some embodiments, a coding nucleic acid segment is positioned under the control of a "recombinant promoter" or "heterologous promoter," both of which refer to a promoter that is not normally associated with the encoded nucleic acid sequence it is operably linked to in its natural environment. A recombinant or heterologous enhancer refers to an enhancer not normally associated with a given nucleic acid sequence in its natural environment. Such promoters or enhancers can include promoters or enhancers of other genes; promoters or enhancers isolated from any other prokaryotic, viral, or eukaryotic cell; and synthetic promoters or enhancers that are not "naturally occurring," i.e., comprise different elements of different transcriptional regulatory regions, and/or mutations that alter expression through methods of genetic engineering that are known in the art.

As used herein, the term "recombinant" can refer to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids.

As used herein, the term "recombinant HSV," "rHSV," and "rHSV vector," is meant to refer broadly to isolated, genetically modified forms of herpes simplex virus type 1 (HSV) containing heterologous genes incorporated into the viral genome. By the term "rHSV-rep2cap2" or "rHSV-rep2cap1" is meant an rHSV in which the AAV rep and cap genes from either AAV serotype 1 or 2 have been incorporated into the rHSV genome, in certain embodiments, a DNA sequence encoding a therapeutic gene of interest has been incorporated into the viral genome.

As used herein, a "subject" or "patient" or "individual" to be treated by the method of the invention is meant to refer to either a human or non-human animal. A "nonhuman animal" includes any vertebrate or invertebrate organism. A human subject can be of any age, gender, race or ethnic group, e.g., Caucasian (white), Asian, African, black, African American, African European, Hispanic, Mideastern, etc. In some embodiments, the subject can be a patient or other subject in a clinical setting. In some embodiments, the subject is already undergoing treatment. In some embodiments, the subject is a neonate, infant, child, adolescent, or adult.

As used herein the term "therapeutic effect" refers to a consequence of treatment, the results of which are judged to be desirable and beneficial. A therapeutic effect can include, directly or indirectly, the arrest, reduction, or elimination of a disease manifestation. A therapeutic effect can also include, directly or indirectly, the arrest reduction or elimination of the progression of a disease manifestation.

For any therapeutic agent described herein therapeutically effective amount may be initially determined from preliminary in vitro studies and/or animal models. A therapeutically effective dose may also be determined from human data. The applied dose may be adjusted based on the relative bioavailability and potency of the administered compound. Adjusting the dose to achieve maximal efficacy based on the methods described above and other well-known methods is within the capabilities of the ordinarily skilled artisan. General principles for determining therapeutic effectiveness, which may be found in Chapter 1 of Goodman and Gilman's The Pharmacological Basis of Therapeutics, 10th Edition, McGraw-Hill (New York) (2001), incorporated herein by reference, are summarized below.

As used herein, the term "transgene" is meant to refer to a polynucleotide that is introduced into a cell and is capable of being transcribed into RNA and optionally, translated and/or expressed under appropriate conditions. In aspects, it confers a desired property to a cell into which it was introduced, or otherwise leads to a desired therapeutic or diagnostic outcome.

As used herein, a "transgene expression cassette" or "expression cassette" are used interchangeably and refer to a linear stretch of nucleic acids that includes a transgene that is operably linked to one or more promoters or other regulatory sequences sufficient to direct transcription of the transgene, but which does not comprise capsid-encoding sequences, other vector sequences or inverted terminal repeat regions. An expression cassette may additionally comprise one or more cis-acting sequences (e.g., promoters, enhancers, or repressors), one or more introns, and one or more post-transcriptional regulatory elements.

As used herein, the terms "treatment" or "treating" a disease or disorder are meant to refer to alleviation of one or more signs or symptoms of the disease or disorder, diminishment of extent of disease or disorder, stabilized (e.g., not worsening) state of disease or disorder, preventing spread of disease or disorder, delay or slowing of disease or disorder progression, amelioration or palliation of the disease or disorder state, and remission (whether partial or total), whether detectable or undetectable. For example, GJB2, when expressed in an effective amount (or dosage) is sufficient to prevent, correct, and/or normalize an abnormal physiological response, e.g., a therapeutic effect that is sufficient to reduce by at least about 30 percent, more preferably by at least 50 percent, most preferably by at least 90 percent, a clinically significant feature of disease or disorder. "Treatment" can also refer to prolonging survival as compared to expected survival if not receiving treatment.

As used herein, the term "vector" is meant to refer to a recombinant plasmid or virus that comprises a nucleic acid to be delivered into a host cell, either in vitro or in vivo.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g., 5' untranslated (5'UTR) or "leader" sequences and 3' UTR or "trailer" sequences, as well as intervening sequences (introns) between individual coding segments (exons).

As used herein, the term "recombinant viral vector" is meant to refer to a recombinant polynucleotide vector comprising one or more heterologous sequences (i.e., nucleic acid sequence not of viral origin). In the case of recombinant AAV vectors, the recombinant nucleic acid is flanked by at least one inverted terminal repeat sequence (ITR). In some embodiments, the recombinant nucleic acid is flanked by two ITRs.

As used herein, the term "recombinant AAV vector (rAAV vector)" is meant to refer to a polynucleotide vector comprising one or more heterologous sequences (i.e., nucleic acid sequence not of AAV origin) that are flanked by at least one AAV inverted terminal repeat sequence (ITR). Such rAAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). When a rAAV vector is incorporated into a larger polynucleotide (e.g., in a chromosome or in another vector such as a plasmid used for cloning or transfection), then the rAAV vector may be referred to as a "pro-vector" which can be "rescued" by replication and encapsidation in the presence of AAV packaging functions and suitable helper functions. A rAAV vector can be in any of a number of forms, including, but not limited to, plasmids, linear artificial chromosomes, complexed with lipids, encapsulated within liposomes, and encapsidated in a viral particle, e.g., an AAV particle. A rAAV vector can be packaged into an AAV virus capsid to generate a "recombinant adeno-associated viral particle (rAAV particle)".

As used herein, the term a "rAAV virus" or "rAAV viral particle" is meant to refer to a viral particle composed of at least one AAV capsid protein and an encapsidated rAAV vector genome.

As used herein, "reporters" refer to proteins that can be used to provide detectable read-outs. Reporters generally produce a measurable signal such as fluorescence, color, or luminescence. Reporter protein coding sequences encode proteins whose presence in the cell or organism is readily observed. For example, fluorescent proteins cause a cell to fluoresce when excited with light of a particular wavelength, luciferases cause a cell to catalyze a reaction that produces light, and enzymes such as β-galactosidase convert a substrate to a colored product. Exemplary reporter polypeptides useful for experimental or diagnostic purposes include, but are not limited to β-lactamase, β-galactosidase (LacZ), alkaline phosphatase (AP), thymidine kinase (TK), green fluorescent protein (GFP) and other fluorescent proteins, chloramphenicol acetyltransferase (CAT), luciferase, and others well known in the art.

Transcriptional regulators refer to transcriptional activators and repressors that either activate or repress transcription of a gene of interest, such as GJB2. Promoters are regions of nucleic acid that initiate transcription of a particular gene Transcriptional activators typically bind nearby to transcriptional promoters and recruit RNA polymerase to directly initiate transcription. Repressors bind to transcriptional promoters and sterically hinder transcriptional initiation by RNA polymerase. Other transcriptional regulators may serve as either an activator or a repressor depending on where they bind and cellular and environmental conditions. Non-limiting examples of transcriptional regulator classes include, but are not limited to homeodomain proteins, zinc-finger proteins, winged-helix (forkhead) proteins, and leucine-zipper proteins.

As used herein, a "repressor protein" or "inducer protein" is a protein that binds to a regulatory sequence element and represses or activates, respectively, the transcription of sequences operatively linked to the regulatory sequence element. Preferred repressor and inducer proteins as described herein are sensitive to the presence or absence of at least one input agent or environmental input. Preferred proteins as described herein are modular in form, comprising, for example, separable DNA-binding and input agent-binding or responsive elements or domains.

As used herein the term "comprising" or "comprises" is used in reference to compositions, methods, and respective component(s) thereof, that are essential to the method or composition, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The term "including" is used herein to mean, and is used interchangeably with, the phrase "including but not limited to."

The term "such as" is used herein to mean, and is used interchangeably, with the phrase "such as but not limited to."

As used in this specification and the appended claims, the singular forms "a," "an," and "the" include plural references unless the context clearly dictates otherwise. Thus, for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Nucleic Acids

The characterization and development of nucleic acid molecules for potential therapeutic use are provided herein. As described herein, the nucleic acids for therapeutic use encode a GJB2 protein, wherein the nucleic acids are codon optimized.

The present disclosure provides promoters, expression cassettes, vectors, kits, and methods that can be used in the treatment of hereditary hearing impairment. Certain aspects of the disclosure relate to delivering a heterologous nucleic acid to cells of the inner ear of a subject comprising administering a recombinant adeno-associated virus (rAAV) vector. According to some aspects, the disclosure provides methods of treating or preventing genetic hearing loss comprising delivery of a composition comprising rAAV vectors described herein to the subject, wherein the rAAV vector comprises a heterologous nucleic acid (e.g. a nucleic acid encoding GJB2).

The gene most commonly mutated among subjects with hereditary hearing impairment (HI), GJB2, encodes the connexin-26 (Cx26) gap junction channel protein that underlies both intercellular communication among supporting cells and homeostasis of the cochlear fluids, endolymph and perilymph. GJB2 lies at the DFNB1 locus on 13q12. GJB2 is 5513 bp long and contains two exons (193 bp and 2141 bp long, respectively) separated by a 3179-bp intron (Kiang et al., 1997). Transcription is initiated from a single start site and leads to the synthesis of a 2334-nucleotide mRNA (GenBank NM_004004.5), which is considered canonical. Loss of GJB2 causes massive cell death of various cell types in the inner ear following onset of hearing. A "GJB2 nucleic acid" refers to a nucleic acid that comprises the GJB2 gene or a portion thereof, or a functional variant of the GJB2 gene or a portion thereof.

Accordingly, in some embodiments, the AAV vector is used for expression of GJB2 protein to restore hearing.

According to some embodiments, the gene of interest (e.g., GJB2) is optimized to be superior in expression (and/or function) to wildtype GJB2, and further has the ability to discriminate (at the DNA/RNA level) from wild-type GJB2.

According to some embodiments, the present disclosure provides GJB2 therapeutic proteins or fragments thereof (e.g., functional fragments) that are encoded by codon optimized nucleic acids and expressed in and from an AAV vector as described herein. One of skill in the art will understand that the GJB2 therapeutic protein includes all splice variants and orthologs of the GJB2 protein. The GJB2 therapeutic protein includes intact molecules as well as truncated fragments (e.g., functional) thereof.

FIG. 2 shows a schematic of GJB2 vector (genome) construct single stranded (ss)AAV-GJB2 and self-complementary scAAV-GJB2.

According to some embodiments, the disclosure provides a nucleic acid encoding a wild-type GJB2 protein. According to some embodiments, the disclosure provides a nucleic acid encoding a human wild-type GJB2 protein. According to some embodiments, the nucleic acid sequence encoding the human wild-type GJB2 protein is 678 bp in length. According to one embodiment, the nucleic acid encoding the human wild-type GJB2 protein comprises SEQ ID NO: 10. According to one embodiment, the nucleic acid is at least 85% identical to SEQ ID NO: 10. According to one embodiment, the nucleic acid is at least 90% identical to SEQ ID NO: 10. According to one embodiment, the nucleic acid is at least 95% identical to SEQ ID NO: 10. According to one embodiment, the nucleic acid is at least 99% identical to SEQ ID NO: 10. According to one embodiment, the nucleic acid consists of SEQ ID NO: 10.

FIG. 10 shows the nucleic acid sequence of the human wild-type GJB2 (hGJB2wt) (SEQ ID NO. 10).

According to some embodiments, the disclosure provides a nucleic acid encoding a GJB2 protein, wherein the nucleic acid sequence is codon optimized for mammalian expression. The human codon optimized GJB2 is an important element that codes for a major gap junction protein that is required for normal hearing. Codon optimization is performed to enhance protein expression of GJB2.

As used herein, the term "codon optimized" or "codon optimization" refers to the process of modifying a nucleic acid sequence for enhanced expression in the cells of the vertebrate of interest, e.g., mouse or human, by replacing at least one, more than one, or a significant number of codons of the native sequence (e.g., a prokaryotic sequence) with codons that are more frequently or most frequently used in the genes of that vertebrate. Various species exhibit particular bias for certain codons of a particular amino acid.

Typically, codon optimization does not alter the amino acid sequence of the original translated protein. Optimized codons can be determined using various commercially available platforms (e.g., Genscripts's OPTIMUMGENE, Atum's GENE GPS or Blue Heron Biotech's codon optimization tool) or another publicly available database. In some embodiments, the nucleic acid encoding the GJB2 protein is optimized for human expression, and/or is a human GJB2, or a functional fragment thereof. Exemplary GJB2 codon optimized sequences are disclosed herein.

According to some embodiments, the disclosure provides a nucleic acid encoding a human codon optimized GJB2 protein. According to some embodiments, the expressed GJB2 therapeutic protein is functional for the treatment of genetic hearing loss, including the treatment and/or prevention of DFNB1 and DFNA3A-associated congenital deafness. In some embodiments, GJB2 therapeutic protein does not cause an immune system reaction.

According to some embodiments, the nucleic acid sequence encoding a human codon optimized GJB2 protein is 678 bp in length. According to one embodiment, the nucleic acid encoding the human codon optimized GJB2 protein comprises SEQ ID NO: 11. According to one embodiment, the nucleic acid is at least 85% identical to SEQ ID NO: 11. According to one embodiment, the nucleic acid is at least 90% identical to SEQ ID NO: 11. According to one embodiment, the nucleic acid is at least 95% identical to SEQ ID NO: 11. According to one embodiment, the nucleic acid is at least 99% identical to SEQ ID NO: 11. According to one embodiment, the nucleic acid consists of SEQ ID NO: 11.

FIG. 11 shows the nucleic acid sequence of the human codon optimized GJB2 (hGJB2co3) (SEQ ID NO. 11).

According to some embodiments, the nucleic acid sequence encoding a human codon optimized GJB2 protein is 678 bp in length. According to one embodiment, the nucleic acid encoding the human codon optimized GJB2 protein comprises SEQ ID NO: 12. According to one embodiment, the nucleic acid is at least 85% identical to SEQ ID NO: 12. According to one embodiment, the nucleic acid is at least 90% identical to SEQ ID NO: 12. According to one embodiment, the nucleic acid is at least 95% identical to SEQ ID NO: 12. According to one embodiment, the nucleic acid is at least 99% identical to SEQ ID NO: 12. According to one embodiment, the nucleic acid consists of SEQ ID NO: 12.

FIG. 12 shows the nucleic acid sequence of the human codon optimized GJB2 (hGJB2co6) (SEQ ID NO. 12).

According to some embodiments, the nucleic acid sequence encoding a human codon optimized GJB2 protein is 678 bp in length. According to one embodiment, the nucleic acid encoding the human codon optimized GJB2 protein comprises SEQ ID NO: 13. According to one embodiment, the nucleic acid is at least 85% identical to SEQ ID NO: 13. According to one embodiment, the nucleic acid is at least 90% identical to SEQ ID NO: 13. According to one embodiment, the nucleic acid is at least 95% identical to SEQ ID NO: 13. According to one embodiment, the nucleic acid is at least 99% identical to SEQ ID NO: 13. According to one embodiment, the nucleic acid consists of SEQ ID NO: 13.

FIG. 13 shows the nucleic acid sequence of the human codon optimized GJB2 (hGJB2co9) (SEQ ID NO. 13).

According to some embodiments, the nucleic acid sequence encoding a human codon optimized GJB2 protein is 681 bp in length. According to one embodiment, the nucleic acid encoding the human codon optimized GJB2 protein comprises SEQ ID NO: 18. According to one embodiment, the nucleic acid is at least 85% identical to SEQ ID NO: 18. According to one embodiment, the nucleic acid is at least 90% identical to SEQ ID NO: 18. According to one embodiment, the nucleic acid is at least 95% identical to SEQ ID NO: 18. According to one embodiment, the nucleic acid is at least 99% identical to SEQ ID NO: 18. According to one embodiment, the nucleic acid consists of SEQ ID NO: 18.

FIG. 18 shows the nucleic acid sequence of the hybrid codon optimized construct (CO369) (SEQ ID NO. 18).

According to some embodiments, the nucleic acid sequence encoding the human codon optimized GJB2 protein is 678 bp in length. According to one embodiment, the nucleic acid encoding the human codon optimized GJB2 protein comprises SEQ ID NO: 13. According to one embodiment, the nucleic acid is at least 85% identical to SEQ ID NO: 13. According to one embodiment, the nucleic acid is at least 90% identical to SEQ ID NO: 13. According to one embodiment, the nucleic acid is at least 95% identical to SEQ ID NO: 13. According to one embodiment, the nucleic acid is at least 99% identical to SEQ ID NO: 13. According to one embodiment, the nucleic acid consists of SEQ ID NO: 13.

According to embodiments of the disclosure, the AAV vector as described herein comprises one or more codon optimized nucleic acid sequences, e.g., nucleic acid sequences encoding a GJB2 therapeutic protein or functional fragment thereof. In one embodiment, the ceDNA vector comprises a codon optimized nucleic acid sequence encoding a GJB2 sequence. In some embodiments, an AAV vector for expression of GJB2 can have a sequence encoding a full-length GJB2 protein. In some other embodiments, an AAV vector expression of GJB2 can have a sequence encoding a truncated GJB2 protein.

According to some embodiments, an AAV vector for expression of GJB2 protein can further comprise regulatory sequences such as promoters, secretion signals, polyA regions, and enhancers.

Promoters

Expression of GJB2 therapeutic protein or fragment thereof from an AAV vector can be achieved both spatially and temporally using one or more of the promoters as described herein.

Expression cassettes of the AAV vector for expression of GJB2 protein can include a promoter, which can influence overall expression levels.

Various promoters are contemplated for use in the present disclosure.

According to some embodiments, the promoter is an endogenous GJB2 promoter. The GJB2 promoter is a support-cell specific promoter and can transduce cells of the inner ear that express the GJB2 gene; this promoter can be used for production of scAAV given its short length. According to some embodiments, the promoter comprises SEQ ID NO: 6. According to some embodiments, the promoter consists of SEQ ID NO: 6. FIG. 8 shows the nucleic acid sequence of the GJB2 promoter (SEQ ID NO. 6).

According to some embodiments, the promoter is a CBA promoter. The CBA promoter is a strong ubiquitous promoter that can transduce multiple cell types in the inner ear. According to some embodiments, the promoter comprises SEQ ID NO: 1. According to some embodiments, the promoter consists of SEQ ID NO: 1. FIG. 3 shows the nucleic acid sequence of the CBA promoter (SEQ ID NO. 1).

According to some embodiments, the promoter is an EF1a promoter. The EF1a promoter is a strong ubiquitous promoter of mammalian origin that can transduce multiple cell types in the inner ear, and can be used for production of scAAV given its short length. According to some embodiments, the promoter comprises SEQ ID NO: 2. According to some embodiments, the promoter consists of SEQ ID NO: 2. FIG. 4 shows the nucleic acid sequence of the EF1a promoter (SEQ ID NO. 2).

According to some embodiments, the promoter is a CASI promoter. The CASI promoter is a strong ubiquitous promoter that can transduce multiple cell types in the inner ear, and can be used for production of scAAV given its short length. According to some embodiments, the promoter comprises SEQ ID NO: 3. According to some embodiments, the promoter consists of SEQ ID NO: 3. FIG. 5 shows the nucleic acid sequence of the CASI promoter (SEQ ID NO. 3).

According to some embodiments, the promoter is a smCBA promoter. The smCBA promoter is a strong ubiquitous promoter that can transduce multiple cell types in the inner ear, and can be used for production of scAAV given its short length. According to some embodiments, the promoter comprises SEQ ID NO: 4. According to some embodiments, the promoter consists of SEQ ID NO: 4. FIG. 6 shows the nucleic acid sequence of the smCBA promoter (SEQ ID NO. 4.).

According to some embodiments, the promoter is a GFAP promoter. The GFAP promoter is cell-specific and has activity in support cells of the inner ear. According to some embodiments, the promoter comprises SEQ ID NO: 5. According to some embodiments, the promoter consists of SEQ ID NO: 5. FIG. 7 shows the nucleic acid sequence of the GFAP promoter (SEQ ID NO. 5).

Inverted Terminal Repeats

As described herein, AAV vectors for expression of GJB2 protein contain nucleic acid, e.g., a GJB2 nucleic acid sequence (e.g., a codon optimized GJB2 nucleic acid sequence), positioned between two inverted terminal repeat (ITR) sequences.

In some embodiments, the ITR sequence can be from viruses of the Parvoviridae family, subfamily Parvovirinae, genus *Dependovirus*, which includes adeno-associated virus (AAV), which normally infects humans (e.g., serotypes 2, 3A, 3B, 5, and 6) or primates (e.g., serotypes 1 and 4). There are a number of serotypes that are homologous, e.g. AAV2, AAV4, AAV6, AAV8.

According to some embodiments, the ITR is from a *Dependovirus* such as AAV (e.g., AAV1, AAV2, AAV3, AAV4, AAV5, AAV 5, AAV7, AAV8, AAV9, AAV10, AAV 11, AAV12, AAVrh8, AAVrh10, AAV-DJ, and AAV-DJ8 genome, chimeric ITRs, or ITRs from any synthetic AAV. According to some embodiments, the serotype of the ITRs of the AAV vector are independently selected from the group consisting of AAV1, AAV2, AAV3, AAV4, AAV5, AAV6, AAV7, AAV8, AAV9, AAV10, AAV11, and AAV12.

The inverted terminal repeat (ITR) sequences are required for efficient multiplication of the AAV genome, due to their ability to form hairpin structures that allows synthesis of the second DNA strand. scAAV shortened ITRs (TRS) form an intra-molecular double-stranded DNA template, thus removing the rate-limiting step of second-strand synthesis.

An ordinarily skilled artisan is aware that ITR sequences have a common structure of a double-stranded Holliday junction, which typically is a T-shaped or Y-shaped hairpin structure, where each WT-ITR is formed by two palindromic arms or loops (B-B' and C-C') embedded in a larger palindromic arm (A-A'), and a single stranded D sequence, (where the order of these palindromic sequences defines the flip or flop orientation of the ITR). See, for example, structural analysis and sequence comparison of ITRs from different AAV serotypes (AAV1-AAV6) and described in Grimm et al., J. Virology, 2006; 80(1); 426-439; Yan et al., J. Virology, 2005; 364-379; Duan et al., Virology 1999; 261; 8-14. One of ordinary skill in the art can readily determine WT-ITR sequences from any AAV serotype for use in an AAV vector based on the sequence comparison of ITRs from different AAV serotypes (AAV1-AAV6, and avian AAV (AAAV) and bovine AAV (BAAV)) described in Grimm et al., J. Virology, 2006; 80(1); 426-439; that show the % identity of the left ITR of AAV2 to the left ITR from other serotypes: AAV-1 (84%), AAV-3 (86%), AAV-4 (79%), AAV-5 (58%), AAV-6 (left ITR) (100%) and AAV-6 (right ITR) (82%).

FIG. 9 shows the nucleic acid sequences of the following ITRs (AAV2) 5'-3': for single stranded (ss) and self-complimentary (sc) AAV genomes (SEQ ID NO. 7); 3'-5': for single stranded (ss) AAV genomes only (SEQ ID NO. 8); 3'-5': for self-complimentary (sc) AAV genomes only (SEQ ID NO. 9).

In some embodiments, the nucleotide sequence of the WT-ITR sequence can be modified (e.g., by modifying 1, 2, 3, 4 or 5, or more nucleotides or any range therein), whereby the modification is a substitution for a complementary nucleotide, e.g., G for a C, and vice versa, and T for an A, and vice versa. Accordingly, in some embodiments, an ITR is used that is substantially WT—that is, it has the basic loop structure of the WT but some conservative nucleotide changes that do not alter or affect the properties.

GJB2 Gene Therapy for Genetic Hearing Loss

The disclosure generally provides methods for producing recombinant adeno-associated virus (AAV) viral particles comprising a GJB2 gene construct and their use in methods of gene therapy for genetic hearing loss. The AAV vectors as described herein are particularly efficient at delivering nucleic acids (e.g., GJB2 gene construct) to inner ear cells. Methods to create, evaluate, and utilize recombinant adeno-associated virus (rAAV) therapeutic vectors capable of efficiently delivering GJB2 into cells for expression and subsequent secretion are described herein. Optimally-modified GJB2/Connexin26 (Cx26) cDNA and associated genetic elements for use in recombinant adeno-associated virus (rAAV)-based gene therapy for genetic hearing loss, including the treatment and/or prevention of DFNB1 and DFNA3A-associated congenital deafness, are described herein.

Recombinant adeno-associated virus (rAAV) vector can efficiently accommodate both GJB2 target gene and associated genetic elements. Furthermore, such vectors can be designed to specifically express GJB2 in therapeutically relevant supporting cells of the cochlea. The disclosure describes a method to create, evaluate, and utilize rAAV therapeutic vectors able to efficiently deliver the functional GJB2 gene to patients.

The GJB2 gene construct may comprise: (1) codon/sequence-optimized 0.68 kb human GJB2 cDNA with or without a 27-nucleotide hemagglutinin (HA) C-terminal tag; (2) one of the following promoter elements optimized to drive high GJB2 expression: (a) an ubiquitously-active 1.7 kb CBA, 0.96 kb small CBA (smCBA), 0.81 kb EF1a, or 1.06 kb CASI promoter; (b) a cochlear-support cell or GJB2 expression-specific 1.68 kb GFAP, 0.13/0.54/1.0 kb small/medium/large GJB2 promoters, or a sequential combination of 2-3 individual GJB2 expression-specific promoters; (3) a 0.9 kb 3'-UTR regulatory region comprising the Woodchuck Hepatitis Virus Posttranscriptional Regulatory Element (WPRE) followed by either a SV40 or human growth hormone (hGH) polyadenylation signal, (4) either two 143-base sequence-modulated inverted terminal repeats (ITRs) flanking the AAV genomic cassette or a self-complimentary AAV (scAAV) genomic cassette consisting of two inverted identical repeats (each no longer than 3.0 kb) separated by a 113-base scAAV-enabling ITR (ITRΔtrs) and flanked on either end by 143-base sequence-modulated ITRs; and (5) a protein capsid variant optimally suited for cochlear delivery.

The HA tag is human influenza hemagglutinin, a surface glycoprotein used as a general epitope tag in expression vectors, facilitating detection of the protein of interest. Woodchuck Hepatitis Virus Posttranscriptional Regulatory Element (WPRE) is a DNA sequence that enhances expression of the protein of interest by generating a tertiary structure that stabilizes its mRNA. The poly(A) sequence is an important element that promotes RNA processing and transcript stability. The SV40/bGH sequence is a terminator sequence that signals the end of a transcriptional unit.

According to some embodiments, the AAV vectors described herein are particularly suited to deliver and express GLB2 in the cochlear support cells. According to some embodiments, the AAV vectors described herein are particularly suited to deliver and express GLB2 in one or more of the external support cells and/or the organ of Corti support cells. According to some embodiments, the AAV vectors described herein are particularly suited to deliver and express GLB2 in one or more of the outer hair cells, the inner hair cells, hensen's cells, deiters' cells, pillar cells, inner phalangeal cells and/or outer phalangeal cells/border cells.

Adeno-Associated Virus (AAV)

Adeno-Associated Virus (AAV) is a non-pathogenic single-stranded DNA parvovirus. AAV has a capsid diameter of about 20 nm. Each end of the single-stranded DNA genome contains an inverted terminal repeat (ITR), which is the only cis-acting element required for genome replication and packaging. The AAV genome carries two viral genes: rep and cap. The virus utilizes two promoters and alternative splicing to generate four proteins necessary for replication (Rep 78, Rep 68, Rep 52 and Rep 40). A third promoter generates the transcript for three structural viral capsid proteins, 1, 2 and 3 (VP1, VP2 and VP3), through a combination of alternate splicing and alternate translation start codons. Berns & Linden *Bioessays* 1995; 17:237-45. The three capsid proteins share the same C-terminal 533 amino acids, while VP2 and VP1 contain additional N-terminal sequences of 65 and 202 amino acids, respectively. The AAV virion contains a total of 60 copies of VP1, VP2, and VP3 at a 1:1:20 ratio, arranged in a T-1 icosahedral symmetry. Rose et al. *J Virol.* 1971; 8:766-70. AAV requires Adenovirus (Ad), Herpes Simplex Virus (HSV) or other viruses as a helper virus to complete its lytic life-cycle. Atchison et al. *Science,* 1965; 149:754-6; Hoggan et al. *Proc Natl Acad Sci USA,* 1966; 55:1467-74. In the absence of the helper virus, wild-type AAV establishes latency by integration with the assistance of Rep proteins through the interaction of the ITR with the chromosome. Berns & Linden (1995).

AAV Serotypes

There are a number of different AAV serotypes, including AAV1, AAV2, AAV3, AAV4, AAV5, AAV6, AAV7, AAV8, AAV9, AAV10, AAV11, AAV12, AAVrh8, AAVrh10, Anc80L65, and variants or hybrids thereof. In vivo studies have shown that the various AAV serotypes display different tissue or cell tropisms. For example, AAV1 and AAV6 are two serotypes that, are efficient for the transduction of skeletal muscle. Gao, et al. *Proc Natl Acad Sci USA,* 2002; 99:11854-11859; Xiao, et al. *J Virol.* 1999; 73:3994-4003; Chao, et al. Mol Ther. 2000; 2:619-623. AAV-3 has been shown to be superior for the transduction of megakaryocytes. Handa, et al. *J Gen Virol.* 2000; 81:2077-2084. AAV5 and AAV6 infect apical airway cells efficiently. Zabner, et al. *J Virol.* 2000; 74:3852-3858; Halbert, et al. J Virol. 2001; 75:6615-6624. AAV2, AAV4, and AAV5 transduce different types of cells in the central nervous system. Davidson, et al. *Proc Natl Acad Sci USA.* 2000; 97:3428-3432. AAV8 and AAV5 can transduce liver cells better than AAV-2. AAV-5 based vectors transduced certain cell types (cultured airway epithelial cells, cultured striated muscle cells and cultured human umbilical vein endothelial cells) at a higher efficiency than AAV2, while both AAV2 and AAV5 showed poor transduction efficiencies for NIH 3T3, skbr3 and t-47D cell lines. Gao, et al. *Proc Natl Acad Sci USA.* 2002; 99:11854-11859; Mingozzi, et al. *J Virol.* 2002; 76:10497-10502. WO 99/61601. AAV4 was found to transduce rat retina most efficiently, followed by AAV5 and AAV1. Rabinowitz, et al. *J Virol.* 2002; 76:791-801; Weber, et al. *Mol Ther.* 2003; 7:774-781. In summary, AAV1, AAV2, AAV4, AAV5, AAV8, and AAV9 show tropism for CNS tissues. AAV1, AAV8, and AAV9 show tropism for heart tissues. AAV2 exhibits tropism for kidney tissue. AAV7, AAV8, and AAV9 exhibit tropism for liver tissue. AAV4, AAV5, AAV6, and AAV9 exhibits tropism for lung tissue. AAV8 exhibits tropism for pancreas cells. AAV3, AAV5, and AAV8 show tropism for photoreceptor cells. AAV1, AAV2, AAV4, AAV5, and AAV8 exhibit tropism for retinal pigment epithelium (RPE) cells. AAV1, AAV6, AAV7, AAV8, and AAV9 show tropism for skeletal muscle.

Further modification to the virus can be performed to enhance the efficiency of gene transfer, for example, by improving the tropism of each serotype. One approach is to swap domains from one serotype capsid to another, and thus create hybrid vectors with desirable qualities from each parent. As the viral capsid is responsible for cellular receptor binding, the understanding of viral capsid domain(s) critical for binding is important. Mutation studies on the viral capsid (mainly on AAV2) performed before the availability of the crystal structure were mostly based on capsid surface functionalization by adsorption of exogenous moieties, insertion of peptide at a random position, or comprehensive mutagenesis at the amino acid level. Choi, et al. *Curr Gene Ther.* 2005 June; 5(3): 299-310, describe different approaches and considerations for hybrid serotypes.

Capsids from other AAV serotypes offer advantages in certain in vivo applications over rAAV vectors based on the AAV2 capsid. First, the appropriate use of rAAV vectors with particular serotypes may increase the efficiency of gene delivery in vivo to certain target cells that are poorly infected, or not infected at all, by AAV2 based vectors. Secondly, it may be advantageous to use rAAV vectors based on other AAV serotypes if re-administration of rAAV vector becomes clinically necessary. It has been demonstrated that re-administration of the same rAAV vector with the same capsid can be ineffective, possibly due to the generation of neutralizing antibodies generated to the vector. Xiao, et al. 1999; Halbert, et al. 1997. This problem may be avoided by administration of a rAAV particle whose capsid is composed of proteins from a different AAV serotype, not affected by the presence of a neutralizing antibody to the first rAAV vector. Xiao, et al. 1999. For the above reasons, recombinant AAV vectors constructed using cap genes from serotypes including and in addition to AAV2 are desirable. It will be recognized that the construction of recombinant HSV vectors similar to rHSV but encoding the cap genes from other AAV serotypes, e.g., AAV1, AAV2, AAV3, AAV5 to AAV9, is achievable using the methods described herein to produce rHSV, In certain preferred embodiments of the invention as described herein, recombinant AAV vectors constructed using cap genes from different AAV are preferred. The significant advantages of construction of these additional rHSV vectors are ease and savings of time, compared with alternative methods used for the large-scale production of rAAV. In particular, the difficult process of constructing new rep and cap inducible cell lines for each different capsid serotypes is avoided.

Making Recombinant AAV (rAAV) Vectors

The production, purification, and characterization of the rAAV vectors of the present invention may be carried out using any of the many methods known in the art. For reviews of laboratory-scale production methods, see, e.g., Clark R K, Recent advances in recombinant adeno-associated virus vector production. *Kidney Int.* 61s:9-15 (2002); Choi V W et al., Production of recombinant adeno-associated viral vectors for in vitro and in vivo use. *Current Protocols in Molecular Biology* 16.25.1-16.25.24 (2007) (hereinafter Choi et al.); Grieger J C & Samulski R J, Adeno-associated virus as a gene therapy vector: Vector development, production, and clinical applications. *Adv Biochem Engin/Biotechnol* 99:119-145 (2005) (hereinafter Grieger & Samulski); Heilbronn R & Weger S, Viral Vectors for Gene Transfer: Current Status of Gene Therapeutics, in M. Schäfer-Korting (ed.), *Drug Delivery*, Handbook of Experimental Pharmacology, 197: 143-170 (2010) (hereinafter Heilbronn); Howarth J L et al., Using viral vectors as gene transfer tools. *Cell Biol Toxicol* 26:1-10 (2010) (hereinafter Howarth). The production methods described below are intended as non-limiting examples.

AAV vector production may be accomplished by cotransfection of packaging plasmids. Heilbronn. The cell line supplies the deleted AAV genes rep and cap and the required helper virus functions. The adenovirus helper genes, VA-RNA, E2A and E4 are transfected together with the AAV rep and cap genes, either on two separate plasmids or on a single helper construct. A recombinant AAV vector plasmid wherein the AAV capsid genes are replaced with a transgene expression cassette (comprising the gene of interest, e.g., a GJB2 nucleic acid; a promoter; and minimal regulatory elements) bracketed by ITRs, is also transfected. These packaging plasmids are typically transfected into 293 cells, a human cell line that constitutively expresses the remaining required Ad helper genes, E1A and E1B. This leads to amplification and packaging of the AAV vector carrying the gene of interest.

Multiple serotypes of AAV, including 12 human serotypes and more than 100 serotypes from nonhuman primates have now been identified. Howarth et al. Cell Biol Toxicol 26:1-10 (2010). The AAV vectors of the present invention may comprise capsid sequences derived from AAVs of any known serotype. As used herein, a "known serotype" encompasses capsid mutants that can be produced using methods known in the art. Such methods, include, for example, genetic manipulation of the viral capsid sequence, domain swapping of exposed surfaces of the capsid regions of different serotypes, and generation of AAV chimeras using techniques such as marker rescue. See Bowles et al. Marker rescue of adeno-associated virus (AAV) capsid mutants: A novel approach for chimeric AAV production. Journal of Virology, 77(1): 423-432 (2003), as well as references cited therein. Moreover, the AAV vectors of the present invention may comprise ITRs derived from AAVs of any known serotype. Preferentially, the ITRs are derived from one of the human serotypes AAV1-AAV12. In some embodiments of the present invention, a pseudotyping approach is employed, wherein the genome of one ITR serotype is packaged into a different serotype capsid.

According to some embodiments, the capsid sequences are derived from one of the human serotypes AAV1-AAV12. According to some embodiments, the capsid sequences are derived from serotype AAV2. According to some embodiments, the capsid sequences are derived from an AAV2 variant with high tropism for targeting support cells (e.g., outer hair cells, inner hair cells, hensen's cells, deiters' cells, pillar cells, inner phalangeal cells, outer phalangeal cells/border cells. Capsids suitable for this purpose comprise AAV2 and AAV2 variants including AAV2-tYF, AAV2-MeB, AAV2-P2V2, AAV2-MeStYFTV, AAV2-P2V6; as well as AAV5, AAV8, and Anc80L65.

According to some embodiments, recombinant AAV vectors can be directly targeted by genetic manipulation of the viral capsid sequence, particularly in the looped out region of the AAV three-dimensional structure, or by domain swapping of exposed surfaces of the capsid regions of different serotypes, or by generation of AAV chimeras using techniques such as marker rescue. See Bowles et al. Marker rescue of adeno-associated virus (AAV) capsid mutants: A novel approach for chimeric AAV production. Journal of Virology, 77(1): 423-432 (2003), as well as references cited therein.

One possible protocol for the production, purification, and characterization of recombinant AAV (rAAV) vectors is provided in Choi et al. Generally, the following steps are involved: design a transgene expression cassette, design a capsid sequence for targeting a specific receptor, generate adenovirus-free rAAV vectors, purify and titer. These steps are summarized below and described in detail in Choi et al.

The transgene expression cassette may be a single-stranded AAV (ssAAV) vector or a "dimeric" or self-complementary AAV (scAAV) vector that is packaged as a pseudo-double-stranded transgene. Choi et al.; Howarth et al., Using a traditional ssAAV vector generally results in a slow onset of gene expression (from days to weeks until a plateau of transgene expression is reached) due to the required conversion of single-stranded AAV DNA into double-stranded DNA. In contrast, scAAV vectors show an onset of gene expression within hours that plateaus within days after transduction of quiescent cells. Heilbronn. According to some embodiments, a scAAV is used, where the scAAV has rapid transduction onset and increased stability compared to single stranded AAV. Alternatively, the transgene expression cassette may be split between two AAV vectors, which allows delivery of a longer construct. See e.g., Daya S. and Berns, K. I., Gene therapy using adeno-associated virus vectors. *Clinical Microbiology Reviews,* 21(4): 583-593 (2008) (hereinafter Daya et al.). A ssAAV vector can be constructed by digesting an appropriate plasmid (such as, for example, a plasmid containing the GJB2 gene) with restriction endonucleases to remove the rep and cap fragments, and gel purifying the plasmid backbone containing the AAVwt-ITRs. Choi et al. Subsequently, the desired transgene expression cassette can be inserted between the appropriate restriction sites to construct the single-stranded rAAV vector plasmid. A scAAV vector can be constructed as described in Choi et al.

Then, a large-scale plasmid preparation (at least 1 mg) of the rAAV vector and the suitable AAV helper plasmid and pXX6 Ad helper plasmid can be purified by double CsCl gradient fractionation. Choi et al. A suitable AAV helper plasmid may be selected from the pXR series, pXR1-pXR5, which respectively permit cross-packaging of AAV2 ITR genomes into capsids of AAV serotypes 1 to 5. The appropriate capsid may be chosen based on the efficiency of the capsid's targeting of the cells of interest. Known methods of varying genome (i.e., transgene expression cassette) length and AAV capsids may be employed to improve expression and/or gene transfer to specific cell types (e.g., retinal cone cells). See, e.g., Yang G S, Virus-mediated transduction of murine retina with adeno-associated virus: Effects of viral capsid and genome size. Journal of Virology, 76(15): 7651-7660.

Next, 293 cells are transfected with pXX6 helper plasmid, rAAV vector plasmid, and AAV helper plasmid. Choi et al. Subsequently the fractionated cell lysates are subjected to a multistep process of rAAV purification, followed by either CsCl gradient purification or heparin sepharose column purification. The production and quantitation of rAAV virions may be determined using a dot-blot assay. In vitro transduction of rAAV in cell culture can be used to verify the infectivity of the virus and functionality of the expression cassette.

In addition to the methods described in Choi et al., various other transfection methods for production of AAV may be used in the context of the present invention. For example, transient transfection methods are available, including methods that rely on a calcium phosphate precipitation protocol.

In addition to the laboratory-scale methods for producing rAAV vectors, the present invention may utilize techniques known in the art for bioreactor-scale manufacturing of AAV vectors, including, for example, Heilbronn; Clement, N. et al. Large-scale adeno-associated viral vector production using a herpesvirus-based system enables manufacturing for clinical studies. Human Gene Therapy, 20: 796-606.

Advances toward achieving the desired goal of scalable production systems that can yield large quantities of clinical grade rAAV vectors have largely been made in production systems that utilize transfection as a means of delivering the genetic elements needed for rAAV production in a cell. For example, removal of contaminating adenovirus helper has been circumvented by replacing adenovirus infection with plasmid transfection in a three-plasmid transfection system in which a third plasmid comprises nucleic acid sequences encoding adenovirus helper proteins (Xiao, et al. 1998), Improvements in two-plasmid transfection systems have also simplified the production process and increased rAAV vector production efficiency (Grimm, et al. 1998).

Several strategies for improving yields of rAAV from cultured mammalian cells are based on the development of specialized producer cells created by genetic engineering. In one approach, production of rAAV on a large scale has been accomplished by using genetically engineered "proviral" cell lines in which an inserted AAV genome can be "rescued" by infecting the cell with helper adenovirus or HSV. Proviral cell lines can be rescued by simple adenovirus infection, offering increased efficiency relative to transfection protocols.

A second cell-based approach to improving yields of rAAV from cells involves the use of genetically engineered "packaging" cell lines that harbor in their genomes either the AAV rep and cap genes, or both the rep-cap and the ITR-gene of interest (Qiao, et al. 2002). In the former approach, in order to produce rAAV, a packaging cell line is either infected or transfected with helper functions, and with the AAV ITR-GOI elements. The latter approach entails infection or transfection of the cells with only the helper functions. Typically, rAAV production using a packaging cell line is initiated by infecting the cells with wild-type adenovirus, or recombinant adenovirus. Because the packaging cells comprise the rep and cap genes, it is not necessary to supply these elements exogenously.

rAAV yields from packaging cell lines have been shown to be higher than those obtained by proviral cell line rescue or transfection protocols.

Improved yields of rAAV have been made using approaches based on delivery of helper functions from herpes simplex virus (HSV) using recombinant HSV amplicon systems. Although modest levels of rAAV vector yield, of the order of 150-500 viral genomes (vg) per cell, were initially repotted (Conway, et al. 1997), more recent improvements in rHSV amplicon-based systems have provided substantially higher yields of rAAV v.g. and infectious particles (ip) per cell (Feudner, et al. 2002). Amplicon systems are inherently replication-deficient; however the use of a "gutted" vector, replication-competent (rcHSV), or replication-deficient rHSV still introduces immunogenic HSV components into rAAV production systems. Therefore, appropriate assays for these components and corresponding purification protocols for their removal must be implemented.

In addition to these methods, methods for producing recombinant AAV viral particles in a mammalian cell are described herein comprising co-infecting a mammalian cell capable of growing in suspension with a first recombinant herpesvirus comprising a nucleic acid sequence encoding an AAV rep and an AAV cap gene each operably linked to a promoter, and a second recombinant herpesvirus comprising a GJB2 gene, and a promoter operably linked to said GJB2 gene, flanked by AAV inverted terminal repeats to facilitate packaging of the gene of interest, and allowing the virus to infect the mammalian cell, thereby producing recombinant AAV viral particles in a mammalian cell.

Any type of mammalian cell that is capable of supporting replication of herpesvirus is suitable for use according to the methods of the invention as described herein. Accordingly, the mammalian cell can be considered a host cell for the replication of herpesvirus as described in the methods herein. Any cell type for use as a host cell is contemplated by the present invention, as long as the cell is capable of supporting replication of herpesvirus. Examples of suitable genetically unmodified mammalian cells include but are not limited to cell lines such as HEK-293 (293), Vero, RD, BHK-21, HT-1080, A549, Cos-7, ARPE-19, and MRC-5.

The host cells used in the various embodiments of the present invention may be derived, for example, from mammalian cells such as human embryonic kidney cells or primate cells. Other cell types might include, but are not limited to BHK cells, Vero cells, CHO cells or any eukaryotic cells for which tissue culture techniques are established as long as the cells are herpesvirus permissive. The term "herpesvirus permissive" means that the herpesvirus or herpesvirus vector is able to complete the entire intracellular virus life cycle within the cellular environment. In certain embodiments, methods as described occur in the mammalian cell line BHK, growing in suspension. The host cell may be derived from an existing cell line, e.g., from a BHK cell line, or developed de novo.

The methods for producing a rAAV gene construct described herein include also a recombinant AAV viral particle produced in a mammalian cell by the method comprising co-infecting a mammalian cell capable of growing in suspension with a first recombinant herpesvirus comprising a nucleic acid encoding an AAV rep and an AAV cap gene each operably linked to a promoter; and (ii) a second recombinant herpesvirus comprising a GJB2, and a promoter operably linked to said GJB2 gene; and allowing the virus to infect the mammalian cell, and thereby producing recombinant AAV viral particles in a mammalian cell. As described herein, the herpesvirus is a virus selected from the group consisting of: cytomegalovirus (CMV), herpes simplex (HSV) and varicella zoster (VZV) and epstein barr virus (EBV). The recombinant herpesvirus is replication defective. According to some embodiments, the AAV cap gene has a serotype selected from the group consisting of AAV1, AAV2, AAV3, AAV4, AAV5, AAV6, AAV7, AAV8, AAV9, AAV10, AAV11, AAV12, AAVrh8, AAVrh10, Anc80L65, including variants or hybrids (e.g., capsid hybrids of two or more serotypes).

U.S. Patent Application Publication No. 2007/0202587, incorporated by reference in its entirety herein, describes required elements of rAAV Production Systems. Recombinant AAV is produced in vitro by introduction of gene constructs into cells known as producer cells. Known systems for production of rAAV employ three fundamental elements: (1) a gene cassette containing the gene of interest, (2) a gene cassette containing AAV rep and cap genes and (3) a source of "helper" virus proteins.

The first gene cassette is constructed with the gene of interest flanked by inverted terminal repeats (ITRs) from AAV. ITRs function to direct integration of the gene of interest into the host cell genome and are essential for encapsidation of the recombinant genome. Hermonat and Muzyczka, 1984; Samulski et al. 1983. The second gene cassette contains rep and cap, AAV genes encoding proteins needed for replication and packaging of rAAV. The rep gene encodes four proteins (Rep 78, 68, 52 and 40) required for DNA replication. The cap genes encode three structural proteins (VP1, VP2, and VP3) that make up the virus capsid. Muzyczka and Berns, 2001.

The third element is required because AAV does not replicate on its own. Helper functions are protein products from helper DNA viruses that create a cellular environment conducive to efficient replication and packaging of rAAV. Traditionally, adenovirus (Ad) has been used to provide helper functions for rAAV, but herpesviruses can also provide these functions as discussed herein.

Production of rAAV vectors for gene therapy is carried out in vitro, using suitable producer cell lines such as BHK cells grown in suspension. Other cell lines suitable for use in the invention include HEK-293 (293), Vero, RD, BHK-21, HT-1080, A549, Cos-7, ARPE-19, and MRC-5.

Any cell type can be used as a host cell, as long as the cell is capable of supporting replication of a herpesvirus. One of skill in the art would be familiar with the wide range of host cells that can be used in the production of herpesvirus from host cells. Examples of suitable genetically unmodified mammalian host cells, for example, may include but are not limited to cell lines such as HEK-293 (293), Vero, RD, BHK-21, HT-1080, A549, Cos-7, ARPE-19, and MRC-5.

A host cell may be adapted for growth in suspension culture. The host cells may be Baby Hamster Kidney (BHK) cells. BHK cell line grown in suspension is derived from an adaptation of the adherent BHK cell line. Both cell lines are available commercially.

One strategy for delivering all of the required elements for rAAV production utilizes two plasmids and a helper virus. This method relies on transfection of the producer cells with plasmids containing gene cassettes encoding the necessary gene products, as well as infection of the cells with Ad to provide the helper functions. This system employs plasmids with two different gene cassettes. The first is a proviral plasmid encoding the recombinant DNA to be packaged as rAAV. The second is a plasmid encoding the rep and cap genes, To introduce these various elements into the cells, the cells are infected with Ad as well as transfected with the two plasmids. The gene products provided by Ad are encoded by the genes E1a, E1b, E2a, E4orf6, and Va. Samulski et al. 1998: Hauswirth et al. 2000; Muzyczka and Burns, 2001. Alternatively, in more recent protocols, the Ad infection step can be replaced by transfection with an adenovirus "helper plasmid" containing the VA, E2A and E4 genes. Xiao et al. 1998; Matsushita, et al. 1998.

While Ad has been used conventionally as the helper virus for rAAV production, other DNA viruses, such as herpes simplex virus type 1 (HSV-1) can be used as well. The minimal set of HSV-1 genes required for AAV2 replication and packaging has been identified, and includes the early genes UL5, UL8, UL52 and UL29. Muzyczka and Burns, 2001. These genes encode components of the HSV-1 core replication machinery, i.e., the helicase, primase, primase accessory proteins, and the single-stranded DNA binding protein. Knipe, 1989; Weller, 1991. This rAAV helper property of HSV-1 has been utilized in the design and construction of a recombinant herpes virus vector capable of providing helper virus gene products needed for rAAV production. Conway et al. 1999.

Production of rAAV vectors for gene therapy is carried out in vitro, using suitable producer cell lines such as BHK cells grown in suspension. Other cell lines suitable for use in the invention include HEK-293 (293), Vero, RD, BHK-21, HT-1080, A549, Cos-7, ARPE-19, and MRC-5.

Any cell type can be used as a host cell, as long as the cell is capable of supporting replication of a herpesvirus. One of skill in the art would be familiar with the wide range of host-cells that can be used in the production of herpesvirus from host cells. Examples of suitable genetically unmodified mammalian host cells, for example, may include but are not limited to cell lines such as HEK-293 (293), Vero, RD, BHK-21, HT-1080, A549, Cos-7, ARPE-19, and MRC-5.

A host cell may be adapted for growth in suspension culture. In certain embodiments of the present invention, the host cells are Baby Hamster Kidney (BHK) cells. BHK cell line grown in suspension is derived from an adaptation of the adherent BHK cell line. Both cell lines are available commercially.

rHSV-Based rAAV Manufacturing Process

Methods for the production of recombinant AAV viral particles in cells growing in suspension are described herein. Suspension or non-anchorage dependent cultures from continuous established cell lines are the most widely used means of large scale production of cells and cell products. Large scale suspension culture based on fermentation technology has clear advantages for the manufacturing of mammalian cell products. Homogeneous conditions can be provided in the bioreactor which allows for precise monitoring and control of temperature, dissolved oxygen, and pH, and ensure that representative samples of the culture can be taken. The rHSV vectors used are readily propagated to high titer on permissive cell lines both in tissue culture flasks and bioreactors, and provided a production protocol amenable to scale-up for virus production levels necessary for clinical and market production.

Cell culture in stirred tank bioreactors provides very high volume-specific culture surface area and has been used for the production of viral vaccines (Griffiths, 1986). Furthermore, stirred tank bioreactors have industrially been proven to be scalable. One example is the multiplate CELL CUBE cell culture system. The ability to produce infectious viral vectors is increasingly important to the pharmaceutical industry, especially in the context of gene therapy.

Growing cells according to methods described herein may be done in a bioreactor that allows for large scale production of fully biologically-active cells capable of being infected by the Herpes vectors of the present invention. Bioreactors have been widely used for the production of biological products from both suspension and anchorage dependent animal cell cultures. Most large-scale suspension cultures are operated as batch or fed-batch processes because they are the most straightforward to operate and scale up. However, continuous processes based on chemostat or perfusion principles are available. The bioreactor system may be set up to include a system to allow for media exchange. For example, filters may be incorporated into the bioreactor system to allow for separation of cells from spent media to facilitate media exchange. In some embodiments of the present methods for producing Herpes virus, media exchange and perfusion is conducted beginning on a certain day of cell growth. For example, media exchange and perfusion can begin on day 3 of cell growth. The filter may be external to the bioreactor, or internal to the bioreactor.

A method for producing recombinant AAV viral particles may comprise: co-infecting a suspension cell with a first recombinant herpesvirus comprising a nucleic acid encoding an AAV rep and an AAV cap gene each operably linked to a promoter; and a second recombinant herpesvirus comprising a GJB2 gene construct, and a promoter operably linked to said gene of interest; and allowing the cell to produce the recombinant AAV viral particles, thereby producing the recombinant AAV viral particles. The cell may be HEK-293 (293), Vero, RD, BHK-21, HT-1080, A549, Cos-7, ARPE-19, and MRC-5. According to some embodiments, the cap gene may be selected from an AAV with a serotype selected from the group consisting of AAV1, AAV2, AAV-, AAV4, AAV5, AAV6, AAV7, AAV8, AAV9, AAV10, AAV11, AAV12, AAVrh8, AAVrh10, Anc80L65, including variants or hybrids thereof (e.g., capsid hybrids of two or more serotypes). The cell may be infected at a combined multiplicity of infection (MOI) of between 3 and 14. The first herpesvirus and the second herpesvirus may be viruses selected from the group consisting of: cytomegalovirus (CMV), herpes simplex (HSV) and varicella zoster (VZV) and epstein barr virus (EBV). The herpesvirus may be replication defective. The co-infection may be simultaneous.

A method for producing recombinant AAV viral particles in a mammalian cell may comprise co-infecting a suspension cell with a first recombinant herpesvirus comprising a nucleic acid encoding an AAV rep and an AAV cap gene each operably linked to a promoter; and a second recombinant herpesvirus comprising a GJB2 gene construct, and a promoter operably linked to said GJB2 gene construct; and allowing the cell to propagate, thereby producing the recombinant AAV viral particles, whereby the number of viral particles produced is equal to or greater than the number of viral particles grown in an equal number of cells under adherent conditions. The cell may be HEK-293 (293), Vero, RD, BHK-21, HT-1080, A549, Cos-7, ARPE-19, and MRC-5. The cap gene may be selected from an AAV with a serotype selected from the group consisting of AAV1, AAV2, AAV3, AAV4, AAV5, AAV6, AAV7, AAV8, AAV9, AAV10, AAV11, AAV12, AAVrh8, AAVrh10, Anc80L65, including variants or hybrids thereof (e.g., capsid hybrids of two or more serotypes). The cell may be infected at a combined multiplicity of infection (MOI) of between 3 and 14. The first herpesvirus and the second herpesvirus may be viruses selected from the group consisting of: cytomegalovirus (CMV), herpes simplex (HSV) and varicella zoster (VZV) and epstein barr virus (EBV). The herpesvirus may be replication defective. The co-infection may be simultaneous.

A method for delivering a nucleic acid sequence encoding a therapeutic protein to a suspension cell, the method comprising: co-infecting the BHK cell with a first recombinant herpesvirus comprising a nucleic acid encoding an AAV rep and an AAV cap gene each operably linked to a promoter; and a second herpesvirus comprising a GJB2 gene construct, wherein the gene of interest comprises a therapeutic protein coding sequence, and a promoter operably linked to said GJB2 gene; and wherein said cell is infected at a combined multiplicity of infection (MOI) of between 3 and 14; and allowing the virus to infect the cell and express the therapeutic protein, thereby delivering the nucleic acid sequence encoding the therapeutic protein to the cell. The cell may be HEK-293 (293), Vero, RD, BHK-21, HT-1080, A549, Cos-7, ARPE-19, and MRC-5. See, e.g., U.S. Pat. No. 9,783,826.

Methods of Treatment

AAV and Gene Therapy

Gene therapy refers to treatment of inherited or acquired diseases by replacing, altering, or supplementing a gene responsible for the disease. It is achieved by introduction of a corrective gene or genes into a host cell, generally by means of a vehicle or vector. Gene therapy using rAAV holds great promise for the treatment of many diseases. A method of producing recombinant adeno-associated virus (rAAV), and in particular producing large quantities of recombinant AAV, to support treatment of genetic hearing loss are described herein.

To date more than 500 gene therapy clinical trials have been conducted worldwide. Efforts to use rAAV as a vehicle for gene therapy hold promise for its applicability as a treatment for human diseases. Already, some success has been achieved pre-clinically, using recombinant AAV (rAAV) for the delivery and long-term expression of introduced genes into cells in animals, including clinically important non-dividing cells of the brain, liver, skeletal muscle and lung. In some tissues, AAV vectors have been shown to integrate into the genome of the target cell. Hirata, et al. 2000, *J. of Virology* 74:4612-4620.

An additional advantage of rAAV is its ability to perform this function in non-dividing cell types including hepatocytes, neurons and skeletal myocytes. rAAV has been used successfully as a gene therapy vehicle to enable expression of erythropoietin in skeletal muscle of mice (Kessler, et al. 1996), tyrosine hydroxylase and aromatic amino acid decarboxylase in the CNS in monkey models of Parkinson disease (Kaplitt, et al. 1994) and Factor IX in skeletal muscle and liver in animal models of hemophilia. At the clinical level, the rAAV vector has been used in human clinical trials to deliver the CFTR gene to cystic fibrosis patients and the Factor IX gene to hemophilia patients (Flotte, et al. 1998; Wagner, et al. 1998), Further, AAV is a helper-dependent DNA parvovirus, which is not associated with disease in humans or mammals (Berns and Bohensky, 1987, Advances in Virus Research, Academic Press Inc, 32:243-307). Accordingly, one of the most important attributes of AAV vectors is their safety profile in phase I clinical trials.

AAV gene therapy has been carried out in a number of different pathological settings and to treat a various diseases and disorders. For example, in a phase I study, administration of an AAV2-FIX vector into the skeletal muscle of eight hemophilia B subjects proved safe and achieved local gene transfer and Factor IX expression for at least 10 months after vector injection (Jiang, et al. *Mol Ther.* 14 (3):452-5 2006), a phase I trial of intramuscular injection of a recombinant adeno-associated virus alpha 1-antitrypsin (rAAV2-CB-hAAT) gene vector to AAT-deficient adults has been described previously (Flotte, et al. *Hum Gene Ther.* 2004 15(1):93-128), and in another clinical trial AAV-GAD gene therapy of the subthalamic nucleus has been shown to be safe and well tolerated by patients with advanced Parkinson's disease (Kaplitt et al. Lancet. 200723; 369(9579): 2097-105).

The GJB2 AAV construct provides a gene therapy vehicle for the treatment of DFNB1 deafness phenotype. The GJB2 AAV gene therapy construct and methods of use described herein provides a therapy for DFNB1 deafness, a long-felt unmet need as there are no gene therapy-based treatments available for patients.

GJB2/Connexin 26 (Cx26) and Genetic Hearing Loss

Methods are provided herein that can be used to treat a hearing disorder or to prevent hearing loss (or further hearing loss) in a subject. Delivery of one or more of the nucleic acids described herein to cells within the inner ear, e.g., in the cochlea (or cells of the cochlea or cochlear cells) can be used to treat hearing disorders, which are typically defined by partial hearing loss or complete deafness.

According to some embodiments, methods are provided herein that employ GJB2 AAV-based gene therapy for treating non-syndromic hearing loss and deafness characterized by congenital non-progressive mild-to-profound sensorineural hearing impairment. The GJB2 AAV gene therapy construct and methods of use described herein provide the first and only instance of a long term (e.g., lifelong) therapy for correcting congenital deafness by gene supplementation. Importantly, the GJB2 AAV gene therapy construct and methods of use described herein would preserve natural hearing, while cochlear transplants do not.

The methods described herein allow for the production of recombinant AAV viral particles in a mammalian cell comprises co-infecting a mammalian cell capable of growing in suspension with a first recombinant herpesvirus and a second recombinant herpesvirus comprising a GJB2 gene construct that has therapeutic value in the treatment of genetic deafness.

GJB2 codes for the major gap junction protein Connexin 26 (Cx26), which, in association with other gap junction proteins, provides an extensive network allowing for intercellular coupling among non-sensory cells in the cochlea. However, the molecular mechanisms of how GJB2 mutations cause genetic hearing loss is not completely understood. It is known that loss of GJB2 causes death of various cell types in the inner ear following onset of hearing, suggesting its relevance during cochlear development. Furthermore, GJB2/Cx26 is hypothesized to be essential for the formation of a gap junction network required for normal hearing by maintaining potassium gradient homeostasis in the Organ of Corti. Individuals with autosomal recessive mutations in GJB2 manifest the DFNB1 deafness phenotype, and this accounts for nearly half of all cases of genetic hearing loss, with a prevalence of about 2-3 in every 1000 births.

This invention represents a novel rAAV-based gene therapy for treating or preventing genetic hearing loss due to GJB2 mutation, accounting for approximately 45% of all cases of congenital deafness. The rAAV constructs detailed in this invention will correspond to pre-lingual or post-lingual therapies for the prevention or treatment of both autosomal recessive GJB2 mutants (DFNB1) and autosomal dominant GJB2 mutants (DFNA3A), and administered by whatever method is necessary for intracochlear delivery. The gene constructs described herein may be used in methods and/or compositions to treat and/or prevent DFNB1 deafness.

According to some embodiments, the GJB2 AAV gene therapy is administered before the subject has developed hearing loss. According to some embodiments, the subject is diagnosed with DFNB1 by molecular genetic testing to identify deafness-causing mutations in GJB2. According to some embodiments, the subject has a family member with nonsyndromic hearing loss and deafness. According to some embodiments, the subject is a child. According to some embodiments, the subject is an infant.

The rAAV constructs described herein transduce inner ear cells, e.g. cochlear cells, with greater efficiency than do conventional AAV vectors. According to some embodiments, the compositions and methods described herein enable the highly efficient delivery of nucleic acids to inner ear cells, e.g., cochlear cells. According to some embodiments, the compositions and methods described herein enable the delivery to, and expression of, a transgene in at least 50% (e.g., at least 50, 55, 60, 65, 70, 75, 80, 85, 90, 91, 92, 93, 94, 95, 96, 97, 98, or 99%) of inner hair cells or delivery to, and expression in, at least 50% (e.g., at least 50, 55, 60, 65, 70, 75, 80, 85, 90, 91, 92, 93, 94, 95, 96, 97, 98, or 99) of outer hair cells. According to some embodiments, the compositions and methods described herein enable the delivery to, and expression of, a transgene in at least 70% (e.g., at least 70, 75, 80, 85, 90, 91, 92, 93, 94, 95, 96, 97, 98, or 99%) of inner hair cells or delivery to, and expression in, at least 70% (e.g., at least 70, 75, 80, 85, 90, 91, 92, 93, 94, 95, 96, 97, 98, or 99) of outer hair cells.

According to some embodiments, the nucleic acid sequences described herein are directly introduced into a cell, where the nucleic acid sequences are expressed to produce the encoded product, prior to administration in vivo of the resulting recombinant cell. This can be accomplished by any of numerous methods known in the art, e.g., by such methods as electroporation, lipofection, calcium phosphate mediated transfection.

Similar to the currently employed cochlear implant, GJB2 gene therapy would provide a lifetime solution, though unlike cochlear implants, with the added benefit of preserving natural hearing.

Pharmaceutical Compositions

According to some aspects, the disclosure provides pharmaceutical compositions comprising any of the vectors described herein, optionally in a pharmaceutically acceptable excipient.

As is well known in the art, pharmaceutically acceptable excipients are relatively inert substances that facilitate administration of a pharmacologically effective substance and can be supplied as liquid solutions or suspensions, as emulsions, or as solid forms suitable for dissolution or suspension in liquid prior to use. For example, an excipient can give form or consistency, or act as a diluent. Suitable excipients include but are not limited to stabilizing agents, wetting and emulsifying agents, salts for varying osmolarity, encapsulating agents, pH buffering substances, and buffers. Such excipients include any pharmaceutical agent suitable for direct delivery to the ear (e.g., inner ear or middle ear) which may be administered without undue toxicity. Pharmaceutically acceptable excipients include, but are not limited to, sorbitol, any of the various TWEEN compounds, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in REMINGTON'S PHARMACEUTICAL SCIENCES (Mack Pub. Co., N.J. 1991).

According to some embodiments, the pharmaceutical composition comprises one or more of BSST, PBS or BSS.

According to some embodiments, the pharmaceutical composition further comprises histidine buffer.

According to some embodiments, the pharmaceutical composition further comprises poloxamer buffer.

According to some embodiments, delivery vehicles (e.g., polymers) are available that facilitate the transfer of agents across the tympanic membrane and/or through the round window, and any such delivery vehicles can be used to deliver the viruses described herein. See, for example, Arnold et al., 2005, Audiol. Neurootol., 10:53-63, incorporated by reference in its entirety herein.

Although not required, the compositions may optionally be supplied in unit dosage form suitable for administration of a precise amount.

According to some embodiments, the compositions are administered to a subject prior to cochlear implant.

Methods of Administration

Generally, the compositions described herein are formulated for administration to the ear. According to some embodiments, the compositions are formulated for administration to cells in the organ of Corti (OC) in the cochlea. Cells in the OC include hensen's cells, deiters' cells, pillar cells, inner phalangeal cells and/or outer phalangeal cells/border cells. The OC includes two classes of sensory hair cells: inner hair cells (IHCs), which convert mechanical information carried by sound into electrical signals transmitted to neuronal structures and outer hair cells (OHCs) which serve to amplify and tune the cochlear response, a process required for complex hearing function. According to some embodiments, the compositions are formulated for administration to the IHCs and/or the OHCs.

Injection to the cochlear duct, which is filled with high potassium endolymph fluid, could provide direct access to hair cells. However, alterations to this delicate fluid environment may disrupt the endocochlear potential, heightening the risk for injection-related toxicity. The perilymph-filled spaces surrounding the cochlear duct, scala tympani and scala vestibuli, can be accessed from the middle ear, either through the oval or round window membrane. The round window membrane, which is the only non-bony opening into the inner ear, is relatively easily accessible in many animal models and administration of viral vector using this route is well tolerated. In humans, cochlear implant placement routinely relies on surgical electrode insertion through the round window membrane. Intratympanic injection of therapeutic agents is the technique of injecting an agent behind the tympanic membrane into the middle and/or inner ear. According to some embodiments, the compositions are administered by intratympanic injection into the inner ear and/or into the middle ear. According to some embodiments, the compositions are administered by injection via the round window membrane. According to some embodiments, the compositions are administered directly onto the round window membrane via transtympanic injection. According to some embodiments, the compositions are administered by injection into the scala tympani or scala media. According to some embodiments, the delivery system is a syringe and needle apparatus that is capable of piercing the tympanic membrane and directly accessing the round window membrane. According to some embodiments, the delivery system is an ear dropper. According to some embodiments, the delivery system is as a topical formulation. According to some embodiments, the compositions are administered during a surgical procedure, e.g. during a cochleostomy or during a canalostomy. For some routes of administration, e.g. for injection into the inner ear and/or into the middle ear a sustained release system can be used.

By safely and effectively transducing cochlear cells as described herein, the methods of the invention may be used to treat an individual e.g., a human, wherein the transduced cells produce GJB2 in an amount sufficient to restore hearing or vestibular for an extended period of time (e.g., months, years, decades, a lifetime)

According to the methods of treatment of the present invention, the volume of vector delivered may be determined based on the characteristics of the subject receiving the treatment, such as the age of the subject and the volume of the area to which the vector is to be delivered. According to some embodiments, the volume of the composition injected is between about 10 µl to about 1000 µl, or between about between about 100 µl to about 1000 µl, or between about between about 100 µl to about 500 µl, or between about 500 µl to about 1000 µl. According to some embodiments, the volume of the composition injected is more than about any one of 1 µl, 2 µl, 3 µl, 4 µl, 5 µl, 6 µl, 7 µl, 8 µl, 9 µl, 10 µl, 15 µl, 20 µl, 25 µl, 50 µl, 75 µl, 100 µl, 200 µl, 300 µl, 400 µl, 500 µl, 600 µl, 700 µl, 800 µl, 900 µl, or 1 mL, or any amount there between.

According to the methods of treatment of the present disclosure, the concentration of vector that is administered may differ depending on production method and may be chosen or optimized based on concentrations determined to be therapeutically effective for the particular route of administration. According to some embodiments, the concentration in vector genomes per milliliter (vg/ml) is selected from the group consisting of about $10^8$ vg/ml, about $10^9$ vg/ml, about $10^{10}$ vg/ml, about $10^{11}$ vg/ml, about $10^{12}$ vg/ml, about $10^{13}$ vg/ml, and about $10^{14}$ vg/ml. In preferred embodiments, the concentration is in the range of $10^{10}$ vg/ml-$10^{13}$ vg/ml in a volume of about 0.1 mL, about 0.2 mL, about 0.4 mL, about 0.6 mL, about 0.8 mL, and about 1.0 mL.

The effectiveness of the compositions described herein can be monitored by several criteria. For example, after treatment in a subject using methods of the present disclosure, the subject may be assessed for e.g., an improvement and/or stabilization and/or delay in the progression of one or more signs or symptoms of the disease state by one or more clinical parameters including those described herein. Examples of such tests are known in the art, and include objective as well as subjective (e.g., subject reported) measures. According to some embodiments, these tests may include, but are not limited to, auditory brainstem response (ABR) measurements, speech perception, mode of communication, and subjective assessments of aural response recognition.

According to some embodiments, subjects exhibiting nonsyndromic hearing loss and deafness (DFNB1) were first tested to determine their threshold hearing sensitivity over the auditory range. The subjects were then treated with the rAAV compositions described herein. Changes in the threshold hearing levels as a function of frequency measured in dB are determined. According to some embodiments, an improvement in hearing is determined as a 10 dB to 50 dB improvement in threshold hearing sensitivity in at least one ear at mid to high frequencies. According to some embodiments, an improvement in hearing is determined as a 10 dB to 30 dB improvement in threshold hearing sensitivity in at least one ear at mid to high frequencies. According to some embodiments, an improvement in hearing is determined as a 10 dB to 20 dB improvement in threshold hearing sensitivity in at least one ear at mid to high frequencies.

In Vivo Mouse Model for Hereditary Deafness

According to some embodiments, an in vivo mouse model is used to assess the effectiveness of the compositions described herein. One example of an in vivo mouse model is a Connexin26/GJB2 knock out transgenic mouse as a disease model, such as the one detailed in Takada et al., Hearing Research vol. 309, 2014, incorporated by reference in its entirety herein.

Further embodiments of the present invention will now be described with reference to the following examples. The examples contained herein are offered by way of illustration and not by any way of limitation.

EXAMPLES

Example 1. Methods

The invention was performed using, but not limited to, the following methods. The methods as described herein are set forth in PCT Application No. PCT/US2007/017645, filed on Aug. 8, 2007, entitled Recombinant AAV Production in Mammalian Cells, which claims the benefit of U.S. application Ser. No. 11/503,775, entitled Recombinant AAV Production in Mammalian Cells, filed Aug. 14, 2007, which is a continuation-in-part of U.S. application Ser. No. 10/252,182, entitled High Titer Recombinant AAV Production, filed Sep. 23, 2002, now U.S. Pat. No. 7,091,029, issued Aug. 15, 2006. The contents of all the aforementioned applications are hereby incorporated by reference in their entirety.

rHSV Co-Infection Method

The rHSV co-infection method for recombinant adeno-associated virus (rAAV) production employs two ICP27-deficient recombinant herpes simplex virus type 1 (rHSV-1) vectors, one bearing the AAV rep and cap genes (rHSV-rep2capX, with "capX" referring to any of the AAV serotypes), and the second bearing the gene of interest (GOI) cassette flanked by AAV inverted terminal repeats (ITRs). Although the system was developed with AAV serotype 2 rep, cap, and ITRs, as well as the humanized green fluorescent protein gene (GFP) as the transgene, the system can be employed with different transgenes and serotype/pseudotype elements.

Mammalian cells are infected with the rHSV vectors, providing all cis and trans-acting rAAV components as well as the requisite helper functions for productive rAAV infection. Cells are infected with a mixture of rHSV-rep2capX and rHSV-GOI. Cells are harvested and lysed to liberate rAAV-GOI, and the resulting vector stock is titered by the various methods described below.

DOC-Lysis

At harvest, cells and media are separated by centrifugation. The media is set aside while the cell pellet is extracted with lysis buffer (20 mM Tris-HCl, pH 8.0, 150 mM NaCl) containing 0.5% (w/v) deoxycholate (DOC) using 2 to 3 freeze-thaw cycles, which extracts cell-associated rAAV. In some instances, the media and cell-associated rAAV lysate is recombined.

In Situ Lysis

An alternative method for harvesting rAAV is by in situ lysis. At the time of harvest, $MgCl_2$ is added to a final concentration of 1 mM, 10% (v/v) Triton X-100 added to a final concentration of 1% (v/v), and Benzonase is added to a final concentration of 50 units/mL. This mixture is either shaken or stirred at 37° C. for 2 hours.

Quantitative Real-Time PCR to Determine DRP Yield

The DNAse-resistant particle (DRP) assay employs sequence-specific oligonucleotide primers and a dual-labeled hybridizing probe for detection and quantification of the amplified DNA sequence using real-time quantitative polymerase chain reaction (qPCR) technology. The target sequence is amplified in the presence of a fluorogenic probe which hybridizes to the DNA and emits a copy-dependent fluorescence. The DRP titer (DRP/mL) is calculated by direct comparison of relative fluorescence units (RFUs) of the test article to the fluorescent signal generated from known plasmid dilutions bearing the same DNA sequence. The data generated from this assay reflect the quantity of packaged viral DNA sequences, and are not indicative of sequence integrity or particle infectivity.

Green-Cell Infectivity Assay to Determine Infectious Particle Yield (rAAV-GFP Only)

Infectious particle (ip) titering is performed on stocks of rAAV-GFP using a green cell assay. C12 cells (a HeLa derived line that expressed AAV2 Rep and Cap genes—see references below) are infected with serial dilutions of rAAV-GFP plus saturating concentrations of adenovirus (to provide helper functions for AAV replication). After two to three days incubation, the number of fluorescing green cells (each cell representing one infectious event) are counted and used to calculate the ip/mL titer of the virus sample.

Clark K R et al. described recombinant adenoviral production in Hum. Gene Ther. 1995. 6:1329-1341 and Gene Ther. 1996. 3:1124-1132, both of which are incorporated by reference in their entireties herein.

$TCID_{50}$ to Determine rAAV Infectivity

Infectivity of rAAV particles harboring a gene of interest (rAAV-GOI) was determined using a tissue culture infectious dose at 50% ($TCID_{50}$) assay. Eight replicates of rAAV were serially diluted in the presence of human adenovirus type 5 and used to infect HeLaRC32 cells (a HeLa-derived cell line that expresses AAV2 rep and cap, purchased from ATCC) in a 96-well plate. At three days post-infection, lysis buffer (final concentrations of 1 mM Tris-HCl pH 8.0, 1 mM EDTA, 0.25% (w/v) deoxycholate, 0.45% (v/v) Tween-20, 0.1% (w/v) sodium dodecyl sulfate, 0.3 mg/mL Proteinase K) was added to each well then incubated at 37° C. for 1 h, 55° C. for 2 h, and 95° C. for 30 min. The lysate from each well (2.5 µL aliquot) was assayed in the DRP qPCR assay described above. Wells with Ct values lower than the value of the lowest quantity of plasmid of the standard curve were scored as positive. $TCID_{50}$ infectivity per mL ($TCID_{50}$/mL) was calculated based on the Karber equation using the ratios of positive wells at 10-fold serial dilutions.

Cell Lines and Viruses

Production of rAAV vectors for gene therapy is carried out in vitro, using suitable producer cell lines such as HEK293 cells (293). Other cell lines suitable for use in the invention include Vero, RD, BHK-21, HT-1080, A549, Cos-7, ARPE-19, and MRC-5.

Mammalian cell lines were maintained in Dulbecco's modified Eagle's medium (DMEM, Hyclone) containing 2-10% (v/v) fetal bovine serum (FBS, Hyclone) unless otherwise noted. Cell culture and virus propagation were performed at 37° C., 5% CO2 for the indicated intervals.

Infection Cell Density

Cells can be grown to various concentrations including, but not limited to at least about, at most about, or about $1 \times 10^6$ to $4 \times 10^6$ cells/mL. The cells can then be infected with recombinant herpesvirus at a predetermined MOI.

Example 2. Cloning of the GJB2 Expression Constructs

Genomic constructs were variant iterations of the following: ITR(5')-Promoter-GJB2.tag-3'UTR-ITR(3')*; variants for each element are further specified below, including references to their conception and experimental development:

ITR elements, including ITR(5') and ITR(3')*: inverted terminal repeat (ITR) elements of 143-nucleotides in length derived from AAV2. For normal capacity—i.e. single stranded (ss)—AAV-genomes, ITR(3') will be identical to the ITR(5') in sequence and length; for self-complimentary (sc)AAV (i.e. half capacity) genomes, ITR(3') will have a 31-nucleotide deletion corresponding to the Trs region ("ITRΔtrs" for short), resulting in a truncated length of 113-nucleotides, while the ITR(5') remains the original 143 nucleotide length.

Promoter: CBA, smCBA*, EF1a*, CASI*, GFAP, GJB2-128 bp*, GJB2-539 bp*, GJB2-1000 bp*, or a combination promoter (combining 2-3 of the listed promoters).

FIG. 3 shows the nucleic acid sequence of the CBA promoter (SEQ ID NO. 1). FIG. 4 shows the nucleic acid sequence of the EF1a promoter (SEQ ID NO. 2). FIG. 5 shows the nucleic acid sequence of the CASI promoter (SEQ ID NO. 3). FIG. 6 shows the nucleic acid sequence of the smCBA promoter (SEQ ID NO. 4). FIG. 7 shows the nucleic acid sequence of the GFAP promoter (SEQ ID NO. 5). FIG. 8 shows the nucleic acid sequence of the GJB2 promoter (SEQ ID NO. 6).

GJB2 (gene)*: The GJB2 gene reference sequence can be found at NG_008358.1 (ncbi.nlm.nih.gov/nuccore/NG_008358.1). GJB2 genes used in the described experiments were as follows: wtGJB2 (wildtype human GJB2 gene, human codon optimized GJB2(co1-9) (9 codon optimized human GJB2 cDNA variants (hGJB2co1, hGJB2co2, hGJB2co3, hGJB2co4, hGJB2co5, hGJB2co6, hGJB2co7, hGJB2co8, hGJB2co9) or a hybridized codon optimized construct (co369GJB2); constructs may also contain C-terminal HA tag(27-nucleotide hemagglutinin). Design and development (of gene and tag elements); FIG. 10 shows the nucleic acid sequence of the human wild-type GJB2 (hGJB2wt) (SEQ ID NO. 10). FIG. 11 shows the nucleic acid sequence of the human codon optimized GJB2 (hGJB2co3) (SEQ ID NO. 11). FIG. 12 shows the nucleic acid sequence of the human codon optimized GJB2 (hGJB2co6) (SEQ ID NO. 12). FIG. 13 shows the nucleic acid sequence of the human codon optimized GJB2 (hGJB2co9) (SEQ ID NO. 13). FIG. 18 shows the nucleic acid sequence of the hybrid codon optimized construct (co369).

3'UTR elements, including WPRE*, SV40pA*, and DNA stuffer. FIG. 14 shows the nucleic acid sequence of an HA tag (SEQ ID NO. 14). FIG. 15 shows the nucleic acid sequence of Woodchuck Hepatitis Virus Posttranscriptional Regulatory Element (WPRE) (SEQ ID NO. 15). FIG. 16 shows the nucleic acid sequence of SV40 poly(A) (SEQ ID NO. 16). FIG. 17 shows the nucleic acid sequence of aSV40/bGH terminator sequence (SEQ ID NO. 17).

Elements marked by an asterisk (*) were also be used for the design of scAAV vector constructs.

Example 3. rAAV Vector for DFNB-1 Treatment

Components of an efficacious rAAV vector for DFNB-1 treatment include: a capsid that exhibits cochlear support cell tropism, a promoter that drives either strong-ubiquitous or moderate-strong cell-type specific transgene expression, and a transgene that stably encodes connexin-26 protein.

Capsid Selection

Figure 19B:
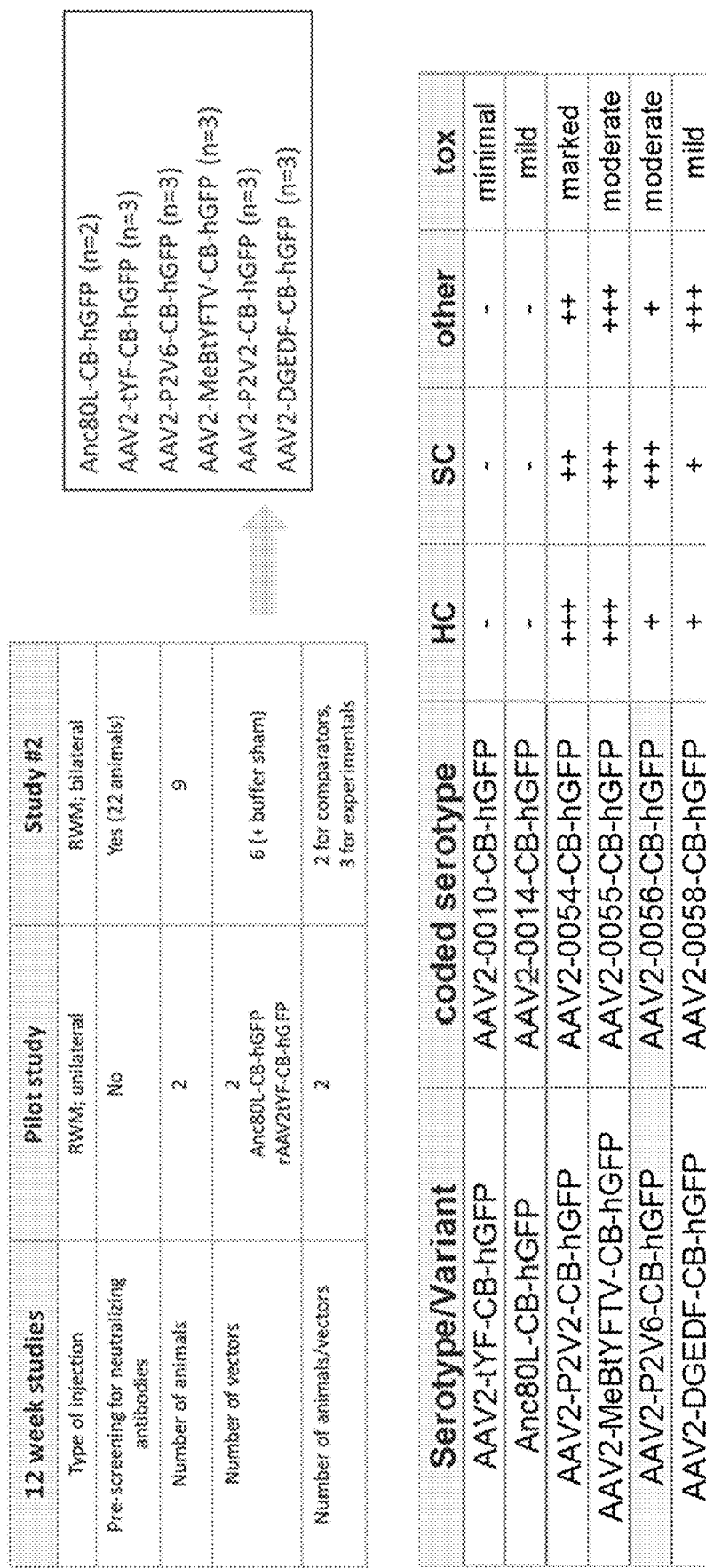
FIG. 19B shows a summary of GFP transduction in non-human primate (NHP) cochlea.

FIG. 19A and FIG. 19B summarizes data obtained from cochlea tropism studies that identified AAV2 variant capsids for use in GJB2 gene therapy. These previous studies entailed five separate studies, two in mouse, one in guinea pig, and two in non-human primates (NHP). In the rodent studies, an initial panel of AAV capsids, each containing CBA driven GFP reporter, were intracochlearly administered into the cochlea for and then tissues analyzed 2 weeks later to identify candidates with high tropism for various cochlear tissues of therapeutic interest (in this case, high tropism for support cells). From the rodent data, 4 capsid finalists were chosen and tested along with 2 comparator capsids in NHPs in a similar manner as rodents (except the in life was 12 weeks instead of 2). This data is summarized in the tables shown in FIG. 19A (for rodents) and FIG. 19B (for NHP). P2V2 was selected because it showcased a combination of positive features that made it more favorable than the other capsids: among these features were excellent support cell tropism, relatively low tropism for hair cells, and a low inflammatory outcome.

Figure 19C:
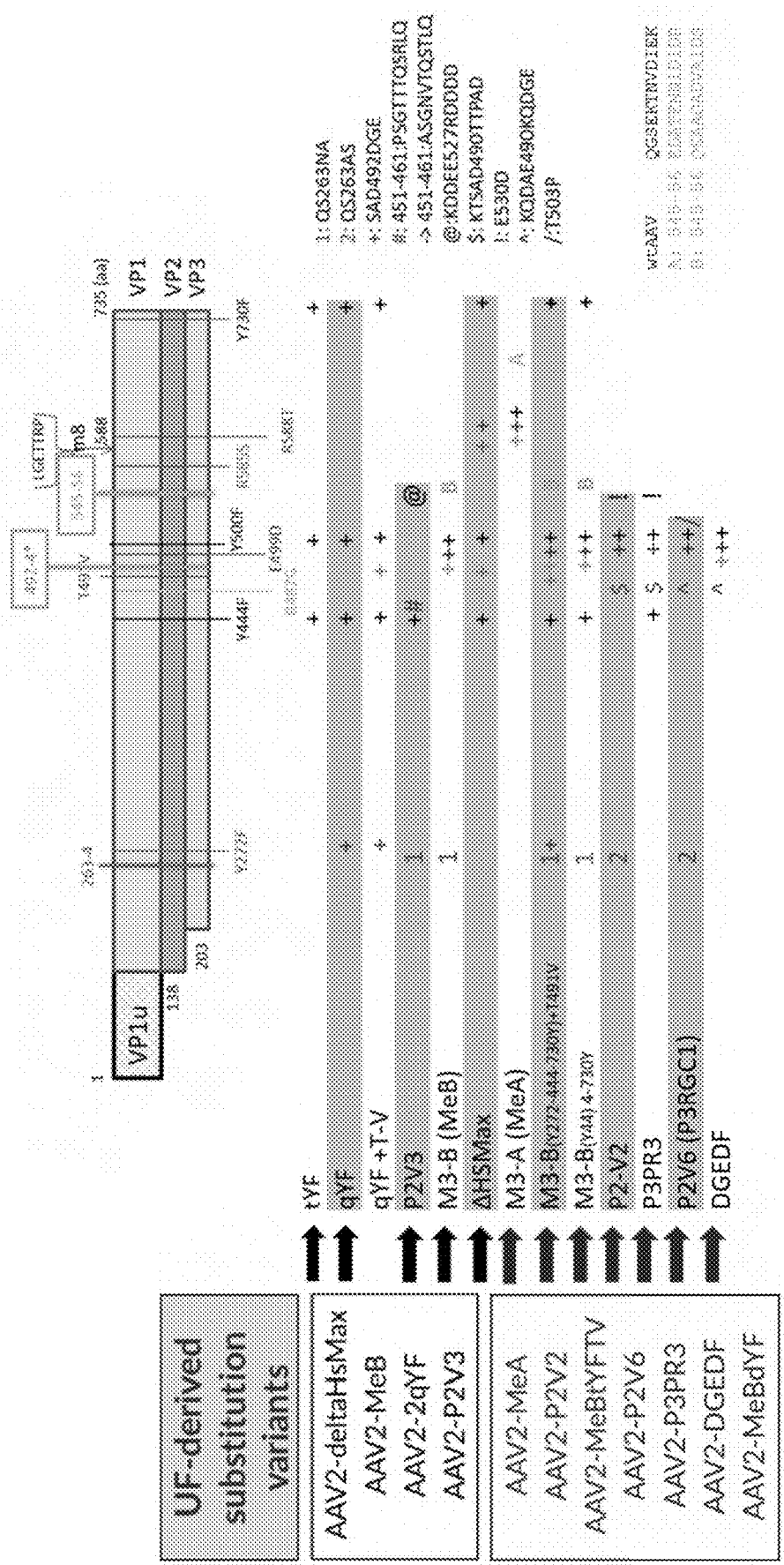
FIG. 19C depicts the various AAV2 capsid variants that were tested.

FIG. 19C depicts the various AAV2 capsid variants that were tested. From this work, AAV2-MeB, AAV2-P2V3, AAV2-P2V2 and AAV-P2V6 were identified as the top candidates for use in an rAAV vector for DFNB treatment.

Promoter Selection

Promoter development consisted of identification of strong-ubiquitous promoter sequences (CBA, smCBA, EF1a, CASI), as well as cochlear support cell-type specific promoters (GFAP and various length versions of the endogenous mammalian GJB2 promoter, including the 128-bp-long basal promoter of GJB2 (GJB2(128)), GJB2(539), GJB2 (1000)). The numbers in parentheses are base pair (bp) lengths, estimated from analysis of the UTR 5' to the GJB2 gene. While the true endogenous length of this promoter is not precisely known (i.e. the entire promoter has not been defined yet), these lengths were chosen based on predicted regions/motifs of the promoter. The 1000 bp length promoter is estimated to contain all the known functional regions of the greater GJB2 promoter (primarily core promoter plus transcription factor binding sites). The 128 bp length promoter represents the minimal "core" promoter—any further truncation would eliminate the promoter function altogether. The 539 bp length promoter was chosen as an intermediate between these two, to presumably serve as a promoter of "middle strength". Sequences for these promoters were synthesized commercially (Genscript), followed by in-house PCR amplification and extraction, resulting in promoter segments with compatible restriction site segments for insertion into a unique viral packaging vector containing an ampicillin selection cassette, AAV ITR segments, hGFP reporter gene, and SV40 poly A (pAAV-X-hGFP-pA).

Promoter constructs were transformed into high efficiency E. coli cells (SURE2) for amplification, and clones were selected for validation. Sanger sequencing (Genewiz) and restriction digests (with appropriate restriction sites (KpnI-MluI) to check for promoter insertion and ITR integrity) were performed to validate the promoter plasmids. Positive clones for each promoter construct were selected for subsequent experiments. Unique promoter constructs were tested for efficacy in driving hGFP expression via in vitro transfection of HEK-293 (control) or RT4 (high GJB2 expressing cell line) cells.

Figure 20:
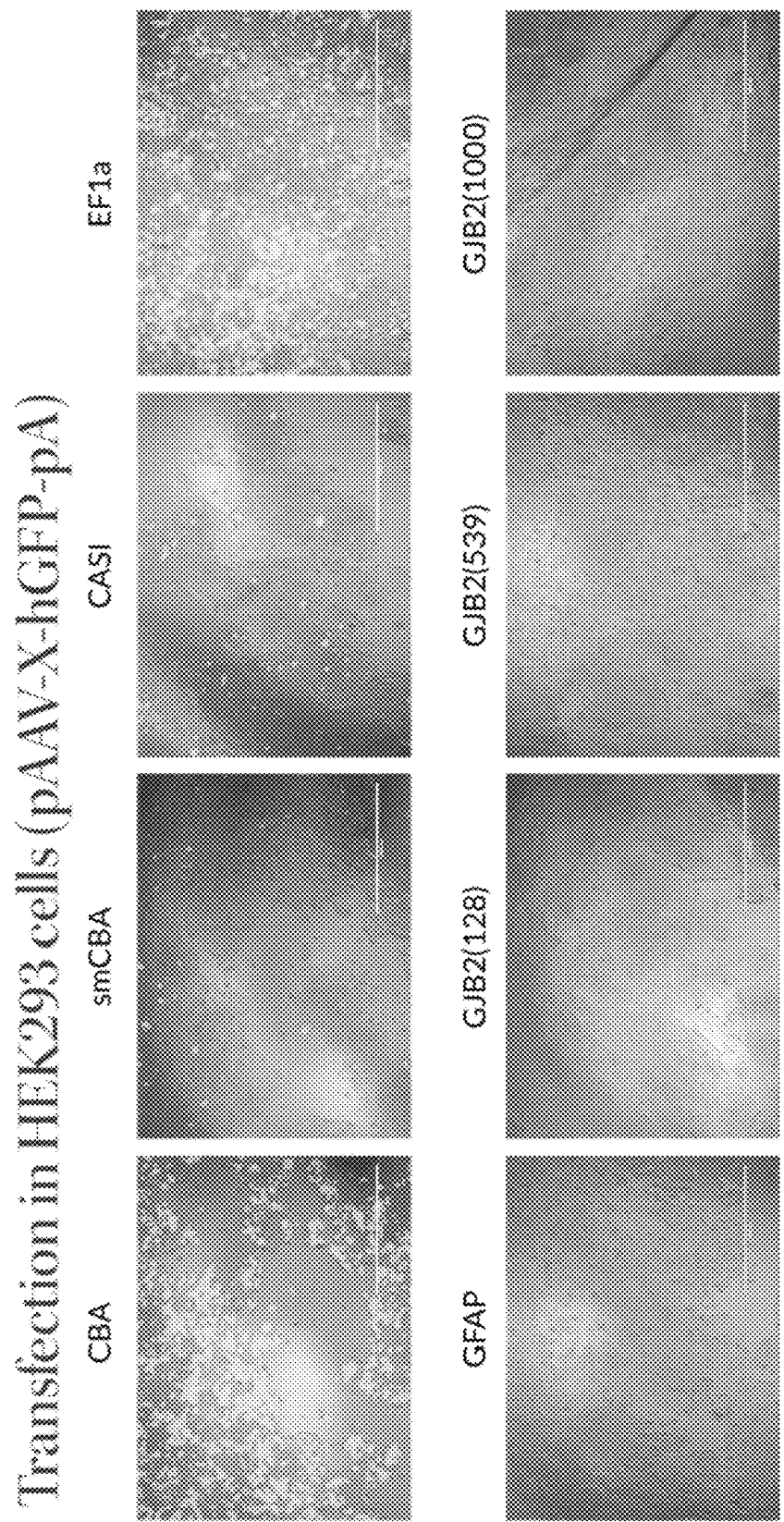
FIG. 20 shows GFP expression in HEK293 cells transfected with a pAAV-X-hGFP-pA vector, where X is a promoter being tested, selected from CBA, smCBA, CAST, EF1a, GFAP, GJB2(128), GJB2(539), GJB2(1000).
Figure 21:
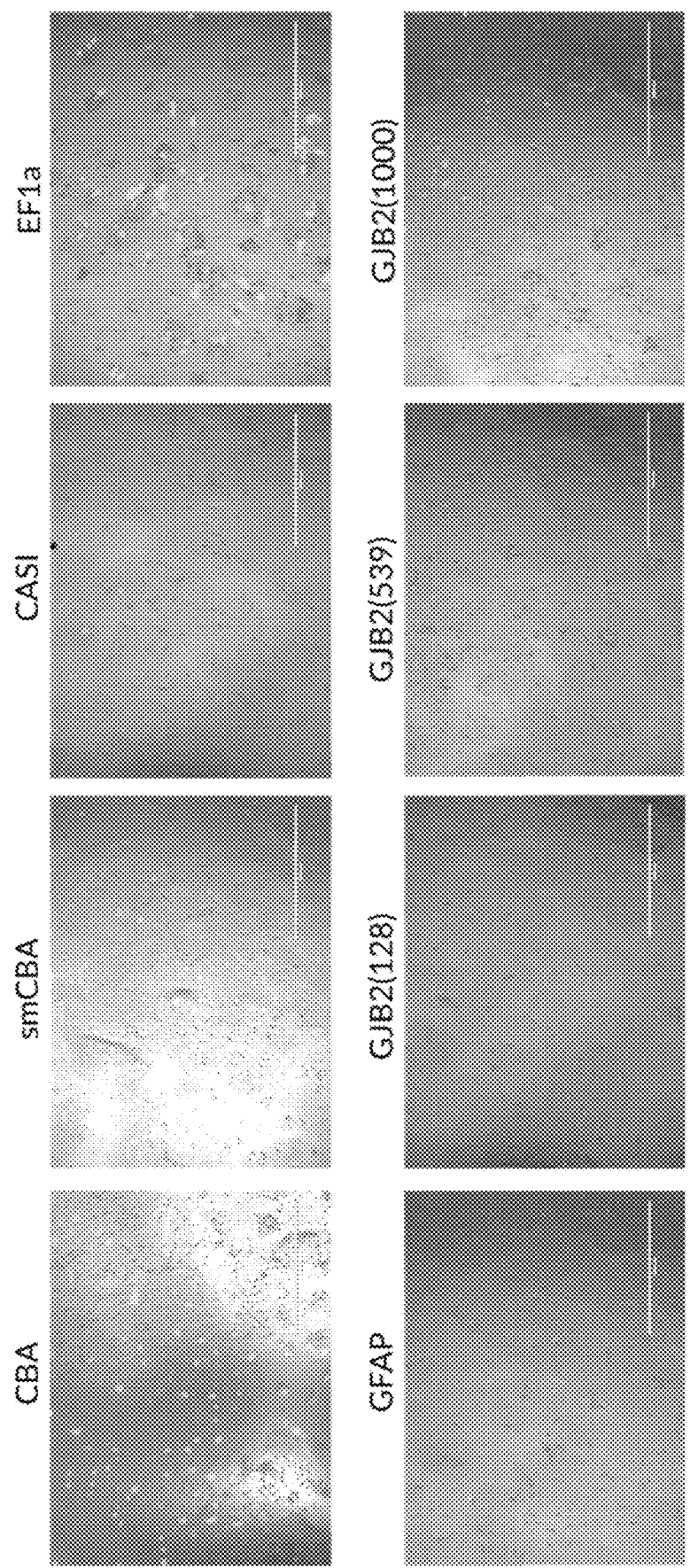
FIG. 21 shows GFP expression in RT4 cells transfected with a pAAV-X-hGFP-pA vector, where X is a promoter being tested, selected from CBA, smCBA, CASI, EF1a, GFAP, GJB2(128), GJB2(539), GJB2(1000).

Briefly, 1E5 cells in 400 μl media were seeded in a 48 well plate. 250 ng DNA at a 1:2 ratio with GeneXPlus was used for transfection. hGFP expression was determined at a 48-72 hour time point. FIG. 20 shows GFP expression in HEK293 cells transfected with a pAAV-X-hGFP-pA vector, where X is a promoter, selected from CBA, smCBA, CASI, EF1a, GFAP, GJB2(128), GJB2(539), GJB2(1000), as indicated. FIG. 21 shows GFP expression in RT4 cells transfected with a pAAV-X-hGFP-pA vector, where X is a promoter, selected from CBA, smCBA, CASI, EF1a, GFAP, GJB2(128), GJB2 (539), GJB2(1000), as indicated.

This data indicated that CBA and EF1a drive strong GFP expression in both cell lines, whereas GJB2(1000) moderately drove GFP expression in RT4 cells and slightly drove GFP expression in HEK293 cells. These results suggested that CBA and Ef1a promoters were strong promoters, while GJB2(1000) was a moderate-strong specific promoter.

Example 4. Codon Optimized GJB2 Vector Design and Synthesis

GJB2 transgene optimization consists of efforts to enhance protein expression, stability, and function. Codon optimized variants of GJB2 were synthesized and assessed for changes in protein expression versus wildtype (WT). Nine codon optimized variants were generated, each contained a 27 bp C-terminal HA tag as an alternative measure for protein expression, as well as a means for detection over endogenous protein. Each codon optimized variant contained unique optimizations (i.e., codon usage, GC content, stability of 5' mRNA structure, removal of RNA destabilizing sequences, etc.), generated from different algorithms (Genscript, Atum, and Blueheron Biotech).

In-house PCR amplification and extraction was performed, resulting in GJB2 transgene segments with compatible restriction sites (NotI) for insertion into a unique viral packaging vector containing an ampicillin selection cassette and AAV ITR segments. Following full synthesis, codon optimized constructs were transformed into high efficiency *E. coli* cells (SURE2) for amplification, and clones were selected for validation. Sanger sequencing (Genewiz) and restriction digests (with appropriate restriction sites to check for transgene insertion and ITR integrity) were performed to validate the codon optimized GJB2 plasmids.

Figure 22:
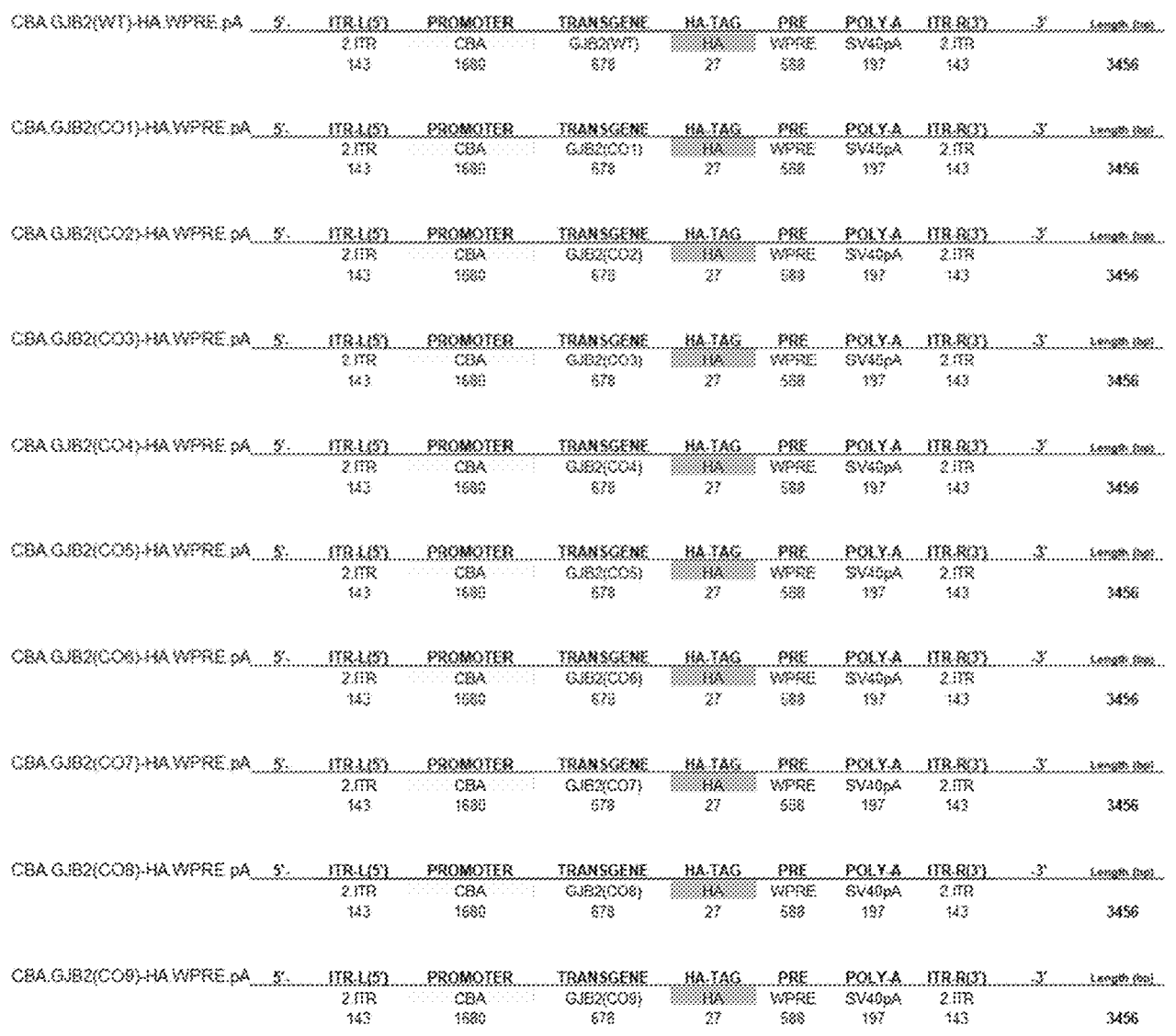

FIG. 22 depicts schematics of the codon optimized constructs (AAV-CBA-GJB2(X)-HA-WPRE-pA.

Figure 23A:
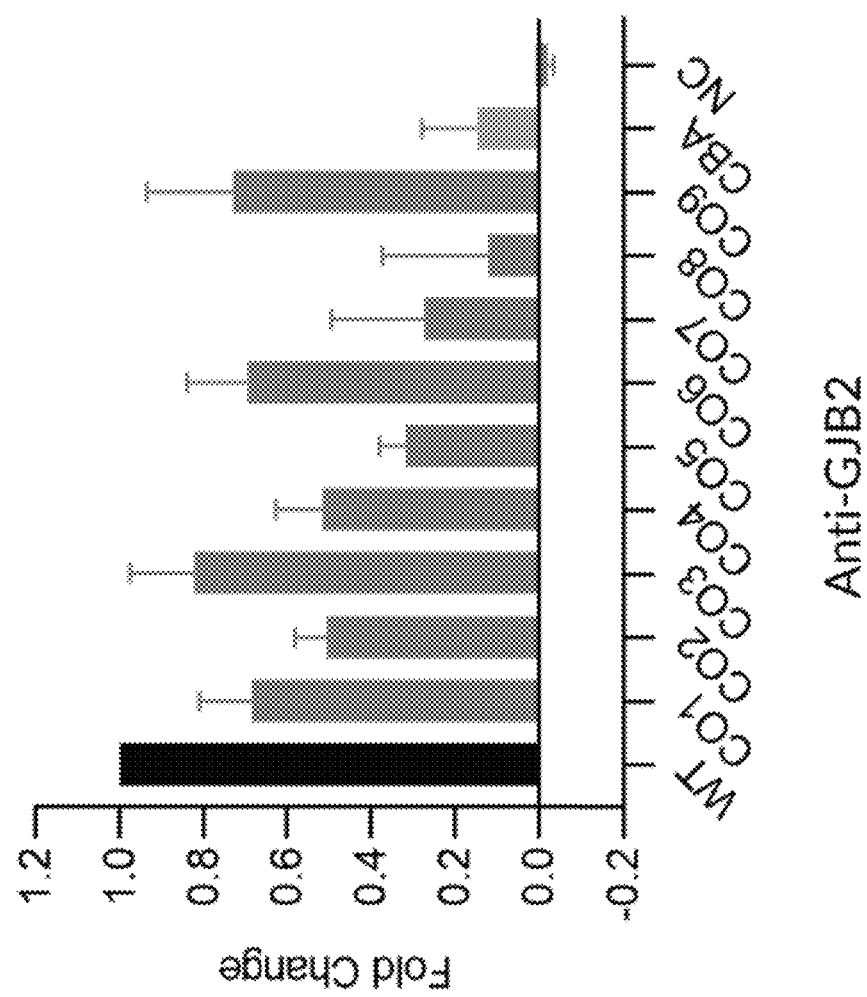
FIG. 23A and FIG. 23B are graphs that depict fold change of GJB2 and HA protein expression (respectively) of various GJB2 codon optimized constructs (AAV-CBA-GJB2(X)-HA-WPRE-pA) compared to control (WT) when assayed by ELISA.
Figure 23B:
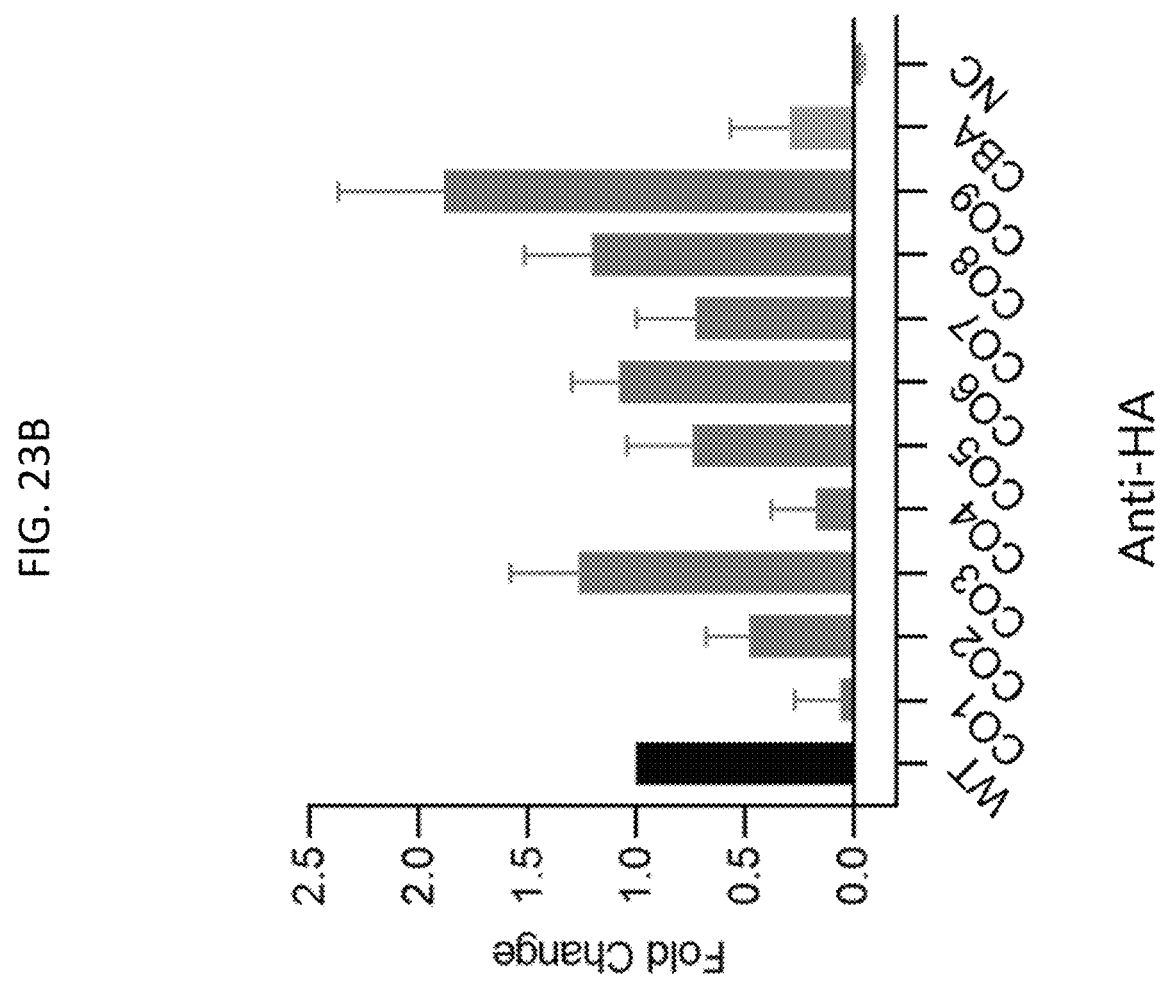
Figure 24A:
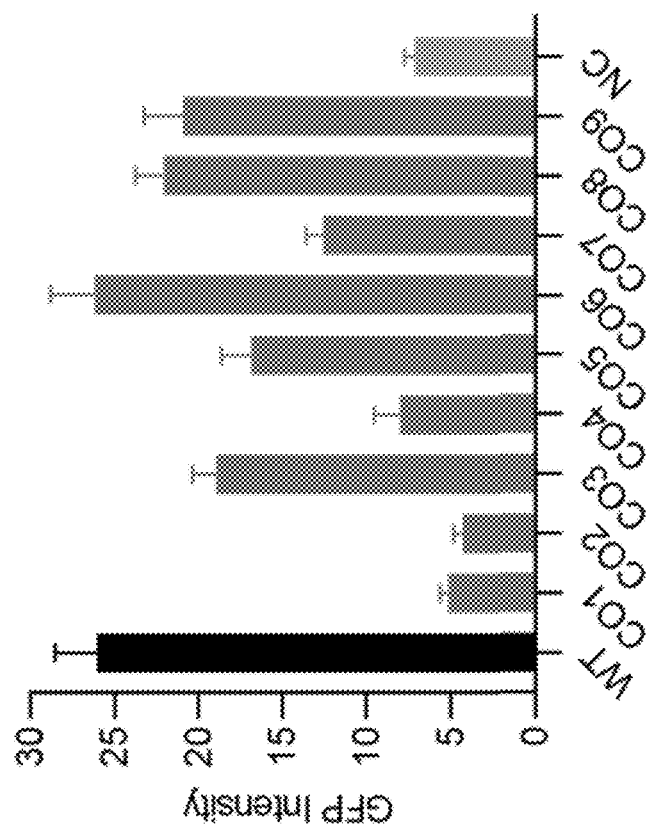
FIG. 24A is a graph that depicts quantification of immunofluorescence following anti-connexin 26 antibody (anti-CX26) staining, determined by green fluorescent protein (GFP) intensity.
Figure 24B:
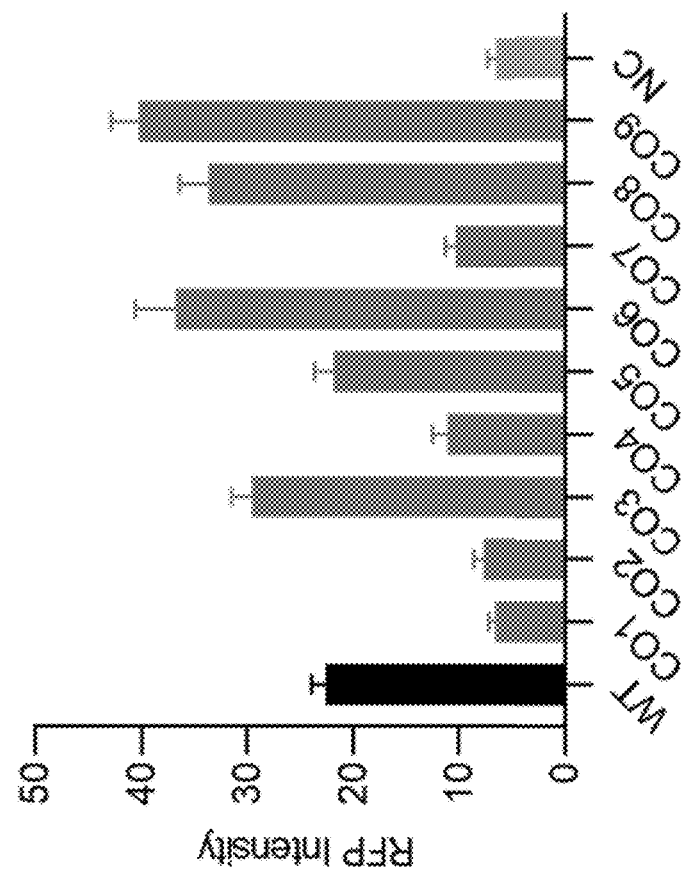
FIG. 24B is a graph that depicts quantification of immunofluorescence following anti-HA antibody, determined by red fluorescent protein (RFP) intensity.

Positive clones for each codon optimized construct were selected for subsequent experiments. To determine the best expressing codon optimized sequence (designated hGJBco1-hGJBco9), transgene expression experiments were performed and analyzed via in-cell ELISA, immunofluorescence, and western blotting. FIG. 23A and FIG. 23B show fold change of GJB2 and HA protein expression (respectively) of various GJB2 codon optimized constructs (AAV-CBA-GJB2(X)-HA-WPRE-pA) compared to control (WT) when assayed by ELISA. As shown in FIG. 23A, constructs comprising hGJBco3 (CO3), hGJBco6 (CO6) and hGJBco9 (CO9) showed comparable protein expression compared to WT when assayed with a connexin 26 mouse monoclonal antibody (ThermoFisher Scientific, CX-12H10). As shown in FIG. 23B, CO9 showed significantly higher protein expression when assayed with an HA mouse monoclonal antibody (ThermoFisher Scientific, #26183). Western blotting analysis showed that co9 had comparable expression to WT when assayed with connexin 26 mouse monoclonal antibody, and co2, co3, co5, co6, co8, and co9 showed comparable expression to WT when assayed with HA monoclonal antibody (not shown). Immunofluorescence data showed comparable results when assaying with a GJB2 and HA antibody, in which co3, co5, co6, co8, and co9 showed comparable/higher GJB2 expression compared to WT. Quantification of the immunofluorescence studies is shown in FIG. 24A for anti-connexin 26 antibody (anti-CX26) staining, determined by GFP intensity, and FIG. 24B for anti-HA staining, determined by RFP intensity.

Example 5. Codon Optimization Studies-Generation 2

Figure 25:
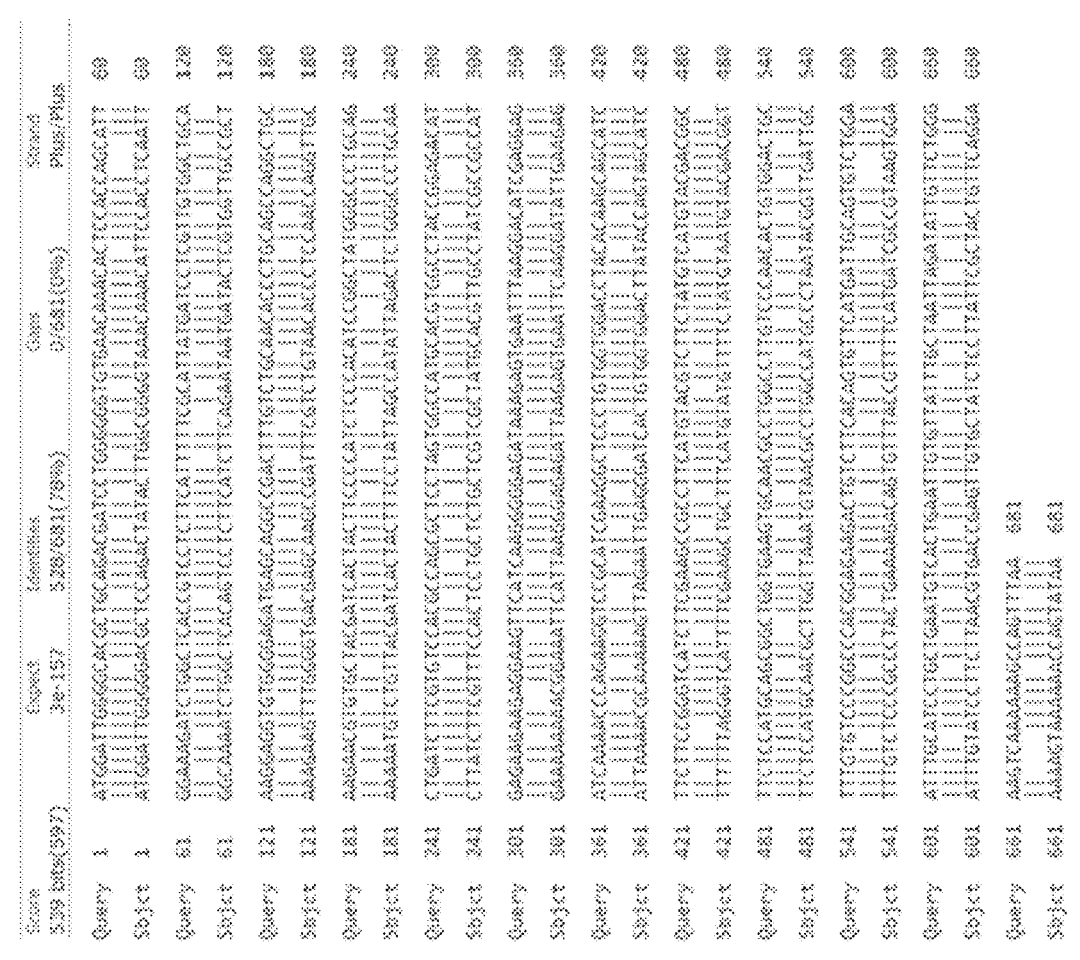
Figure 26:
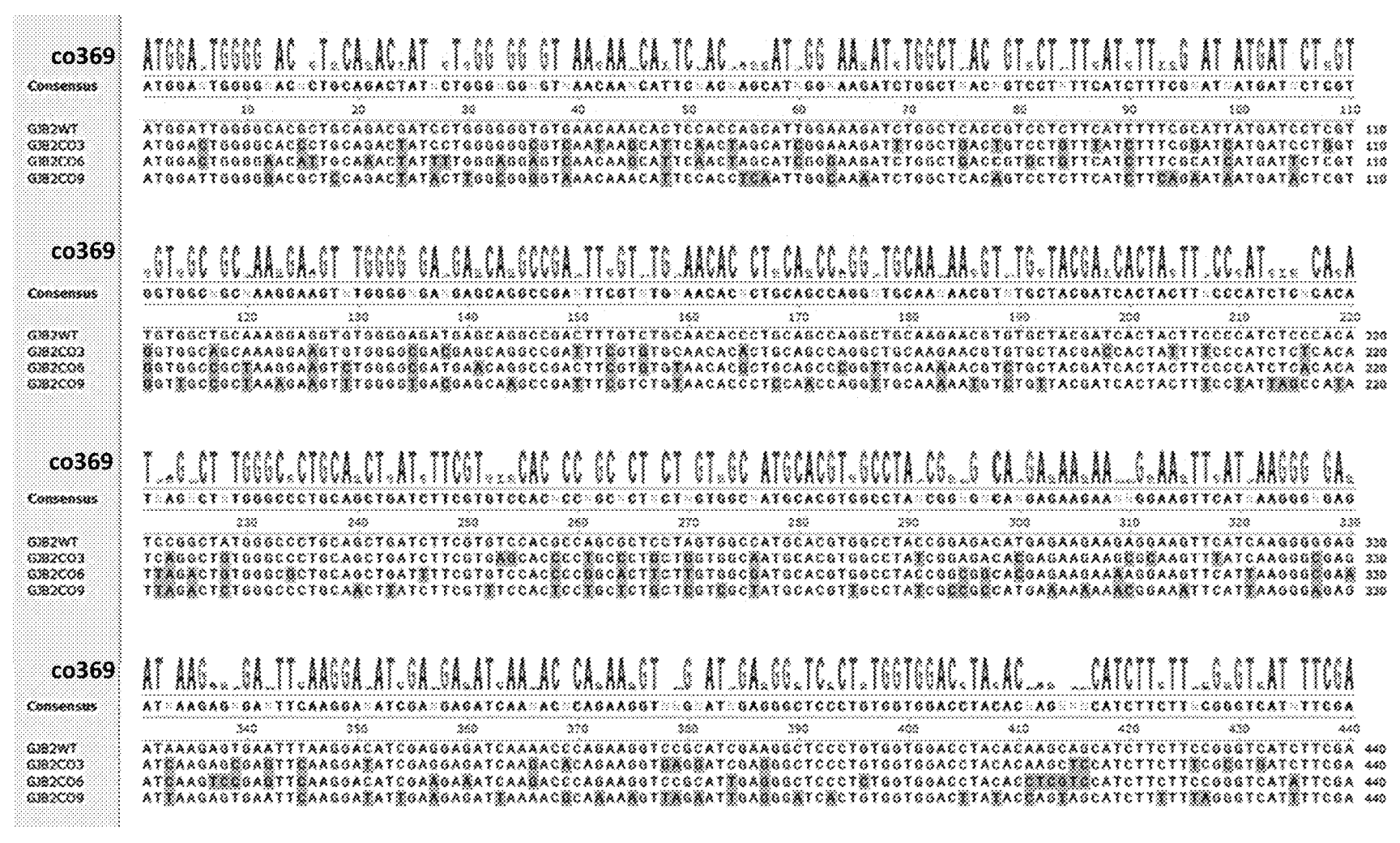

From the results described in Example 4, codon optimized GJB2 #9 (hGJB2co9) was chosen to move forward. Sequence homology of hGJB2co9 compared to WT (hGJB2) was determined to be 78% (FIG. 25). A codon optimized variant closer to WT was made in an effort to improve protein expression. The parameters for designing the variant were as follows: the nucleotide change was kept if all 3 of the co3/co6/co9 positions aligned. The nucleotide change was kept if 2 of the 3 co3/co6/co9 positions aligned. Single nucleotide changes were removed from individual co3/co6 or co9. FIG. 26 shows an alignment between the GJB2 WT, co3, co6 and co9 sequences, the consensus sequence that was determined from the alignment, and the co369 hybrid codon optimized sequence. The nucleotide changes that aligned were tested to determine how they improve protein expression.

Figure 27B:
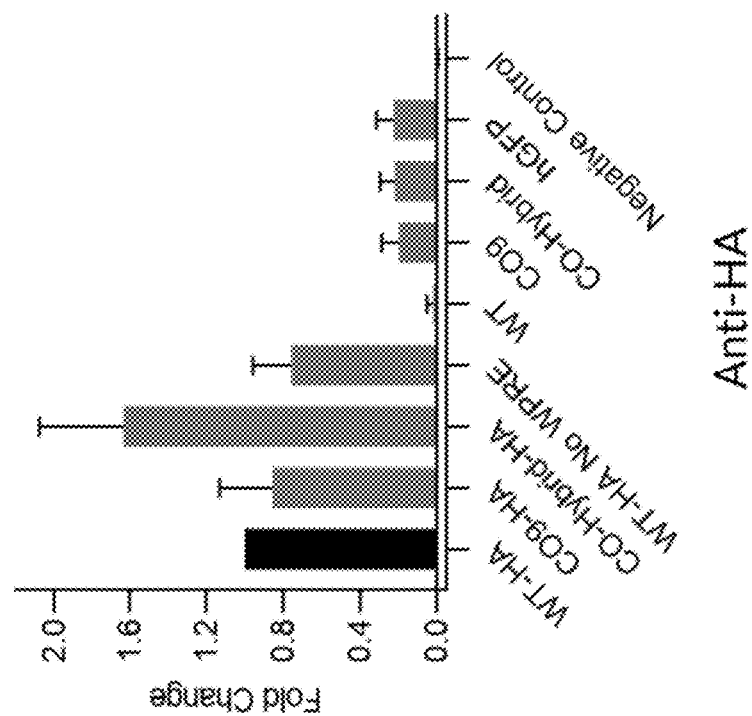
FIG. 27A and FIG. 27B show fold change of GJB2 and HA protein expression (respectively) of co9 and co369 codon optimized constructs (AAV-CBA-GJB2(X)-HA-WPRE-pA) compared to control (WT) when assayed by ELISA.
Figure 27A:
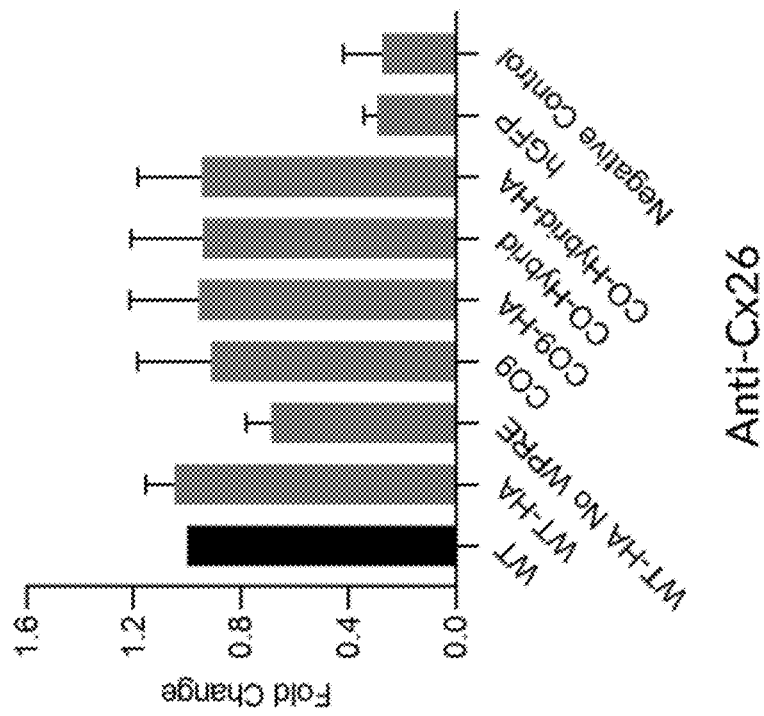

FIG. 27A and FIG. 27B show fold change of GJB2 and HA protein expression (respectively) of co9 and co369 codon optimized constructs (AAV-CBA-GJB2(X)-HA-WPRE-pA) compared to control (WT) when assayed by ELISA (Pierce Colorimetric In-Cell ELISA Kit (#62200)). Janus green staining was performed to account for differences in cell numbers in various wells (A450/A615 values) As shown in FIG. 27A, connexin-26 antibody (Cx26; ThermoFisher Scientific, CX-12H10) results showed similar protein expression for WT, co9 and co369. As shown in FIG. 27A, the absence of WPRE reduced protein expression. As shown in FIG. 27B, results show higher average protein expression for the co369-HA construct (HA Tag Mouse Monoclonal Antibody (ThermoFisher Scientific, #26183). Quadruplicate measurements were made (4 plates (n=4)). Janus green staining was performed to account for differences in cell numbers in various wells (A450/A615 values).

Figure 28B:
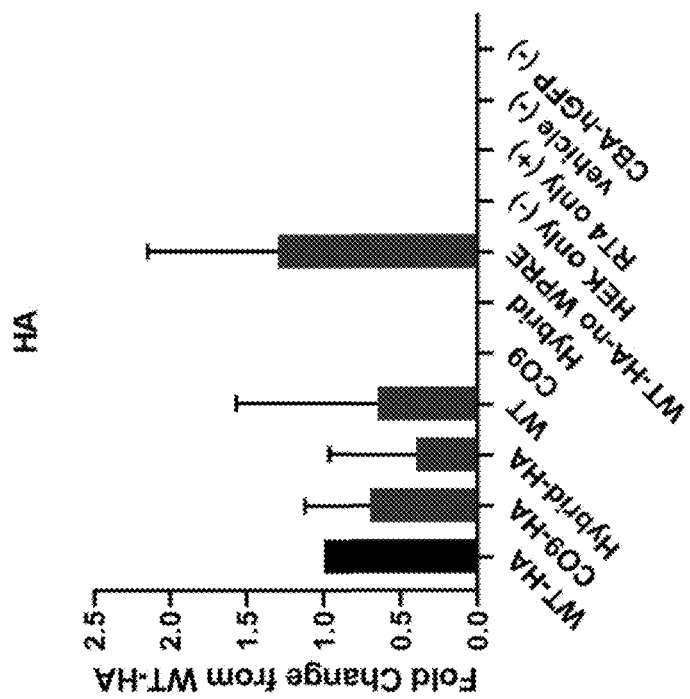
FIG. 28A and FIG. 28B show results of Western blot of codon optimized GJB2 constructs using anti-connexin 26 (FIG. 28A) and anti-HA (FIG. 28B) mouse monoclonal antibodies.
Figure 28A:
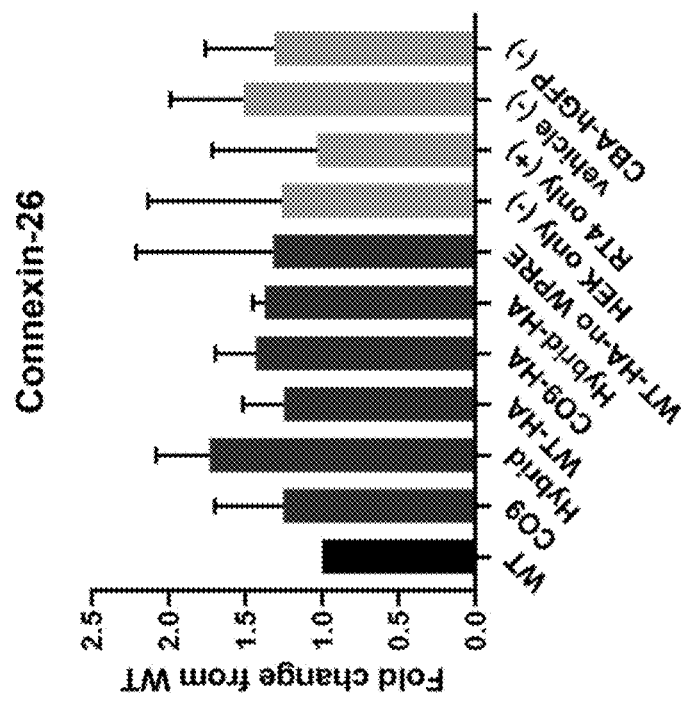

Western blotting analysis showed that the hybrid construct co369 was among the highest expressing vectors when assayed with connexin 26 mouse monoclonal antibody (FIG. 28A). When assayed with anti-HA mouse monoclonal antibody, WT was the highest expressing vector (FIG. 28B). Beta-actin was used as a loading control.

Taken together, the above assessments of protein expression supported the comparability of the co369 hybrid and WT GJB2 constructs. The ELISA results demonstrated that the co369 hybrid showed the best protein expression. The Western blot results showed that the WT and co369 hybrid showed the best protein expression. Further, immunofluorescence data will inform proper localization of protein (i.e. membrane localization).

Thus, from the studies described herein, a construct was selected with an AAV2-P2V6 capsid, a CBA-hGFP promoter and a GJB2co369 hybrid codon optimized transgene.

Example 5. In Vivo Studies with rAAV Containing GJB2 Genomic Expression Constructs The following constructs were designed to be used for in vivo testing (the terms CBA and CB are used interchangeably to refer to the CBA promoter):

pTR-CB-HybridGJB2(co369)-Flag-WPRE

Control: pTR-CB-WTGJB2-Flag-WPRE

Figure 29:
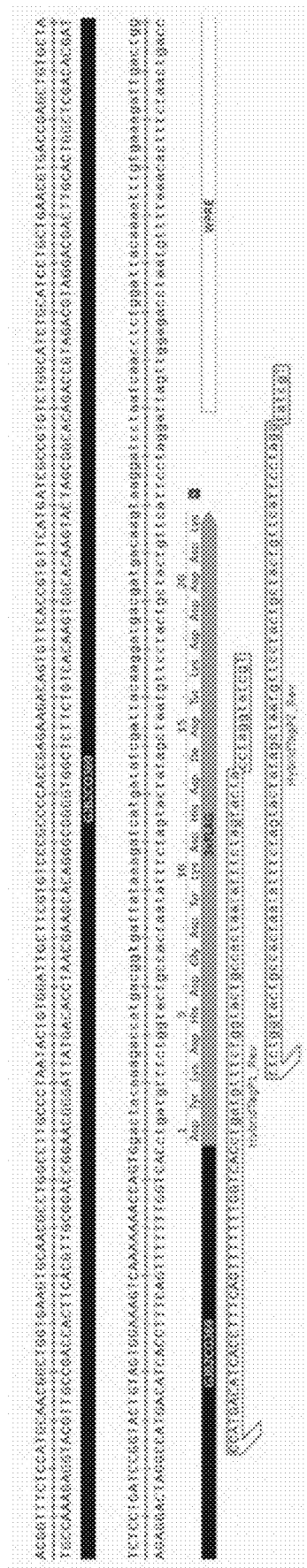
FIG. 29 shows an example of 2 step PCR for 3× flag addition using co369 as the gene of interest.
Figure 30:
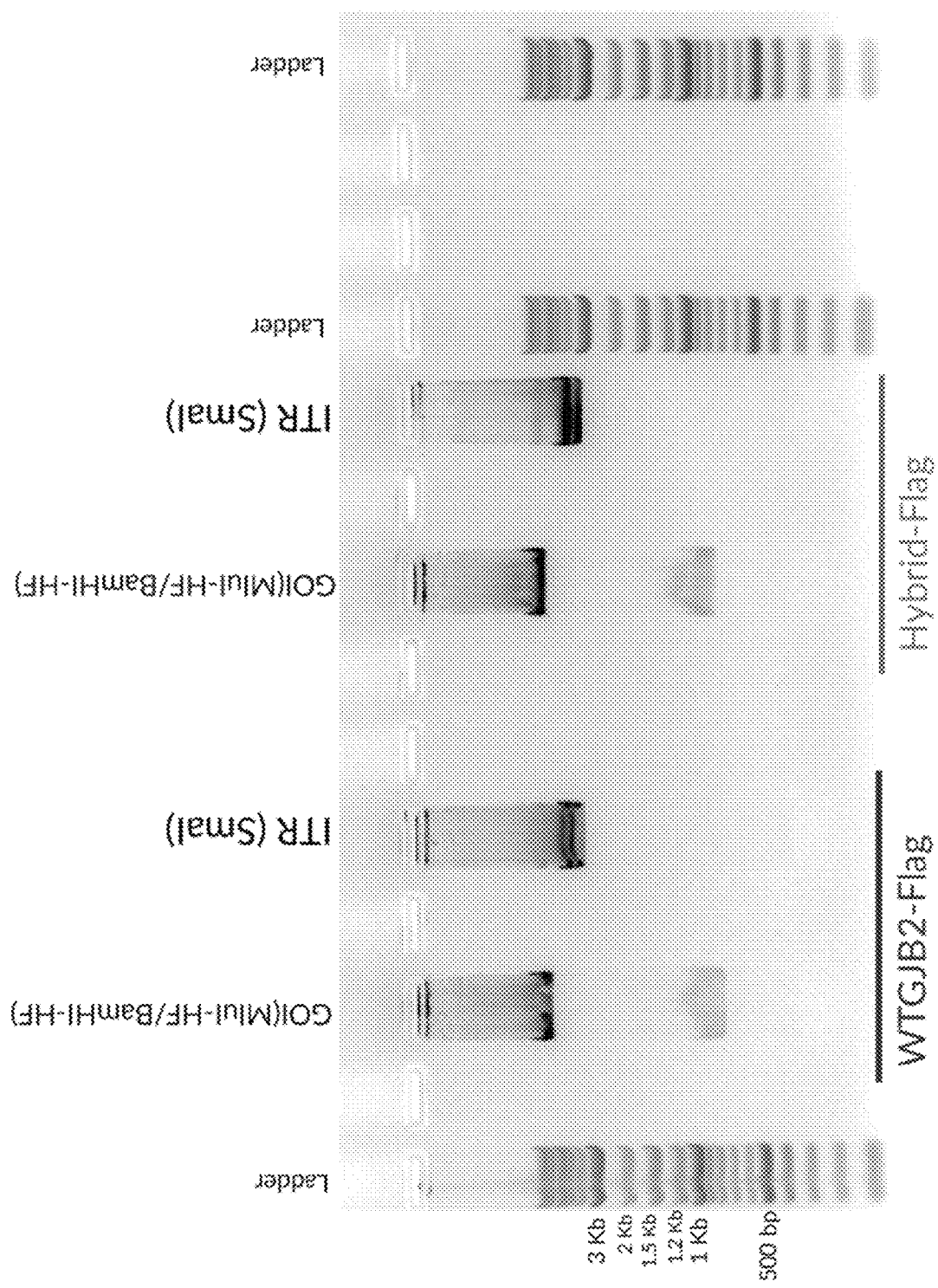
FIG. 30 shows the results of Western blot analysis, where hGJB2WT and co369 hybrid constructs show expected restriction digest fragments bands.

A two-step PCR approach for 3× flag addition to respective gene of interest was carried out to prepare the constructs. An example using the co369 hybrid is shown in FIG. 29. Western blot analysis showed that both WT and co369 hybrid flag constructs showed expected restriction digest fragments bands (FIG. 30).

Figure 31A:
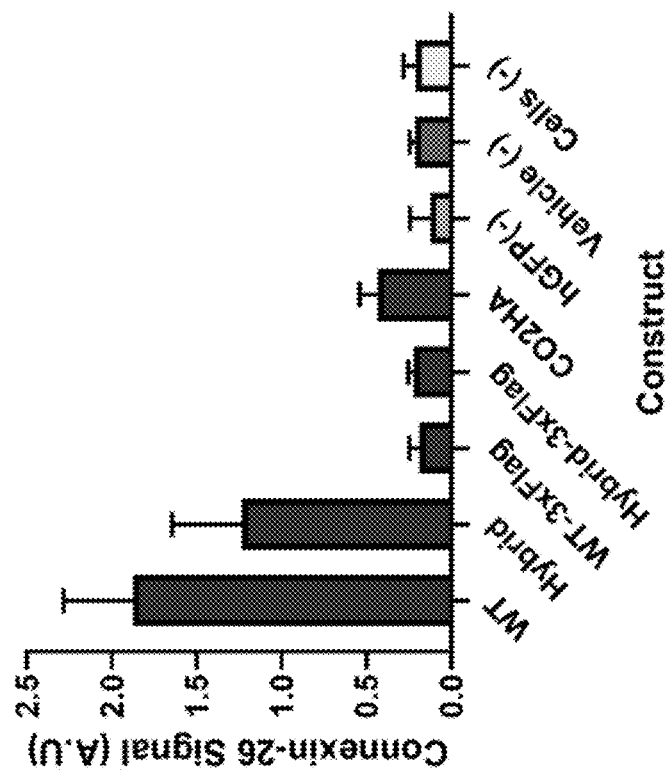
FIG. 31A and FIG. 31B show codon optimized construct expression in HEK293 cells when probing with an anti-connexin26 (anti-Cx26; CX-1E8 (33-5800)) (FIG. 31A) or an anti-flag (FIG. 31B) antibody when assayed by ELISA.
Figure 31B:
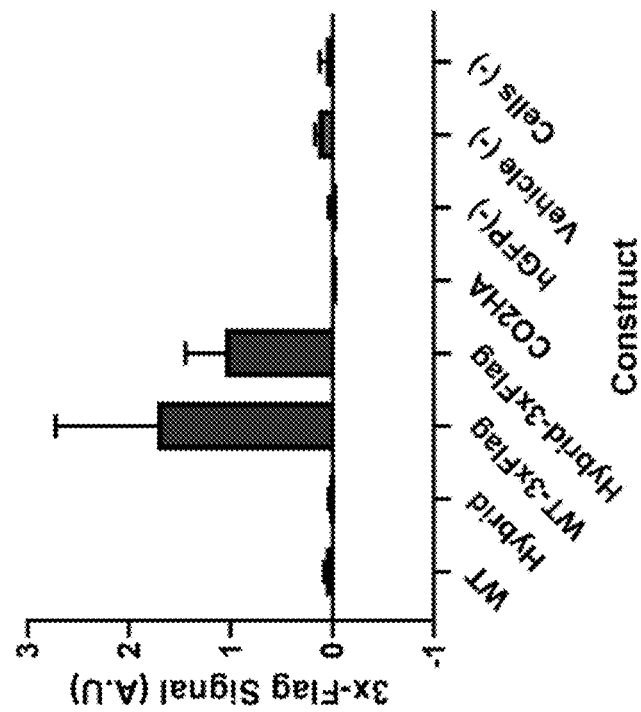
Figure 32:
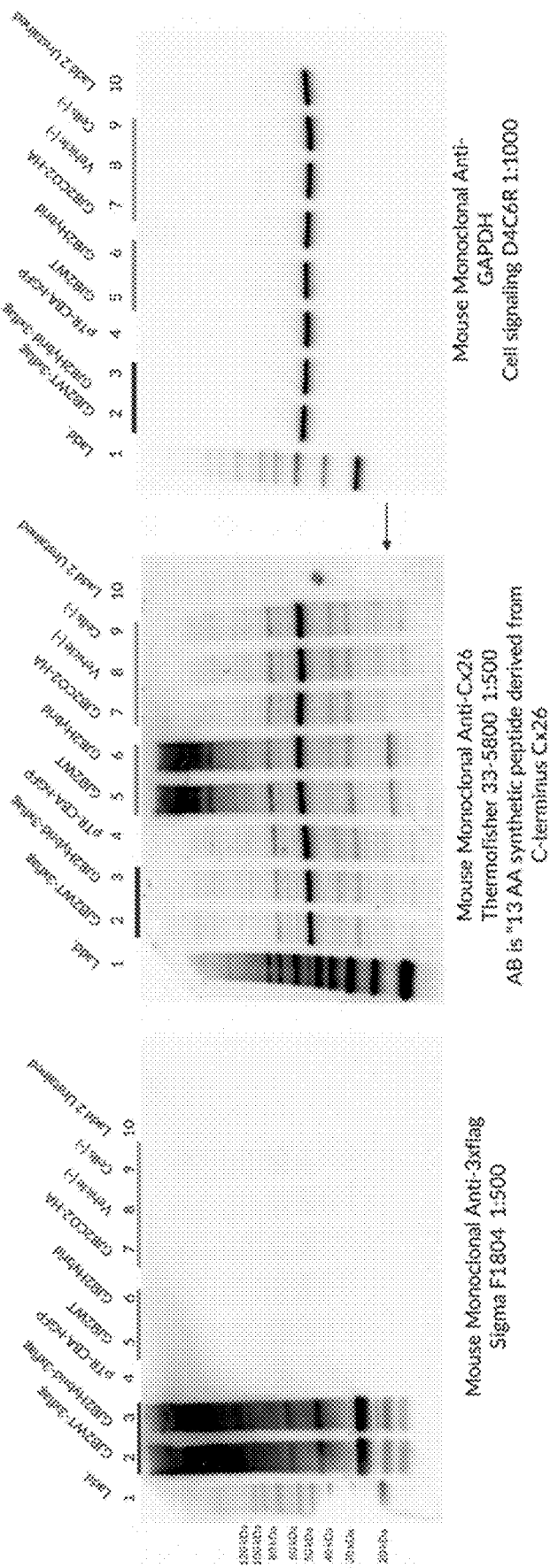
FIG. 32 are Western blots that confirm the results of the ELISA results in FIG. 31A and FIG. 31B, demonstrating that the codon optimized constructs are expressed in HEK293 cells.

FIG. 31A and FIG. 31B show codon optimized construct expression in HEK293 cells probing with an anti-connexin26 (anti-Cx26; Thermo, CX-1E8 (33-5800)) (FIG. 31A) or an anti-flag (FIG. 31B) antibody when assayed by ELISA. Tagged construct expression in HEK293 showed comparable expression when probing both Cx26 and 3× flag. Interestingly, Cx26 probing seemed to be affected by tag presence. This result was observed in Western blot as well (FIG. 32). Janus green staining was performed to account for differences in cell numbers in various wells (A450/A615 values). All groups were tested in triplicate.

Figure 33A:
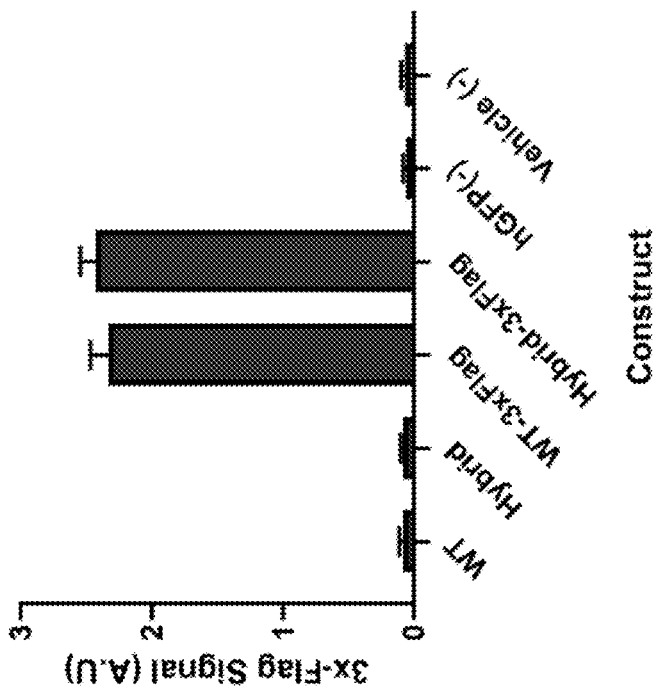
FIG. 33A and FIG. 33B show construct expression in HeLa cells when probing with an anti-connexin26 (anti-Cx26; Thermofisher 33-5800 (1:500)) (FIG. 33A) or an anti-flag (FIG. 33B) antibody when assayed by ELISA.
Figure 33B:
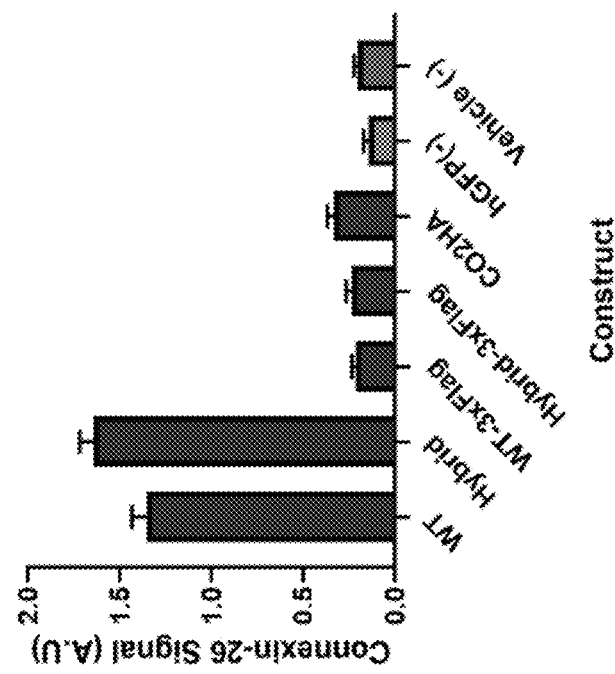

FIG. 32 are Western blots that confirm the results of the ELISA results in FIG. 31A and FIG. 31B, demonstrating that the codon optimized constructs are expressed in HEK293 cells. GAPDH probe was used to show that lysate loading was even. Lysate loading is even (GAPDH probe); Tagged construct expression in HEK293 observed as expected FIG. 33A and FIG. 33B show construct expression in HeLa cells probing with an anti-connexin26 (anti-Cx26; Thermofisher 33-5800 (1:500)) (FIG. 33A) or an anti-flag (FIG. 33B) antibody when assayed by ELISA. Tagged construct expression in HeLa shows comparable expression when probing both Cx26 and 3× flag. Cx26 probing seems to be affected by tag presence. Overall, the results in HeLa cells were comparable to previous experiment in HEK293 cells. Western blot experiments confirmed the results of the ELISA (not shown).

In an independent set of experiments, both WT and co369 hybrid constructs passed quality control tests (not shown).

In vivo studies with rAAV containing GJB2 genomic expression constructs will be carried out. Data collected will include GJB2 expression and cochlear biodistribution analyses from mouse tissue following treatment with AAV-GJB2 lead candidate (determined from in vitro studies as described in the Examples above). Data collected will also include assessment of GJB2 function by dye diffusion and whole-cell patch clamp assay.

Although the invention has been described in some detail by way of illustration and example for purposes of clarity of understanding, it should be understood that certain changes and modifications may be practiced within the scope of the appended claims. Modifications of the above-described modes for carrying out the invention that would be understood in view of the foregoing disclosure or made apparent with routine practice or implementation of the invention to persons of skill in gene therapy, molecular biology, and/or related fields are intended to be within the scope of the following claims.

All publications (e.g., Non-Patent Literature), patents, patent application publications, and patent applications mentioned in this specification are indicative of the level of skill of those skilled in the art to which this invention pertains. All such publications (e.g., Non-Patent Literature), patents, patent application publications, and patent applications are herein incorporated by reference to the same extent as if each individual publication, patent, patent application publication, or patent application was specifically and individually indicated to be incorporated by reference.

While the foregoing invention has been described in connection with this preferred embodiment, it is not to be limited thereby but is to be limited solely by the scope of the claims which follow.

The invention claimed is:

1. An isolated polynucleotide comprising a nucleic acid sequence encoding a codon optimized gap junction protein beta 2 (GJB2), wherein the nucleic acid sequence is at least 85% identical to SEQ ID NO: 18.

2. The polynucleotide of claim 1, comprising in the following order CBA-GJB2 (X)-HA-WPRE-pA, where X comprises a nucleic acid sequence at least 85% identical to SEQ ID NO: 18.

3. A host cell comprising the polynucleotide of claim 1.

4. A recombinant herpes simplex virus (rHSV) comprising the polynucleotide of claim 1.

5. A transgene expression cassette comprising:
the polynucleotide of claim 1; and
minimal regulatory elements.

6. A nucleic acid vector comprising the expression cassette of claim 5.

7. The vector of claim 6, wherein the vector is an adeno-associated viral (AAV) vector.

8. A host cell comprising the transgene expression cassette of claim 5.

9. A composition comprising the host cell of claim 8.

10. A composition comprising the transgene expression cassette of claim 5.

11. A recombinant adeno-associated (rAAV) expression vector comprising the polynucleotide of claim 1 and an AAV genomic cassette.

12. The expression vector of claim 11, wherein the AAV genomic cassette is flanked by two sequence-modulated inverted terminal repeats.

13. The expression vector of claim 11 further comprising a protein capsid variant optimally suited for cochlear delivery.

14. A composition comprising the rAAV expression vector of claim 11.

15. A composition comprising the polynucleotide of claim 1.

16. The polynucleotide of claim 1, wherein the nucleic acid sequence encoding the codon optimized GJB2 protein is at least 95% identical to SEQ ID NO: 18.

17. The polynucleotide of claim 1, wherein the nucleic acid sequence encoding the codon optimized GJB2 protein is at least 99% identical to SEQ ID NO: 18.

18. The polynucleotide of claim 1, wherein the nucleic acid sequence encoding the codon optimized GJB2 protein consists of SEQ ID NO: 18.

* * * * *

SEQUENCE LISTING

```
<160> NUMBER OF SEQ ID NOS: 43

<210> SEQ ID NO 1
<211> LENGTH: 1680
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
ctcagatctg aattcggtac ctagttatta atagtaatca attacggggt cattagttca      60
tagcccatat atggagttcc gcgttacata acttacggta aatggcccgc ctggctgacc     120
gcccaacgac ccccgcccat tgacgtcaat aatgacgtat gttcccatag taacgccaat     180
agggactttc cattgacgtc aatgggtgga gtatttacgg taaactgccc acttggcagt     240
acatcaagtg tatcatatgc caagtacgcc ccctattgac gtcaatgacg gtaaatggcc     300
cgcctggcat tatgcccagt acatgacctt atgggacttt cctacttggc agtacatcta     360
cgtattagtc atcgctatta ccatggtcga ggtgagcccc acgttctgct tcactctccc     420 catctcccc cctccccac ccccaatttt gtatttattt attttttaat tattttgtgc      480
agcgatgggg gcggggggg gggggggcg cgcgccaggc ggggcgggc ggggcgaggg     540
```

```
gcggggcggg gcgaggcgga gaggtgcggc ggcagccaat cagagcggcg cgctccgaaa    600
gtttcctttt atggcgaggc ggcggcggcg gcggccctat aaaaagcgaa gcgcgcggcg    660
ggcgggagtc gctgcgcgct gccttcgccc cgtgccccgc tccgccgccg cctcgcgccg    720
cccgccccgg ctctgactga ccgcgttact cccacaggtg agcgggcggg acggcccttc    780
tcctccgggc tgtaattagc gcttggttta atgacggctt gtttcttttc tgtggctgcg    840
tgaaagcctt gaggggctcc gggagggccc tttgtgcggg gggagcggct cgggggtgc     900 gtgcgtgtgt gtgtgcgtgg ggagcgccgc gtgcggctcc gcgctgcccg gcggctgtga    960
gcgctgcggg cgcggcgcgg ggctttgtgc gctccgcagt gtgcgcgagg ggagcgcggc   1020 cggggcggt gccccgcggt gcggggggg ctgcgagggg aacaaaggct gcgtgcgggg    1080
tgtgtgcgtg ggggggtgag cagggggtgt gggcgcgtcg gtcgggctgc aaccccccct   1140
gcacccccct ccccgagttg ctgagcacgg cccggcttcg ggtgcggggc tccgtacggg   1200
gcgtggcgcg gggctcgccc tgccgggcgg ggggtggcgg caggtggggg tgccgggcgg   1260
ggcggggccg cctcgggccg gggagggctc ggggagggg cgcggcggcc cccggagcgc    1320
cggcggctgt cgaggcgcgg cgagccgcag ccattgcctt ttatggtaat cgtgcgagag   1380
ggcgcaggga cttcctttgt cccaaatctg tgcgagccga aatctgggga ggcgccgccg   1440
caccccctct agcgggcgcg gggcgaagcg gtgcggcgcc ggcaggaagg aaatgggcgg   1500
ggagggcctt cgtgcgtcgc cgcgccgccg tccccttctc cctctccagc ctcggggctg   1560 tccgcgggg gacggctgcc ttcgggggg acggggcagg gcggggttcg gcttctggcg    1620
tgtgaccggc ggctctagag cctctgctaa ccatgttcat gccttcttct ttttcctaca   1680
```

<210> SEQ ID NO 2
<211> LENGTH: 806
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
gagtcaatgg gaaaaccca ttggagccaa gtacactgac tcaataggga cttttccattg     60 ggttttgccc agtacataag gtcaataggg ggtgagtcaa caggaaagtc ccattggagc    120
caagtacatt gagtcaatag ggactttcca atgggttttg cccagtacat aaggtcaatg    180
ggaggtaagc caatgggttt ttcccattac tgacatgtat actgagtcat tagggacttt    240
ccaatgggtt ttgcccagta cataaggtca ataggggtga tcaacagga aagtcccatt    300 ggagccaagt acactgagtc aatagggact ttccattggg ttttgccag tacaaaaggt    360 caataggggg tgagtcaatg gttttttccc attattggca catacataag gtcaataggg    420
gtgactagtg gagaagagca tgcttgaggg ctgagtgccc ctcagtgggc agagagcaca    480
tggcccacag tccctgagaa gttggggga gggtgggca attgaactgg tgcctagaga     540
aggtggggct tgggtaaact gggaaagtga tgtggtgtac tggctccacc ttttttcccca    600 gggtggggga gaaccatata taagtgcagt agtctctgtg aacattcaag cttctgcctt    660
ctccctcctg tgagtttggt aagtcactga ctgtctatgc ctgggaaagg gtgggcagga    720
ggtggggcag tgcaggaaaa gtggcactgt gaaccctgca gccctagaca attgtactaa    780
ccttcttctc tttcctctcc tgacag                                          806
```

<210> SEQ ID NO 3

```
<211> LENGTH: 1055
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ggagttccgc gttacataac ttacggtaaa tggcccgcct ggctgaccgc ccaacgaccc      60
ccgcccattg acgtcaataa tgacgtatgt tcccatagta acgccaatag ggactttcca     120
ttgacgtcaa tgggtggagt atttacggta aactgcccac ttggcagtac atcaagtgta     180
tcatatgcca agtacgcccc ctattgacgt caatgacggt aaatggcccg cctggcatta     240
tgcccagtac atgaccttat gggactttcc tacttggcag tacatctacg tattagtcat     300
cgctattacc atggtcgagg tgagcccac gttctgcttc actctcccca tctccccccc      360
ctccccaccc ccaattttgt atttatttat tttttaatta ttttgtgcag cgatggggc      420 gggggggggg ggggcgcgc gccaggcggg gcggggcggg gcgaggggcg gggcggggcg      480
aggcggagag gtgcggcggc agccaatcag agcggcgcgc tccgaaagtt ccttttatg      540 gcgaggcggc ggcggcggcg gccctataaa aagcgaagcg cgcggcgggc gggagtcgct     600
gcgcgctgcc ttcgccccgt gccccgctcc gccgccgcct cgcgccgccc gccccggctc     660
tgactgaccg cgttactaaa acaggtaagt ccggcctccg cgccgggttt tggcgcctcc     720
cgcgggcgcc cccctcctca cggcgagcgc tgccacgtca gacgaagggc gcagcgagcg     780
tcctgatcct tccgcccgga cgctcaggac agcggcccgc tgctcataag actcggcctt     840 agaacccag tatcagcaga aggacatttt aggacgggac ttgggtgact ctagggcact       900 ggttttctt ccagagagcg aacaggcga ggaaaagtag tcccttctcg gcgattctgc       960
ggagggatct ccgtggggcg gtgaacgccg atgatgcctc tactaaccat gttcatgttt    1020
tctttttttt tctacaggtc ctgggtgacg aacag                               1055

<210> SEQ ID NO 4
<211> LENGTH: 961
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
cctcagatct gaattcggta ccctagttat taatagtaat caattacggg gtcattagtt      60
catagcccat atatggagtt ccgcgttaca taacttacgg taaatggccc gcctggctga     120
ccgcccaacg accccgccc attgacgtca ataatgacgt atgttcccat agtaacgcca      180 ataggggactt tccattgacg tcaatgggtg gactatttac ggtaaactgc ccacttggca    240
gtacatcaag tgtatcatat gccaagtacg ccccctattg acgtcaatga cggtaaatgg    300
cccgcctggc attatgccca gtacatgacc ttatgggact tcctacttg gcagtacatc     360 tacgtattag tcatcgctat taccatggtc gaggtgagcc ccacgttctg cttcactctc    420
cccatctccc cccctcccc accccaatt ttgtatttat ttatttttta attatttgt        480 gcagcgatgg gggcggggg ggggggggg cgcgcgccag gcggggcggg gcggggcgag      540
gggcggggcg gggcgaggcg gagaggtgcg gcggcagcca atcagagcgg cgcgctccga    600
aagtttcctt ttatggcgag gcggcggcgg cggcggccct ataaaaagcg aagcgcgcg    660 cggggcgggag tcgctgcgac gctgccttcg ccccgtgccc cgctccgccg ccgcctcgcg    720
```

```
ccgcccgccc cggctctgac tgaccgcgtt actcccacag gtgagcgggc gggacggccc    780
ttctcctccg ggctgtaatt agcgcttggt ttaatgacgg cttgtttctt ttctgtggct    840
gcgtgaaagc cttgaggggc tccgggagct agagcctctg ctaaccatgt tcatgccttc    900
ttcttttttcc tacagctcct gggcaacgtg ctggttattg tgctgtctca tcattttggc    960
a                                                                    961
```

<210> SEQ ID NO 5
<211> LENGTH: 1675
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
gtctgcaagc agacctggca gcattgggct ggccgccccc cagggcctcc tcttcatgcc     60
cagtgaatga ctcaccttgg cacagacaca atgttcgggg tgggcacagt gcctgcttcc    120
cgccgcaccc cagcccccct caaatgcctt ccgagaagcc cattgagtag ggggcttgca    180
ttgcacccca gctgacagc ctggcatctt gggataaaag cagcacagcc cctaggggc      240
tgcccttgct gtgtggcgcc accggcggtg gagaacaagg ctctattcag cctgtgccca    300
ggaaagggga tcaggggatg cccaggcatg acagtgggt ggcagggggg gagaggaggg     360
ctgtctgctt cccagaagtc caaggacaca aatgggtgag gggactgggc agggttctga    420
ccctgtggga ccagagtgga gggcgtagat ggacctgaag tctccaggga caacagggcc    480
caggtctcag gctcctagtt gggcccagtg gctccagcgt ttccaaaccc atccatcccc    540
agaggttctt cccatctctc caggctgatg tgtgggaact cgaggaaata atctccagt     600
gggagacgga ggggtggcca gggaaacggg gcgctgcagg aataaagacg agccagcaca    660
gccagctcat gcgtaacggc tttgtggagc tgtcaaggcc tggtctctgg gagagaggca    720
caggggaggcc agacaaggaa ggggtgacct ggagggacag atccaggggc taaagtcctg    780
ataaggcaag agagtgccgg ccccctcttg ccctatcagg acctccactg ccacatagag    840
gccatgattg acccttagac aaagggctgg tgtccaatcc cagcccccag ccccagaact    900
ccagggaatg aatgggcaga gagcaggaat gtgggacatc tgtgttcaag ggaaggactc    960
caggagtctg ctgggaatga ggcctagtag gaaatgaggt ggcccttgag ggtacagaac   1020
aggttcattc ttcgccaaat tcccagcacc ttgcaggcac ttacagctga gtgagataat   1080
gcctgggtta tgaaatcaaa aagttggaaa gcaggtcaga ggtcatctgg tacagccctt   1140
ccttcccttt tttttttttt ttttttttg tgagacaagg tctctctctg ttgcccaggc   1200
tggagtggcg caaacacagc tcactgcagc ctcaacctac tgggctcaag caatcctcca   1260
gcctcagcct cccaaagtgc tgggattaca agcatgagcc accccactca gccctttcct   1320
tccttttaa ttgatgcata ataattgtaa gtattcatca tggtccaacc aacccttct    1380
tgacccacct tcctagagag agggtcctct tgattcagcg gtcagggccc cagacccatg   1440
gtctggctcc aggtaccacc tgcctcatgc aggagttggc gtgccagga agctctgcct    1500
ctgggcacag tgacctcagt ggggtgaggg gagctctccc catagctggg ctgcggccca   1560
acccccaccc ctcaggctat gccagggggt gttgccaggg gcacccgggc atcgccagtc   1620
tagcccactc cttcataaag ccctcgcatc ccaggagcga gcagagccag agcat         1675
```

```
<210> SEQ ID NO 6
<211> LENGTH: 1000
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
ctcataaatg ccaagtcctc tcgcactatg cggagtacag aggacaacga ccacagccat      60
ccctgaaccc cgcccacggc acagcgccgg agccggggtc tggggcgccg cttcctgggg     120
ggtcccgact ctcagccgcc cccgcttcac ccgggccgcc aagggctggg ggaggcggc     180 gctcggggta accgggggag actcagggcg ctggggcac ttggggaact catggggct      240 caaaggaact aggagatcgg gacctcgaag gggacttggg gggttcgggg ctttcggggg     300
cggtcggggg ttcgcggacc cgggaagctc tgaggaccca gaggccgggc gcgctccgcc     360
cgcggcgccg cccctccgt aactttccca gtctccgagg gaagaggcgg ggtgtggggt      420
gcggttaaaa ggcgccacgg cgggagacag gtgttgcggc cccgcagcgc ccgcgcgctc     480
ctctccccga ctcggagccc ctcggcggcg cccggcccag acccgcccta ggagcgcagg     540
agccccagcg cagagacccc aacgccgaga cccccgcccc ggccccgccg cgcttcctcc     600
cgacgcaggt gagcccgccg gcccggact gcccggccag gaacctggcg cggggaggga     660
ccgcgagacc cagagcggtt gcccggccgc gtgggtctcg gggaaccggg gggctggacc     720
aacacacgtc cttgggccgg ggggcggggg ccgccttctg gagcgggcgt ttctgcggcc     780
gagctccgga gctggaatgg ggcggccggg gaagtggacg cgatggcacc gcccggggtg     840
cgagtggggc cgggcgcgcg cgggagggga aaaaggcgcg ggcgagccgc cagcgcgagg     900
tttgtggtgt cgccgatgtc ccttcggggt actctagcgc agccgcctgg ctacttgacc     960
cactgccacc aaacgtttta aattcaccga aagcttagct                         1000

<210> SEQ ID NO 7
<211> LENGTH: 143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttc                                              143

<210> SEQ ID NO 8
<211> LENGTH: 143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
aaccggtgag ggagagacgc gcgagcgagc gagtgactcc ggcccgctgg tttccagcgg      60
gctgcgggcc cgaaacgggc ccgccggagt cactcgctcg ctcgcgcgtc tctccctcac     120
cggttgaggt agtgatcccc aag                                              143
```

```
<210> SEQ ID NO 9
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gacgcgcgag cgagcgagtg actccggcgg gcccgtttcg ggcccgcagc ccgctggaaa    60
ccagcgggcc ggagtcactc gctcgctcgc gcgtctctcc ctcacc                 106

<210> SEQ ID NO 10
<211> LENGTH: 678
<212> TYPE: DNA
<213> ORGANISM: Homo sapiens

<400> SEQUENCE: 10
atggattggg gcacgctgca gacgatcctg gggggtgtga acaaacactc caccagcatt    60
ggaaagatct ggctcaccgt cctcttcatt tttcgcatta tgatcctcgt tgtggctgca   120
aaggaggtgt ggggagatga gcaggccgac tttgtctgca cacccctgca gccaggctgc   180
aagaacgtgt gctacgatca ctacttcccc atctcccaca tccggctatg ggccctgcag   240
ctgatcttcg tgtccacgcc agcgctccta gtggccatgc acgtggccta ccggagacat   300
gagaagaaga ggaagttcat caaggggggag ataaagagtg aatttaagga catcgaggag   360
atcaaaaccc agaaggtccg catcgaaggc tccctgtggt ggacctacac aagcagcatc   420
ttcttccggg tcatcttcga agccgccttc atgtacgtct ctatgtcat gtacgacggc    480 ttctccatgc agcggctggt gaagtgcaac gcctggcctt gtcccaacac tgtggactgc   540
tttgtgtccc ggcccacgga agagactgtc ttcacagtgt tcatgattgc agtgtctgga   600
atttgcatcc tgctgaatgt cactgaattg tgttatttgc taattagata ttgttctggg   660
aagtcaaaaa agccagtt                                                678

<210> SEQ ID NO 11
<211> LENGTH: 678
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atggactggg gcaccctgca gactatcctg gggggcgtca ataagcattc aactagcatc    60
ggaaagattt ggctgactgt cctgtttatc tttcggatca tgatcctggt ggtggcagca   120
aaggaagtgt gggggcgacga gcaggccgat ttcgtgtgca cacactgca gccaggctgc    180 aagaacgtgt gctacgacca ctattttccc atctctcaca tcaggctgtg ggccctgcag   240
ctgatcttcg tgagcacccc tgccctgctg gtggcaatgc acgtggccta tcggagacac   300
gagaagaagc gcaagtttat caagggcgag atcaagagcg agttcaagga tatcgaggag   360
atcaagacac agaaggtgag gatcgagggc tccctgtggt ggacctacac aagctccatc   420
ttctttcgcg tgatcttcga ggccgccttt atgtacgtgt ctatgtgat gtacgacggc   480 ttttctatgc agcggctggt gaagtgcaac gcctggccct gtcctaatac agtggattgt   540
ttcgtgtcca gacccaccga agagacagtg ttcaccgtgt tatgatcgc cgtgtctggc    600 atctgcatcc tgctgaacgt gaccgagctg tgctatctgc tgatccggta ctgtagtgga    660
```

```
aagagcaaaa aacccgtg                                                  678
```

<210> SEQ ID NO 12
<211> LENGTH: 678
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
atggactggg gaacattgca aactattttg ggaggagtca caagcattc aactagcatc      60
gggaagatct ggctgaccgt gctgttcatc tttcgcatca tgattctcgt ggtggccgct    120
aaggaagtct ggggcgatga acaggccgac ttcgtgtgta cacgctgca gcccggttgc     180
aaaaacgtct gctacgatca ctacttcccc atctcacaca ttagactgtg gcgctgcag    240
ctgattttcg tgtccacccc ggcacttctt gtggcgatgc acgtggccta ccggcggcac   300
gagaagaaaa ggaagttcat taagggcgaa atcaagtccg agttcaagga catcgaagaa   360
atcaagaccc agaaggtccg cattgagggc tccctctggt ggacctacac ctcgtccatc   420
ttcttccggg tcatattcga ggccgccttt atgtacgtgt tttacgtgat gtacgacggt   480
ttcagcatgc aaagactcgt caagtgcaac gcttggcctt gccccaatac cgtggattgc   540
ttcgtgtccc gcccgaccga gaaaactgtg ttcactgtgt tcatgatcgc cgtgtccggc   600
atctgcatcc tgctgaacgt gaccgagctg tgctatctcc tgatccggta ctgtagcgga   660
aagtcgaaga agcctgtg                                                  678
```

<210> SEQ ID NO 13
<211> LENGTH: 678
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
atggattggg ggacgctcca gactatactt ggcggggtaa acaaacattc cacctcaatt    60
ggcaaaatct ggctcacagt cctcttcatc ttcagaataa tgatactcgt ggttgccgct   120
aaagaagttt ggggtgacga gcaagccgat ttcgtctgta cacccctcca accaggttgc   180
aaaaatgtct gttacgatca ctactttcct attagccata ttagactctg gccctgcaa   240
cttatcttcg tttccactcc tgctctgctc gtcgctatgc acgttgccta tcgccgccat   300
gaaaaaaaac ggaaattcat taagggagag attaagagtg aattcaagga tattgaagag   360
attaaaacgc aaaaagttag aattgaggga tcactgtggt ggacttatac cagtagcatc   420
tttttaggg tcattttcga agctgctttc atgtatgttt tctatgtaat gtacgacggt   480
ttctccatgc aacgcttggt taaatgtaac gcctggccat gccctaatac ggttgattgc   540
tttgtctccc gccctactga aaagacagtg tttaccgttt tcatgatcgc cgtaagtgga   600
atttgtatcc ttcttaacgt gaccgagttg tgctatctcc ttattcgcta ctgttcagga   660
aaaagtaaaa aaccagta                                                  678
```

<210> SEQ ID NO 14
<211> LENGTH: 27
<212> TYPE: DNA
<213> ORGANISM: Human influenza virus

<400> SEQUENCE: 14

```
tacccatacg atgttccaga ttacgct                                          27
```

<210> SEQ ID NO 15
<211> LENGTH: 589
<212> TYPE: DNA
<213> ORGANISM: Woodchuck hepatitis virus

<400> SEQUENCE: 15

```
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt tgctgacgc aaccccact      240 ggttggggca ttgccaccac ctgtcagctc ctttccggga cttcgctttc ccctccct      300 attgccacgg cggaactcat cgccgcctgc cttgcccgct gctggacagg ggctcggctg    360
ttgggcactg acaattccgt ggtgttgtcg gggaaatcat cgtccttcc ttggctgctc    420 gcctgtgttg ccacctggat tctgcgcggg acgtccttct gctacgtccc ttcggccctc    480
aatccagcgg accttcctc ccgcggcctg ctgccggctc tgcggcctct tccgcgtctt    540
cgccttcgcc ctcagacgag tcggatctcc ctttgggccg cctccccgc                589
```

<210> SEQ ID NO 16
<211> LENGTH: 122
<212> TYPE: DNA
<213> ORGANISM: Simian virus 40

<400> SEQUENCE: 16

```
taagatacat tgatgagttt ggacaaacca caactagaat gcagtgaaaa aaatgcttta     60
tttgtgaaat ttgtgatgct attgctttat ttgtaaccat tataagctgc aataaacaag    120
tt                                                                   122
```

<210> SEQ ID NO 17
<211> LENGTH: 208
<212> TYPE: DNA
<213> ORGANISM: Simian virus 40

<400> SEQUENCE: 17

```
ctgtgccttc tagttgccag ccatctgttg tttgcccctc ccccgtgcct tccttgaccc     60
tggaaggtgc cactcccact gtcctttcct aataaaatga ggaaattgca tcgcattgtc    120
tgagtaggtg tcattctatt ctgggggggtg ggtggggca ggacagcaag ggggaggatt    180
gggaagacaa tagcaggcat gctggga                                        208
```

<210> SEQ ID NO 18
<211> LENGTH: 681
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
atggactggg gcacgctgca gactatcctg gggggtgtca acaagcattc aactagcatc     60
ggaaagatct ggctgaccgt cctgttcatc tttcgcatca tgatcctcgt ggtggccgct    120
aaggaagtgt ggggcgacga gcaggccgat tcgtgtgta acaccctgca gccaggttgc    180
aaaaacgtct gctacgatca ctactttccc atctcccaca ttagactgtg ggccctgcag    240
```

```
ctgatcttcg tgtccacccc tgcgctgcta gtggccatgc acgtggccta tcggcgacac    300
gagaagaaac ggaagttcat taagggcgag atcaagagcg agttcaagga tatcgaagag    360
atcaagaccc agaaggtccg cattgagggc tccctgtggt ggacctacac cagctccatc    420
ttctttcggg tcatcttcga ggccgccttt atgtacgtgt tctatgtgat gtacgacggt    480
ttctccatgc aacggctggt gaagtgcaac gcctggcctt gccctaatac tgtggattgc    540
ttcgtgtccc gccccaccga aagacagtg ttcaccgtgt tcatgatcgc cgtgtctggc    600
atctgcatcc tgctgaacgt gaccgagctg tgctatctcc tgatccggta ctgtagtgga    660
aagtcaaaaa aaccagtgta a                                              681
```

<210> SEQ ID NO 19
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Met Asp Trp Gly Thr Leu Gln Thr Ile Leu Gly Gly Val Asn Lys His
1               5                   10                  15

Ser Thr Ser Ile Gly Lys Ile Trp Leu Thr Val Leu Phe Ile Phe Arg
            20                  25                  30

Ile Met Ile Leu Val Val Ala Ala Lys Glu Val Trp Gly Asp Glu Gln
        35                  40                  45

Ala Asp Phe Val Cys Asn Thr Leu Gln Pro Gly Cys Lys Asn Val Cys
    50                  55                  60

Tyr Asp His Tyr Phe Pro Ile Ser His Ile Arg Leu Trp Ala Leu Gln
65                  70                  75                  80

Leu Ile Phe Val Ser Thr Pro Ala Leu Leu Val Ala Met His Val Ala
                85                  90                  95

Tyr Arg Arg His Glu Lys Lys Arg Lys Phe Ile Lys Gly Glu Ile Lys
            100                 105                 110

Ser Glu Phe Lys Asp Ile Glu Glu Ile Lys Thr Gln Lys Val Arg Ile
        115                 120                 125

Glu Gly Ser Leu Trp Trp Thr Tyr Thr Ser Ser Ile Phe Phe Arg Val
    130                 135                 140

Ile Phe Glu Ala Ala Phe Met Tyr Val Phe Tyr Val Met Tyr Asp Gly
145                 150                 155                 160

Phe Ser Met Gln Arg Leu Val Lys Cys Asn Ala Trp Pro Cys Pro Asn
                165                 170                 175

Thr Val Asp Cys Phe Val Ser Arg Pro Thr Glu Lys Thr Val Phe Thr
            180                 185                 190

Val Phe Met Ile Ala Val Ser Gly Ile Cys Ile Leu Leu Asn Val Thr
        195                 200                 205

Glu Leu Cys Tyr Leu Leu Ile Arg Tyr Cys Ser Gly Lys Ser Lys Lys
    210                 215                 220

Pro Val
225
```

<210> SEQ ID NO 20
<211> LENGTH: 7
<212> TYPE: PRT
<213> ORGANISM: Adeno-associated virus

```
<400> SEQUENCE: 20

Leu Gly Glu Thr Thr Arg Pro
1               5

<210> SEQ ID NO 21
<211> LENGTH: 11
<212> TYPE: PRT
<213> ORGANISM: Adeno-associated virus

<400> SEQUENCE: 21

Pro Ser Gly Thr Thr Thr Gln Ser Arg Leu Gln
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ser Gly Asn Val Thr Gln Ser Thr Leu Gln
1               5                   10

<210> SEQ ID NO 23
<211> LENGTH: 5
<212> TYPE: PRT
<213> ORGANISM: Adeno-associated virus

<400> SEQUENCE: 23

Lys Asp Asp Glu Glu
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Asp Asp Asp Asp
1               5

<210> SEQ ID NO 25
<211> LENGTH: 5
<212> TYPE: PRT
<213> ORGANISM: Adeno-associated virus

<400> SEQUENCE: 25

Lys Thr Ser Ala Asp
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Thr Pro Ala Asp
1               5
```

```
<210> SEQ ID NO 27
<211> LENGTH: 5
<212> TYPE: PRT
<213> ORGANISM: Adeno-associated virus

<400> SEQUENCE: 27

Lys Gln Asp Ala Glu
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Gln Asp Gly Glu
1               5

<210> SEQ ID NO 29
<211> LENGTH: 12
<212> TYPE: PRT
<213> ORGANISM: Adeno-associated virus

<400> SEQUENCE: 29

Gln Gly Ser Glu Lys Thr Asn Val Asp Ile Glu Lys
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Glu Asp Ala Thr Glu Asn Asn Ile Asp Ile Asp Arg
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Ser Ala Ala Gly Ala Asp Val Ala Ile Asp Ser
1               5                   10

<210> SEQ ID NO 32
<211> LENGTH: 5
<212> TYPE: PRT
<213> ORGANISM: Adeno-associated virus

<400> SEQUENCE: 32

Asp Gly Glu Asp Phe
1               5

<210> SEQ ID NO 33
<211> LENGTH: 681
```

<212> TYPE: DNA
<213> ORGANISM: Homo sapiens

<400> SEQUENCE: 33

```
atggattggg gcacgctgca gacgatcctg gggggtgtga acaaacactc caccagcatt      60
ggaaagatct ggctcaccgt cctcttcatt tttcgcatta tgatcctcgt tgtggctgca     120
aaggaggtgt ggggagatga gcaggccgac tttgtctgca cacccctgca gccaggctgc     180
aagaacgtgt gctacgatca ctacttcccc atctcccaca tccggctatg ggccctgcag     240
ctgatcttcg tgtccacgcc agcgctccta gtggccatgc acgtggccta ccggagacat     300
gagaagaaga ggaagttcat caaggggggag ataaagagtg aatttaagga catcgaggag     360
atcaaaaccc agaaggtccg catcgaaggc tccctgtggt ggacctacac aagcagcatc     420
ttcttccggg tcatcttcga agccgccttc atgtacgtct tctatgtcat gtacgacggc     480
ttctccatgc agcggctggt gaagtgcaac gcctggcctt gtcccaacac tgtggactgc     540
tttgtgtccc ggcccacgga aagactgtc ttcacagtgt tcatgattgc agtgtctgga     600
atttgcatcc tgctgaatgt cactgaattg tgttatttgc taattagata ttgttctggg     660
aagtcaaaaa agccagttta a                                                681
```

<210> SEQ ID NO 34
<211> LENGTH: 681
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
atggattggg ggacgctcca gactatactt ggcggggtaa acaaacattc cacctcaatt      60
ggcaaaatct ggctcacagt cctcttcatc ttcagaataa tgatactcgt ggttgccgct     120
aaagaagttt ggggtgacga gcaagccgat ttcgtctgta caccctcca accaggttgc     180
aaaaatgtct gttacgatca ctactttcct attagccata ttagactctg gccctgcaa     240
cttatcttcg tttccactcc tgctctgctc gtcgctatgc acgttgccta tcgccgccat     300
gaaaaaaac ggaaattcat taagggagag attaagagtg aattcaagga tattgaagag     360
attaaaacgc aaaaagttag aattgaggga tcactgtggt ggacttatac cagtagcatc     420
ttttttaggg tcattttcga agctgctttc atgtatgttt tctatgtaat gtacgacggt     480
ttctccatgc aacgcttggt taaatgtaac gcctggccat gccctaatac ggttgattgc     540
tttgtctccc gccctactga aaagacagtg tttaccgttt tcatgatcgc cgtaagtgga     600
atttgtatcc ttcttaacgt gaccgagttg tgctatctcc ttattcgcta ctgttcagga     660
aaaagtaaaa aaccagtata a                                                681
```

<210> SEQ ID NO 35
<211> LENGTH: 440
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (36)..(36)
<223> OTHER INFORMATION: a, c, t, or g
<220> FEATURE:
<221> NAME/KEY: modified_base
<222> LOCATION: (264)..(264)

```
<223> OTHER INFORMATION: a, c, t, or g
<220> FEATURE:
<221> NAME/KEY: modified_base
<222> LOCATION: (270)..(270)
<223> OTHER INFORMATION: a, c, t, or g
<220> FEATURE:
<221> NAME/KEY: modified_base
<222> LOCATION: (276)..(276)
<223> OTHER INFORMATION: a, c, t, or g

<400> SEQUENCE: 35
atggaytggg gvacvctgca gactathctg ggvggngtva acaarcattc macyagcaty      60
ggvaagatct ggctsachgt cctsttcatc tttcgvatha tgathctcgt ggtggchgcw     120
aaggaagtbt gggghgayga gcaggccgay ttcgtstgya acacvctgca gccaggytgc     180
aaraacgtst gctacgatca ctacttyccc atctchcaca tyagrctvtg ggccctgcag     240
ctgatcttcg tgtccachcc dgcnctbctn gtggcnatgc acgtggccta ycggmgvcay     300
gagaagaarm ggaagttcat yaagggvgag athaagagyg arttcaagga yatcgargag     360
atcaaracvc agaaggtbmg vatygagggc tccctgtggt ggacctacac magbwscatc     420
ttcttycggg tcathttcga                                                 440

<210> SEQ ID NO 36
<211> LENGTH: 440
<212> TYPE: DNA
<213> ORGANISM: Homo sapiens

<400> SEQUENCE: 36
atggattggg gcacgctgca gacgatcctg gggggtgtga acaaacactc caccagcatt      60
ggaaagatct ggctcaccgt cctcttcatt tttcgcatta tgatcctcgt tgtggctgca     120
aaggaggtgt ggggagatga gcaggccgac tttgtctgca cacccctgca gccaggctgc     180
aagaacgtgt gctacgatca ctacttcccc atctcccaca tccggctatg ggccctgcag     240
ctgatcttcg tgtccacgcc agcgctccta gtggccatgc acgtggccta ccggagacat     300
gagaagaaga ggaagttcat caagggggag ataaagagtg aatttaagga catcgaggag     360
atcaaaaccc agaaggtccg catcgaaggc tccctgtggt ggacctacac aagcagcatc     420
ttcttccggg tcatcttcga                                                 440

<210> SEQ ID NO 37
<211> LENGTH: 440
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
atggactggg gcaccctgca gactatcctg ggggcgtca ataagcattc aactagcatc       60
ggaaagattt ggctgactgt cctgtttatc tttcggatca tgatcctggt ggtggcagca     120
aaggaagtgt ggggcgacga gcaggccgat ttcgtgtgca cacactgca gccaggctgc      180 aagaacgtgt gctacgacca ctattttccc atctctcaca tcaggctgtg ggccctgcag     240
ctgatcttcg tgagcacccc tgccctgctg gtggcaatgc acgtggccta tcggagacac     300
gagaagaagc gcaagtttat caagggcgag atcaagagcg agttcaagga tatcgaggag     360
atcaagacac agaaggtgag gatcgagggc tccctgtggt ggacctacac aagctccatc     420
ttctttcgcg tgatcttcga                                                 440
```

<210> SEQ ID NO 38
<211> LENGTH: 440
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
atggactggg gaacattgca aactattttg ggaggagtca acaagcattc aactagcatc      60
gggaagatct ggctgaccgt gctgttcatc tttcgcatca tgattctcgt ggtggccgct     120
aaggaagtct ggggcgatga acaggccgac ttcgtgtgta cacgctgca gcccggttgc      180 aaaaacgtct gctacgatca ctacttcccc atctcacaca ttagactgtg ggcgctgcag     240
ctgattttcg tgtccacccc ggcacttctt gtggcgatgc acgtggccta ccggcggcac     300
gagaagaaaa ggaagttcat taagggcgaa atcaagtccg agttcaagga catcgaagaa     360
atcaagaccc agaaggtccg cattgagggc tccctctggt ggacctacac ctcgtccatc     420
ttcttccggg tcatattcga                                                  440

<210> SEQ ID NO 39
<211> LENGTH: 440
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
atggattggg ggacgctcca gactatactt ggcggggtaa acaaacattc cacctcaatt      60
ggcaaaatct ggctcacagt cctcttcatc ttcagaataa tgatactcgt ggttgccgct     120
aaagaagttt ggggtgacga gcaagccgat ttcgtctgta cacccctcca accaggttgc     180
aaaaatgtct gttacgatca ctactttcct attagccata ttagactctg gccctgcaa     240 cttatcttcg tttccactcc tgctctgctc gtcgctatgc acgttgccta tcgccgccat     300
gaaaaaaaac ggaaattcat taagggagag attaagagtg aattcaagga tattgaagag     360
attaaaacgc aaaaagttag aattgaggga tcactgtggt ggacttatac cagtagcatc     420
ttttttaggg tcattttcga                                                  440

<210> SEQ ID NO 40
<211> LENGTH: 320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
acggtttctc catgcaacgg ctggtgaagt gcaacgcctg ccttgccct aatactgtgg       60 attgcttcgt gtcccgcccc accgagaaga cagtgttcac cgtgttcatg atcgccgtgt     120
ctggcatctg catcctgctg aacgtgaccg agctgtgcta tctcctgatc cggtactgta     180
gtggaaagtc aaaaaaacca gtggactaca agaccatga cggtgattat aaagatcatg     240
atatcgatta caaggatgac gatgacaagt aaggatccta atcaacctct ggattacaaa     300
atttgtgaaa gattgactgg                                                  320

<210> SEQ ID NO 41

```
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 42
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tgctatggat ccatcatgat ctttataatc accgtcatgg tctttgtagt ccactggttt      60
ttttgacttt ccactacagt acc                                             83

<210> SEQ ID NO 43
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tgctatggat ccttacttgt catcgtcatc cttgtaatcg atatcatgat ctttataatc      60
accgtcatgg tctt                                                       74
```